US011996175B2

(12) United States Patent
Craig et al.

(10) Patent No.: US 11,996,175 B2
(45) Date of Patent: *May 28, 2024

(54) TRUSTED THIRD-PARTY COMPUTERIZED PLATFORM USING BIOMETRIC VALIDATION DATA STRUCTURE FOR AI-BASED HEALTH WALLET

(71) Applicant: NextGen Monetization Trust, Newark, DE (US)

(72) Inventors: Brayden Craig, Sydney (AU); Christopher John Burke, Central (HK)

(73) Assignee: Peninsula Accumulator Trust, Newark, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/845,808

(22) Filed: Jun. 21, 2022

(65) Prior Publication Data
US 2022/0328149 A1 Oct. 13, 2022

Related U.S. Application Data

(63) Continuation of application No. 17/221,827, filed on Apr. 4, 2021, now Pat. No. 11,437,127, which is a
(Continued)

(51) Int. Cl.
*G16H 10/60* (2018.01)
*G06K 7/14* (2006.01)
(Continued)

(52) U.S. Cl.
CPC ........... *G16H 10/60* (2018.01); *G06K 7/1417* (2013.01); *G06N 7/01* (2023.01); *G16H 10/20* (2018.01); *G16H 15/00* (2018.01)

(58) Field of Classification Search
CPC ........ G16H 10/60; G16H 10/20; G16H 15/00; G16H 40/67; G16H 80/00; G06K 7/1417; G06N 7/01; G06F 21/52
(Continued)

(56) References Cited

U.S. PATENT DOCUMENTS 5,719,950 A 2/1998 Osten et al.
7,627,334 B2 12/2009 Cohen et al.
(Continued)

FOREIGN PATENT DOCUMENTS

WO WO2019032301 A1 2/2019
WO WO2019225553 A1 11/2019

OTHER PUBLICATIONS

Wilson, Travel Vaccines Enter the Digital Age: Creating a Virtual Immunization Record, 2016, Am. J. Trop. Med. Hyg., 94(3), 2016, pp. 485-488 (Year: 2016).*
(Continued)

*Primary Examiner* — Joshua B Blanchette
*Assistant Examiner* — Tran N Nguyen
(74) *Attorney, Agent, or Firm* — Carr & Ferrell LLP

(57) ABSTRACT

A process registers, at the user mobile computing device, one or more health-related documents for inclusion in a cloud-based digital health wallet. Furthermore, the process receives, at a user mobile computing device, a biometric identification input from the user for the registration of the one or more health-related documents. The process sends, from the user mobile computing device to a server computing device that stores the cloud-based digital health wallet, a first coded version of the biometric identification input for storage in a biometric validation data structure. Additionally, the process determines, at the user mobile computing device, a location of the user. Moreover, the process sends, from the user mobile computing device to the server computing device, a validation request at the location. The validation request includes a second coded version of a subsequently inputted biometric input from the user at the location.

20 Claims, 46 Drawing Sheets

Related U.S. Application Data continuation-in-part of application No. 16/817,844, filed on Mar. 13, 2020, now abandoned.

(51) Int. Cl.
- *G06N 7/01* (2023.01)
- *G16H 10/20* (2018.01)
- *G16H 15/00* (2018.01)

(58) Field of Classification Search
USPC .......................................................... 705/2–3
See application file for complete search history.

(56) References Cited

U.S. PATENT DOCUMENTS

| | | | |
|---|---|---|---|
| 10,204,704 B1 | 2/2019 | Wurst | |
| 10,296,716 B1 | 5/2019 | Skocic | |
| 10,791,461 B1 | 9/2020 | Gailloux et al. | |
| 10,998,101 B1 | 5/2021 | Tran | |
| 11,055,390 B1* | 7/2021 | Kragh | H04W 12/08 |
| 11,437,127 B2* | 9/2022 | Craig | G06K 7/1417 |
| 2002/0100802 A1 | 8/2002 | Sehr | |
| 2008/0045806 A1* | 2/2008 | Keppler | A61B 5/1172 |
| | | | 600/300 |
| 2010/0046806 A1 | 2/2010 | Baughman et al. | |
| 2014/0081857 A1 | 3/2014 | Bonalle et al. | |
| 2014/0313007 A1 | 10/2014 | Harding | |
| 2015/0227937 A1 | 8/2015 | Giles | |
| 2015/0324540 A1* | 11/2015 | Moloney-Egnatios | |
| | | | G16H 10/20 |
| | | | 705/3 |
| 2016/0210429 A1 | 7/2016 | Ortiz | |
| 2016/0224773 A1 | 8/2016 | Ramaci | |
| 2016/0371438 A1 | 12/2016 | Annulis | |
| 2018/0167386 A1 | 6/2018 | Bhatt et al. | |
| 2018/0336543 A1 | 11/2018 | Van Os et al. | |
| 2019/0057390 A1 | 2/2019 | Maheshwari et al. | |
| 2019/0156345 A1 | 5/2019 | Chen et al. | |
| 2019/0220583 A1 | 7/2019 | Douglas et al. | |
| 2019/0303551 A1 | 10/2019 | Tussy | |
| 2019/0080072 A1 | 12/2019 | Van Os et al. | |
| 2020/0042685 A1 | 2/2020 | Tussy et al. | |
| 2020/0279585 A1* | 9/2020 | Rothschild | G11B 27/031 |
| 2020/0358762 A1 | 12/2020 | Adams | |
| 2021/0098118 A1 | 4/2021 | Bass et al. | |
| 2021/0266737 A1 | 8/2021 | Burke | |
| 2021/0272123 A1 | 9/2021 | Burke | |
| 2021/0286864 A1 | 9/2021 | Burke | |
| 2021/0287768 A1 | 9/2021 | Craig et al. | |
| 2021/0326422 A1* | 10/2021 | Sly | G06V 40/70 |
| 2022/0013200 A1* | 1/2022 | Marz | G06Q 50/26 |

OTHER PUBLICATIONS

Mahfouz et al., "A Survey on Behavioral Biometric Authentication on Smartphones", arxiv.org, retrieved on [Apr. 14, 2021]. Retrieved from the internet <URL: https://arxiv.org/pdf/1801.09308.pdf>, Jan. 28, 2018, 16 pages.

Hassan, "Creation of Quality Customer Identification for Financial Institutions", UMI ProQuest Information and Learning Company, Spring 2005, pp. 1-87.

Wilson, "Travel Vaccines Enter the Digital Age: Creating a Virtual Immunization Record," American Journal of Tropical Medicine Hygiene, 94(3), Mar. 4, 2016, pp. 485-488.

* cited by examiner

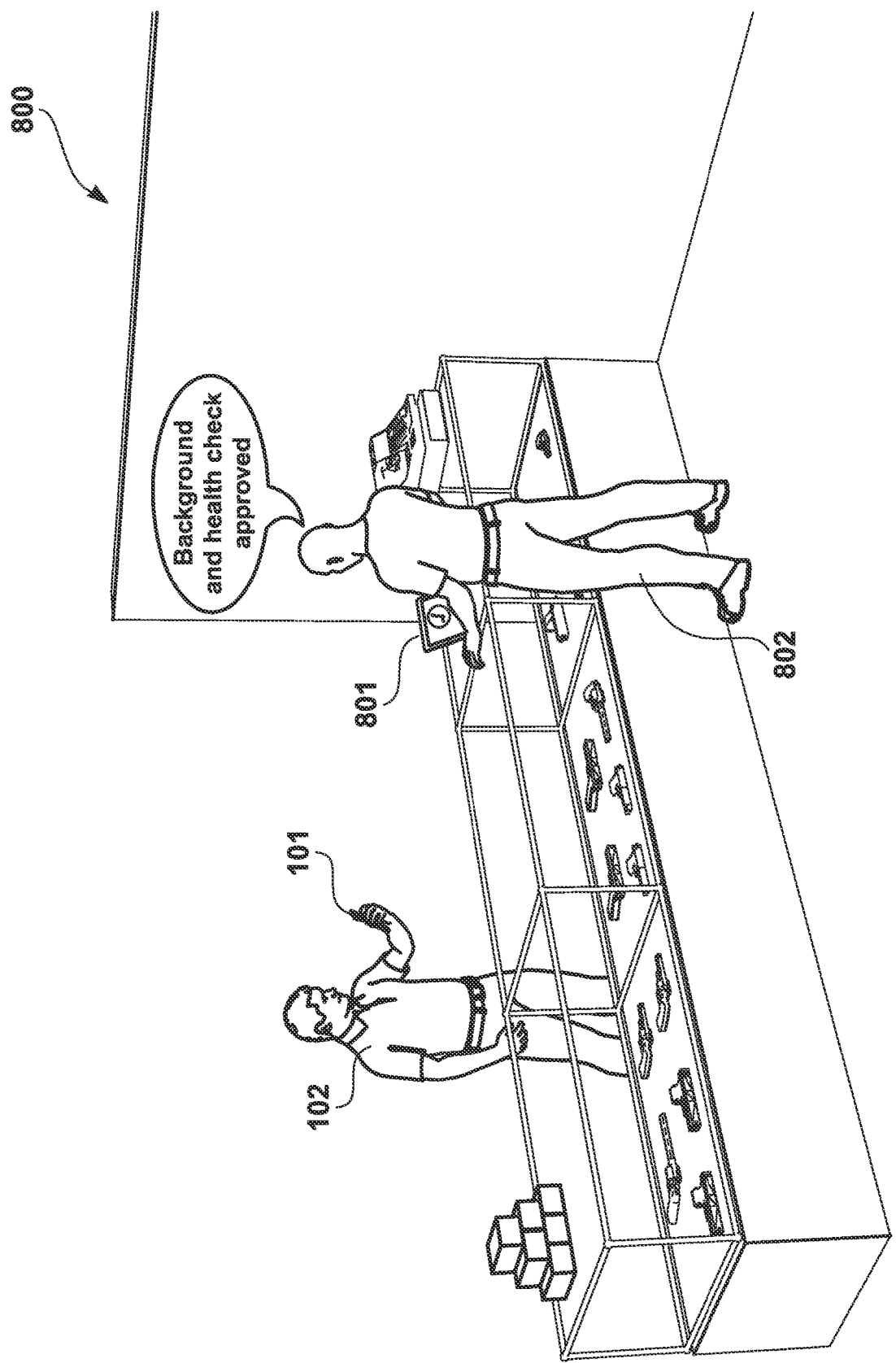

TRUSTED THIRD-PARTY COMPUTERIZED PLATFORM USING BIOMETRIC VALIDATION DATA STRUCTURE FOR AI-BASED HEALTH WALLET

RELATED APPLICATIONS

This patent application is a Continuation application of U.S. patent application Ser. No. 17/221,827, filed on Apr. 4, 2021, entitled TRUSTED THIRD-PARTY COMPUTERIZED PLATFORM FOR AI-BASED HEALTH WALLET, which is a Continuation-In-Part application of U.S. patent application Ser. No. 16/817,844, filed on Mar. 13, 2020, entitled DUAL-MODE BIOMETRIC CONFIGURATION FOR USER VALIDATION AND USER HEALTH CHECK TO DETERMINE ACCESS TO PRODUCTS AND/OR SERVICES. All of the aforementioned disclosures are hereby incorporated by reference in their entireties including all references cited therein.

BACKGROUND

1. Field

This disclosure generally relates to the field of biometric devices. More particularly, the disclosure relates to biometric analysis of a user.

2. General Background

Spanning millennia to the present, communities of varying sizes (workplaces, colleges, universities, villages, towns, cities, states, provinces, nations, etc.) have faced recurring social policy challenges. In any community-based environment, the core concern is typically managing the health and well-being of the group of human beings in that environment. Although many community-based protocols have provided numerous benefits in the way of basic and essential services (food, water, shelter, electricity, plumbing, transportation, etc.), they have been lacking in other areas.

A particular challenge in a community-based environment is virus transmission: human beings are susceptible to various forms of illness based on living and working with other human beings, who may have been infected with a virus. A common response by entities (e.g., governments, hospitals, etc.) managing community protocols is reactionary, namely manufacturing and prescribing medications to address symptoms after people have actually obtained the virus. As an example, millions of people in the United States get the common cold each year, and have to take numerous days off of work, leading to reductions in work productivity. Even though the common cold spreads so quickly from person-to-person, affecting so many people year-after-year, the vast majority of over-the-counter medications are directed toward symptom relief/mitigation, rather than virus transmission prevention. And given that prescribed medications, such as antibiotics, are typically ineffective against viruses, such as the rhinovirus that is one of the many viruses that can lead to the common cold, the reactionary approach has not mitigated the transmission of numerous viruses.

To further exacerbate matters, a number of viruses typically lead to health complications that extend beyond losses in work productivity. In particular, viruses such as influenza and corona virus disease nineteen ("COVID-19") have threatened the lives of many people on a global scale. In the case of influenza, vaccines are typically manufactured on a yearly basis, but their efficacy is often lackluster (e.g., often less than fifty percent; sometimes even less than thirty percent); a contributing factor being mutations of the virus that essentially work around the vaccine. And with respect to COVID-19, the efficacy of current vaccines against mutations is still relatively unknown.

Furthermore, existing approaches to checking symptoms of patrons, such as travelers, often involves non-compliant social distancing protocols. For example, a service provider employee (e.g., airline representative) often has to come within close proximity to the patron to check if the patron is exhibiting any systems.

Accordingly, community-based environments currently do not have effective systems in place for effectively managing community protocols in an optimal manner to minimize risks, from a variety of sources, to the health and well-being of community members.

SUMMARY

In one aspect of the disclosure, a process receives, at a mobile computing device, a biometric identification input from a user. Furthermore, the process compares, with a processor at the mobile computing device, the biometric identification input with a previously-stored biometric identification input to validate an identity of the user. Moreover, the process measures, at the mobile computing device, one or more health parameters of the user. Finally, the process sends, based upon the validation of the identity of the user, the one or more health measurements to an access device that grants access to the user to a product or service based upon the one or more health measurements complying with one or more health criteria to validate a health check of the user.

In another aspect of the disclosure, the process sends, with a processor at the mobile computing device, the biometric identification input to an access device to obtain identification validation of the user, in addition to health criteria validation.

In yet another aspect of the disclosure, a process registers, at the user mobile computing device, one or more health-related documents for inclusion in the cloud-based digital health wallet. Furthermore, the process receives, at the user mobile computing device, a biometric identification input from the user for the registration of the one or more health-related documents. The process sends, from the user mobile computing device to a server computing device that stores the cloud-based digital health wallet, a first coded version of the biometric identification input for storage in a biometric validation data structure. Additionally, the process determines, at the user mobile computing device, a location of the user. Moreover, the process sends, from the user mobile computing device to the server computing device, a validation request at the location. The validation request includes a second coded version of a subsequently inputted biometric input from the user at the location. Upon receiving a validation of the second coded version matching the first coded version stored in the biometric validation data structure, the process receives, at the user mobile computing device from the server computing device that stores the cloud-based digital health wallet, a digital health report associated with the user. The health report includes data based on a subset of the one or more health-related documents selected according to one or more health compliance requirements of a service provider at the location.

In another aspect of the disclosure, a process registers, at a server computing device, one or more health-related documents for inclusion in a cloud-based digital health wallet that is stored by the server computing device. Furthermore, at a process block, the process receives, at the server computing device from the user mobile computing device, a biometric identification input from a user for the registration. At a process block, the process receives, at the server computing device from the mobile computing device, a first coded version of the biometric identification input for storage in a biometric validation data structure. Additionally, at a process block, the process receives, at the server computing device from the user mobile computing device at the location, a validation request and location data. The validation request includes a second coded version of a subsequently inputted biometric input from the user at the location. The location data corresponds to the location. Also, the process performs, at the server computing device, a validation of the second coded version matching the first coded version stored in the biometric validation data structure. Finally, the process generates a digital health report upon the performance of the validation. The digital health report includes data based on a subset of the one or more health-related documents selected according to one or more health compliance requirements of a service provider at the location.

In yet another aspect of the disclosure, a computer program product is provided. The computer program product comprises a non-transitory computer useable storage device having a computer readable program, which when executed on the computing device causes the computing device to perform the foregoing process. Alternatively, an apparatus may implement the foregoing processes.

BRIEF DESCRIPTION OF THE DRAWINGS

The above-mentioned features of the present disclosure will become more apparent with reference to the following description taken in conjunction with the accompanying drawings wherein like reference numerals denote like elements and in which:

FIG. 8B illustrates a point of sale ("POS") device indicating that the identification and health validations were successful, thereby allowing the firearm representative to proceed with the sale of the firearm to the user.

DETAILED DESCRIPTION

Figure 1A:
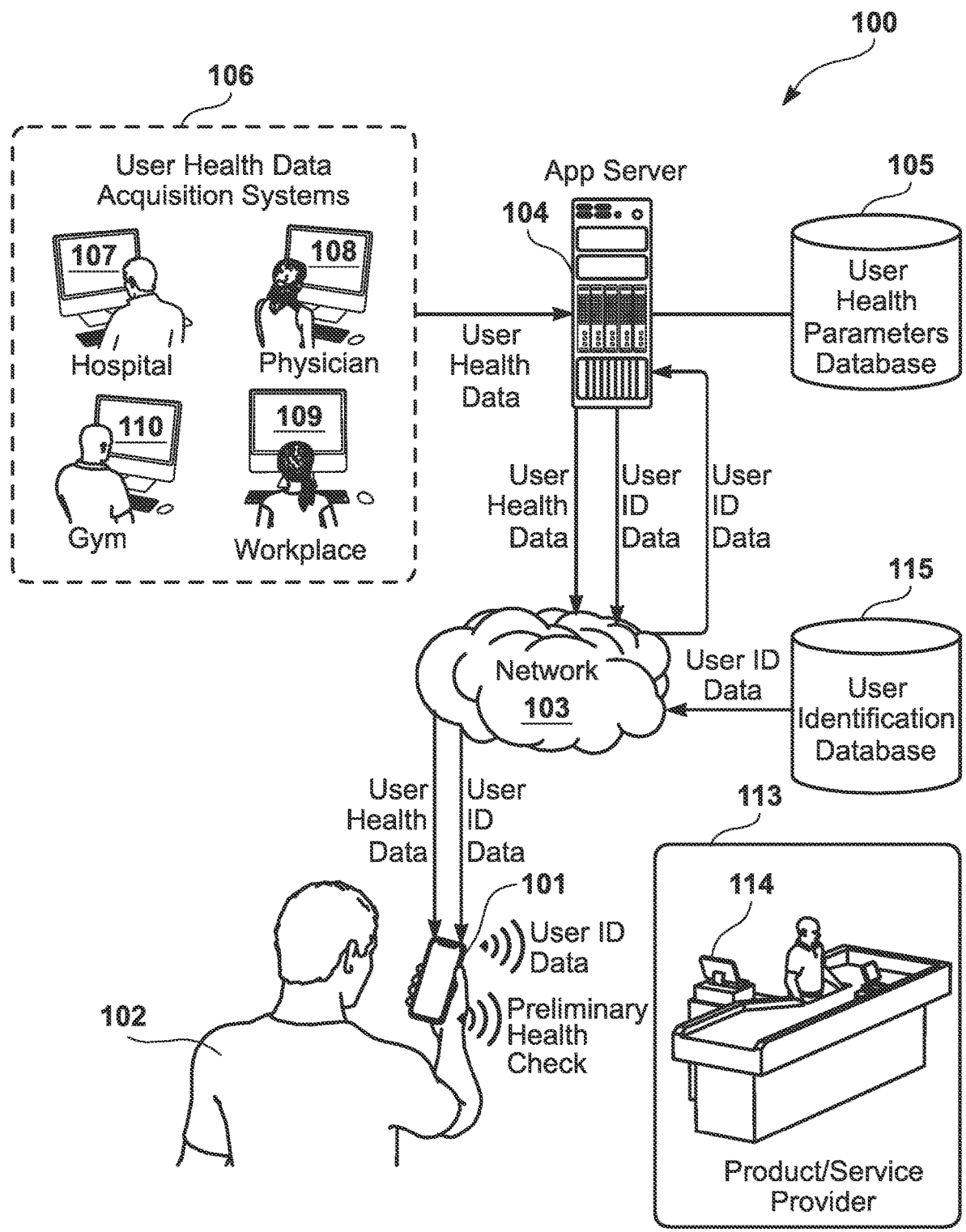
FIG. 1A illustrates a cloud-based configuration that utilizes an application server to perform processing of one or more sets of biometric data to validate a user's identity and establish a preliminary health check for that user.

A trusted third-party computerized platform is configured to implement an artificial-intelligence ("AI") based health wallet that may be operated by users via a software application ("app") invoked on their mobile computing devices. Firstly, the health wallet allows users to register various forms of health-related data all via the cloud-based platform of the trusted third-party. (The phrase "health-related" data is intended to include all data that may be necessary for a patron to obtain access to a specific service, such as travel. Non-limiting examples include vaccine records, symptom data (real-time or previously determined), forms of identification (e.g., driver's license, passport, etc.), boarding pass, etc. Health-related data may have different meanings and requirements based upon different contexts (e.g., travel may require a driver's license, boarding pass, With each upload of health-related data, the user is required to provide data (e.g., thumbprint, iris scan, etc.), which may be either directly sent to the trusted third party or coded in a manner (e.g., via encryption, a hash function, etc.) for storage in a database by the trusted third-party without sending the actual biometric data.

Secondly, the AI system is utilized to generate a health access report particular to a given service. For example, subsequent to a user generating the health wallet, the user may want to board an airplane. Upon arrival at the airport, the AI system may obtain the geolocation data of the user, and automatically generate a health access report, from the health-related data of the user and/or real-time data obtained from the user via measurements conducted via the mobile device of the user, based upon the particular requirements for air travel at that airport. (Additional requirements may be imposed based upon the travel itinerary of the user, such as requirements to a particular destination.) In essence, the AI system automatically generates different reports based on the requirements associated with services at different geolocations.

Upon the health report being generated, the user may be required to provide a biometric to provide an extra layer of authentication that all of the contents in the health wallet are that of the user. For example, coded biometric data may be sent to the trusted third-party platform for verification. As a result, an indication of verification may be displayed by the mobile device.

The trusted third-party computerized platform allows service providers to allow users access to various services without any additional computer hardware implemented at a given location. The user's mobile phone may ingest necessary data, generate a customized health report based on the specific requirements at a given geolocation, and provide confirmation of compliance with all health requirements at that geolocation prior to allowing for access. Furthermore, fraudulent use of medical records may be avoided, or at least minimized, via the user authentication protocols implemented by the trusted third-party computerized platform. Should a particular service provider want to automate confirmation review of the health reports in an expeditious manner, rather than having human representatives view the health report of each user on a corresponding phone, various computerized equipment may be utilized to automatically check the health records of the users. For example, in one embodiment, the user's health record may be sent from the mobile phone of the user via Near-Field Communications ("NFC") to a device at the geolocation of the service provider. In another embodiment, the user's health record the data of the health report may be encoded into a coded digital representation, such as a quick response ("QR") code, for scanning by a device positioned at the geolocation.

Also, a dual-mode biometric configuration is provided to accomplish at least two objectives prior to providing access to products and/or services: user identification validation and health check validation. In contrast with the reactionary approach of previous community-based protocols, the dual-mode biometric configuration is preemptive in identifying symptoms that should lead to a denial of access to products and/or services for the overall well-being of a community. Although virus strains may vary significantly in quantity, potency, and mutations, the number of symptoms indicative of a potential threat to a community is relatively small by comparison. For example, a person with a temperature of over one hundred four degrees is in no condition to be going to work, using public transportation, or driving a vehicle, irrespective of the underlying condition that caused such symptoms in that person. Given the exponential rate of viral infection of many viruses (e.g., common cold, influenza, COVID-19, etc.), preventing exposure of one contagious person to even a small group of people may prevent thousands of infections.

In one embodiment, a software application is specifically configured to operate on a user's mobile computing device (e.g., smartphone, tablet device, smartwatch, smart bracelet, smart necklace, smart apparel, etc.) for performing biometric validation of a user with respect to identification and health check. The mobile computing device, itself, may perform the biometric identification validation by comparing the biometric data inputted by the user with biometric data of the user previously stored by the mobile computing device. As a result of such localized biometric validation, the software application may allow for access and external transmission of data associated with the validated user (e.g., e-tickets, access codes, medication prescriptions, payment data, etc.). In addition, the software application may conduct, via one or more integrated or external health monitoring devices, a preliminary health check on the user simultaneously, or in real-time (i.e., as measured by a humanly imperceptible delay) with, the biometric identification validation of the user. The software application may then be configured to transmit user access data with the preliminary health check data to a provider of a product or service, which may then determine, based on its own healthcare management protocols, whether or not to allow the product or service to be provided to the user. In another embodiment, the software application is configured to internally determine compliance with the healthcare management protocol. For instance, one set of health check parameters for one person may have significantly different meaning for that of another. The software application may customize the preliminary health check according to the specific user of the mobile computing device.

In another embodiment, the biometric validation and preliminary health check may be performed external to the mobile computing device. For example, a product provider may be required by regulation to confirm the identity of the user. Accordingly, the product provider system may receive the biometric data from the mobile computing device of the user to perform a comparison with a remote database of biometric data.

FIGS. 1A-1D illustrate various dual-mode biometric configurations 130 of user mobile computing device 101. In particular, FIG. 1A illustrates a cloud-based configuration 100 that utilizes an application server 104 to perform processing of one or more sets of biometric data to validate a user's identity and establish a preliminary health check for that user. Without the limiting the applicability of the cloud-based configuration 100 to various contexts, the cloud-based configuration 100, in its essence, uses biometric data to allow for a user 102, via a mobile computing device 101, to obtain access to a product or service from a product/service provider 113. (The product/service provider 113 is illustrated as being operated by a user, but may be partially, or completely, operated autonomously. For instance, the product/service provider 113 may be an automated facility, kiosk, vending machine, automobile, UAV, etc.) Furthermore, in order to obtain the product or service for the user 102, the user mobile computing device 101 may provide two layers of biometric data, via proximity-based wireless communication (e.g., Near Field Communication ("NFC"), radio frequency identification ("RFID"), BLUETOOTH, etc.), to a product/service provider access device 114.

With respect to the cloud-based configuration 100, the application server 104 may be in operable communication with various user health data acquisition systems 106 (e.g., hospital system 107, physician system 108, workplace system 109, gym system 110, etc.), which are instructed to obtain various health parameters with respect to the user 102. (Alternatively, or in addition, the application server 104 may also receive health parameters pertaining to the user 102 from a wearable device directly worn by the user 102.) In essence, the health parameters obtained from the user health data acquisition systems 106 may establish a baseline of health data for the particular user 102. Furthermore, the health parameters may include additional information, such as electronic medical records, medication prescriptions, physician instructions, etc. In one embodiment, the health parameters of the user 102 may be stored in a user health parameters database 105 in a centralized location for fast search and access by the application server 104.

In addition, in one embodiment, the application server 104 may be in operable communication with a user identification database 115, which stores the biometric data necessary to validate the particular user 102 at a given product/service provider 113 prior to the product/service provider 113 granting access to the product or service to the user 102. For example, the user identification database 115 may store a fingerprint of the user 102, and send that fingerprint data to the mobile computing device 101 at the point of access so that the mobile computing device 101 may compare that fingerprint with a fingerprint received at the mobile computing device 101. In essence, the mobile computing device 101 may validate that the user 102 is who he or she says he or she is prior to the product/service provider 113 granting access to the product or service. (The phrase "granting access" is intended to encompass a sale or a removal of a restriction on an item or service, whether currently owned by the user 102 or not.)

Figure 1B:
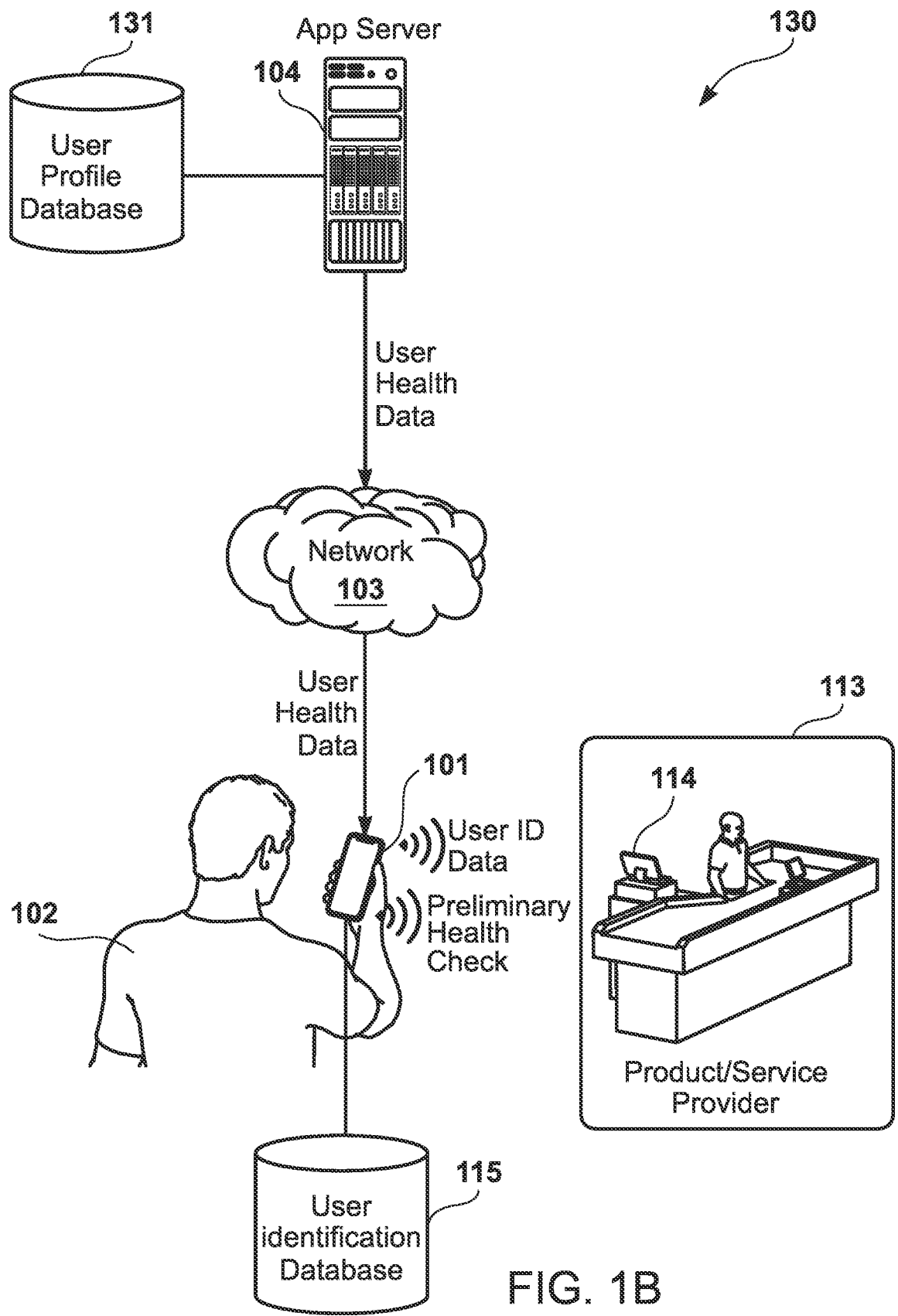
FIG. 1B illustrates that the user identification database may be integrated within the mobile computing device.

In an alternative, embodiment, the user identification database 115 is integrated within the mobile computing device 101, as illustrated in FIG. 1B. In other words, the mobile computing device 101 may locally store all of the user identification data of the user 102, without any external exposure of that access data to remotely situated systems. As a result, the user 102 may maintain the privacy of his or her data, while still allowing for his or her identify to be confirmed. In other words, the mobile computing device 101 stores the biometric identification data (iris scan, fingerprint, thumbprint, palm scan, etc.) of the user 102. Upon receiving a user input of biometric data at the point of access for the product/service, the mobile computing device 101 may perform a comparison of the biometric data to validate the identity of the user 102. Just as illustrated in FIG. 1A, the mobile computing device in FIG. 1B may transmit a proximity-based signal to the product/service provider access device 114 indicating that biometric identification has been validated. As an example, the mobile computing device 101 may transmit an image of a photo id along with a biometric identification approval signal to the product/service provider access device 114. In another embodiment, the biometric validation performed in FIGS. 1A and 1B is only used by the mobile computing device 101 to release preliminary health check biometric data to the product/service provider access device 114, not for identification.

Additionally, the application server 104 may be in operable communication with a user profile database 131. For example, the user 102, himself or herself, may provide the user health parameters as inputs via the mobile computing device 101, for storage in the user profile database 131. In one embodiment, the user 102 provides users inputs (e.g., virtual keyboard inputs, swipes, gestures, etc.) to input the health parameters. In another embodiment, the user 102 invokes the mobile computing device 101 to capture the health parameters for the user 102. For example, the user 102 may use an image capture device integrated within the mobile computing device 101 to capture baseline user data, such as pupil dilation, body temperature, etc.

Figure 1C:
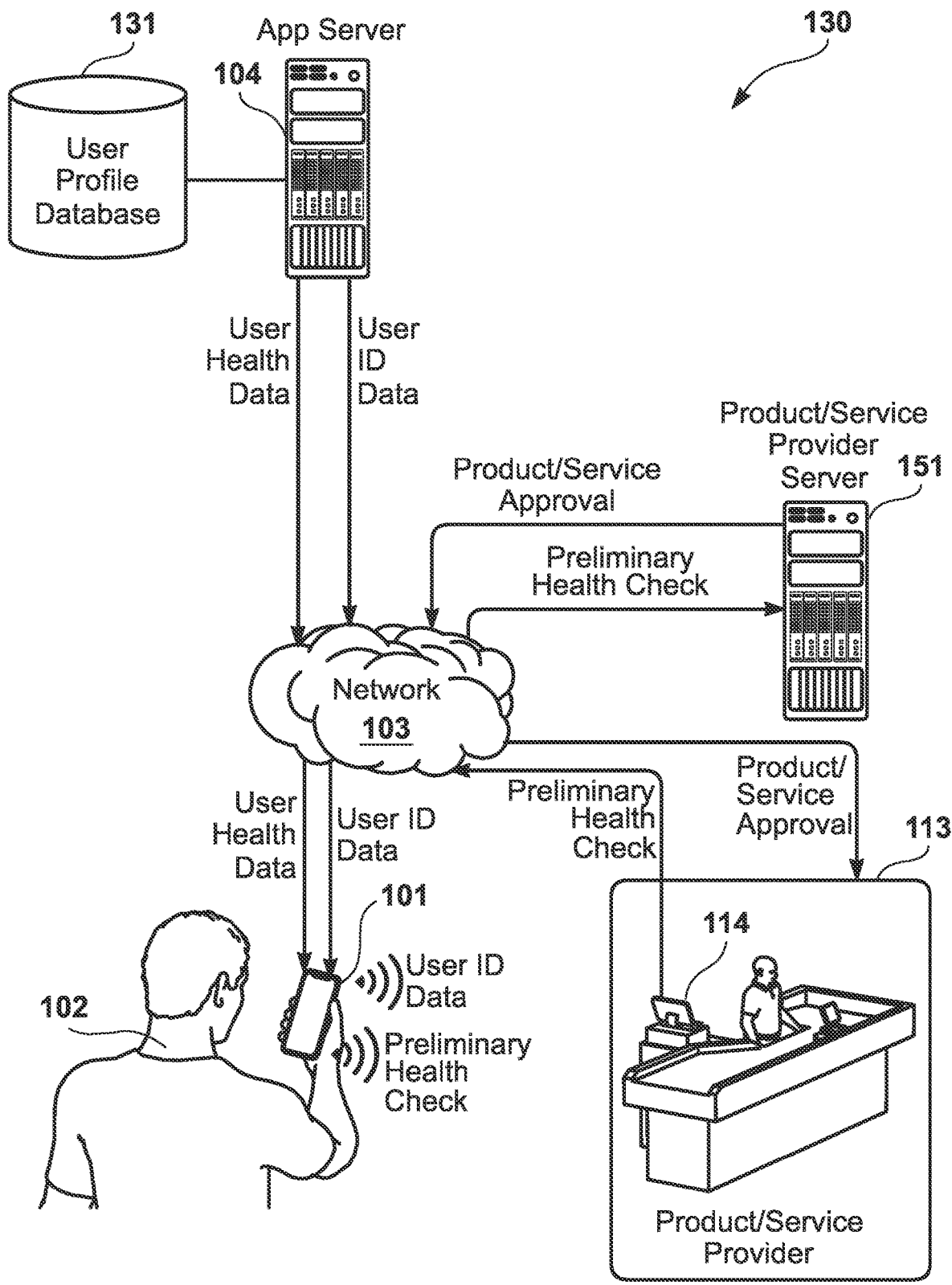
FIG. 1C illustrates the product/service provider access device transmitting the preliminary health check data to a product/service provider server, which may be remotely situated from the product/service provider, that assesses the compliance of the preliminary health check data.

In one embodiment, as illustrated in FIGS. 1A and 1B, the product/service provider 113 may receive the preliminary health check data from the mobile computing device 101, and determine, either automatically via the product/service provider access device 114 or manually by a product/service provider representative, whether the preliminary health check complies with one or more criteria for product/service access. For example, the product/service provider 113 may have established its own preliminary health check thresholds (e.g., body temperature, blood pressure, pulse rate, pupil dilation, sweat detection, etc.), or follow those of a regulatory entity, which have to be met prior to granting access of a product/service to the user 102. In another embodiment, as illustrated in FIG. 1C, the product/service provider access device 114 transmits the preliminary health check data to a product/service provider server 151, which may be remotely situated from the product/service provider 113, that assesses the compliance of the preliminary health check data. The product/service provider server 151 may then provide an instruction to the product/service provider access device 114 as to whether the product/service provider access device 114 should grant access to the product/service to the user 102.

Figure 1D:
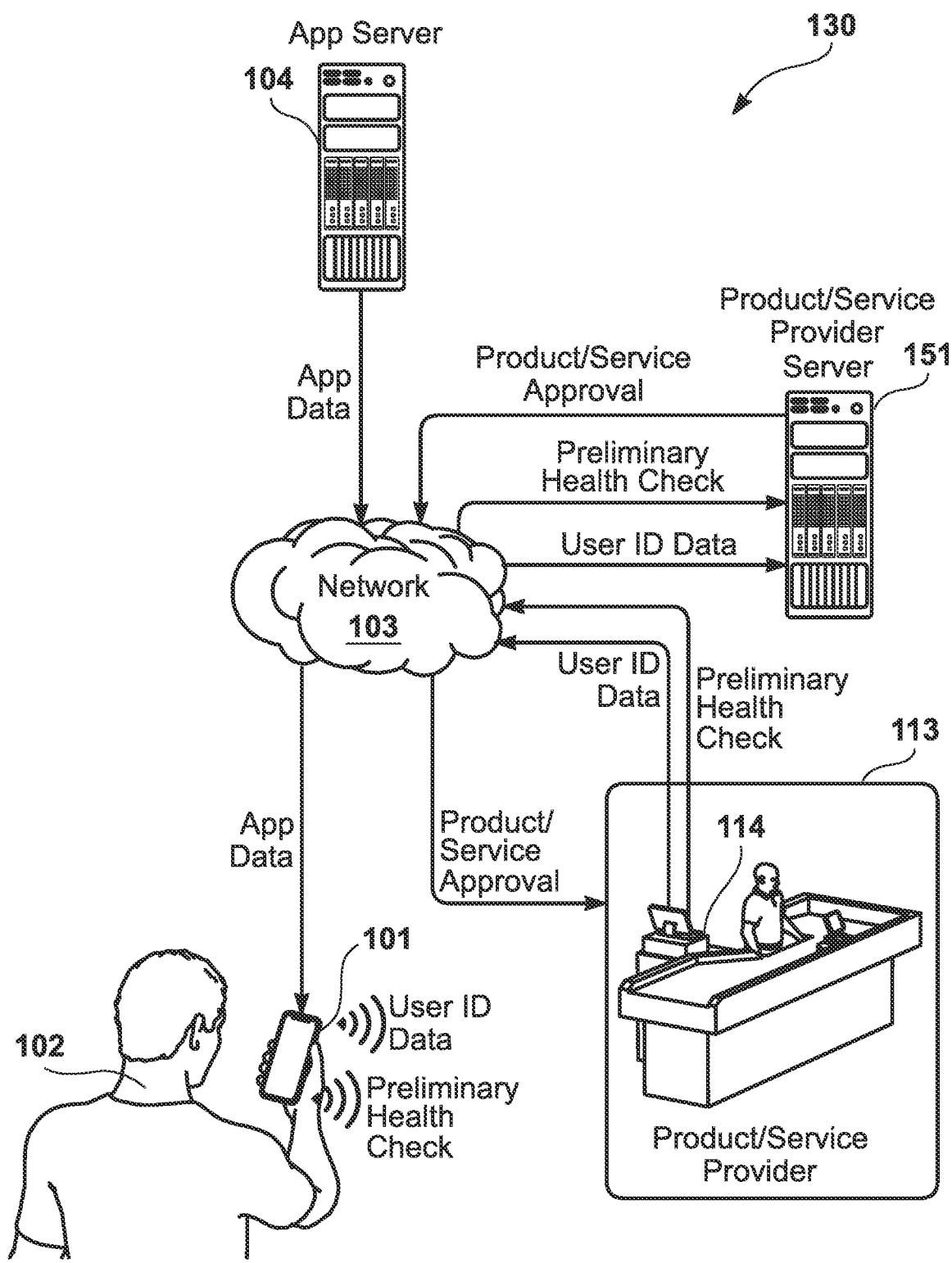
FIG. 1D illustrates the mobile computing device transmitting both layers of biometric data to the product/service provider access device for transmission to the product/service provider server, which may perform both user validation and preliminary health check compliance.

Finally, as illustrated in FIG. 1D, the mobile computing device 101 may transmit both layers of biometric data to the product/service provider access device 114 for transmission to the product/service provider server 151, which may perform both user validation and preliminary health check compliance; upon a successful determination for both, the product/service provider server 151 may provide an instruction to the product/service provider access device 114 to grant the user 102 access to the product or service.

With any of the configurations provided for in FIGS. 1A-1D, the mobile computing device 101 may communicate, via a network 103, with the application server 104 to obtain data for rendering of a software application. The user 102 may interact with the software application to perform tasks, such as establishing health baseline data, biometric identification validation, and user inputs for preliminary health checks.

In essence, the mobile computing device 101 illustrated in FIGS. 1A-1D is an integrated mobile device that has componentry encompassed therein to process both layers of biometric data: identification data and preliminary health check data. For example, the mobile computing device 101 may have a touch-based display screen, which can receive thumbprint data to identify the user 102, and an infrared ("IR") sensor that may detect the temperature of the user 102. As a result, the user 102 may use just one device to obtain access to various products and/or services. In one embodiment, each set of biometric data is associated with a distinct user input (i.e., a thumbprint for identification and an ear scan for temperature). In another embodiment, one user input may encompass both sets of biometric data (e.g., a facial recognition scan may be performed to obtain facial data points as well as measure the forehead temperature of the user 102).

Figure 2A:
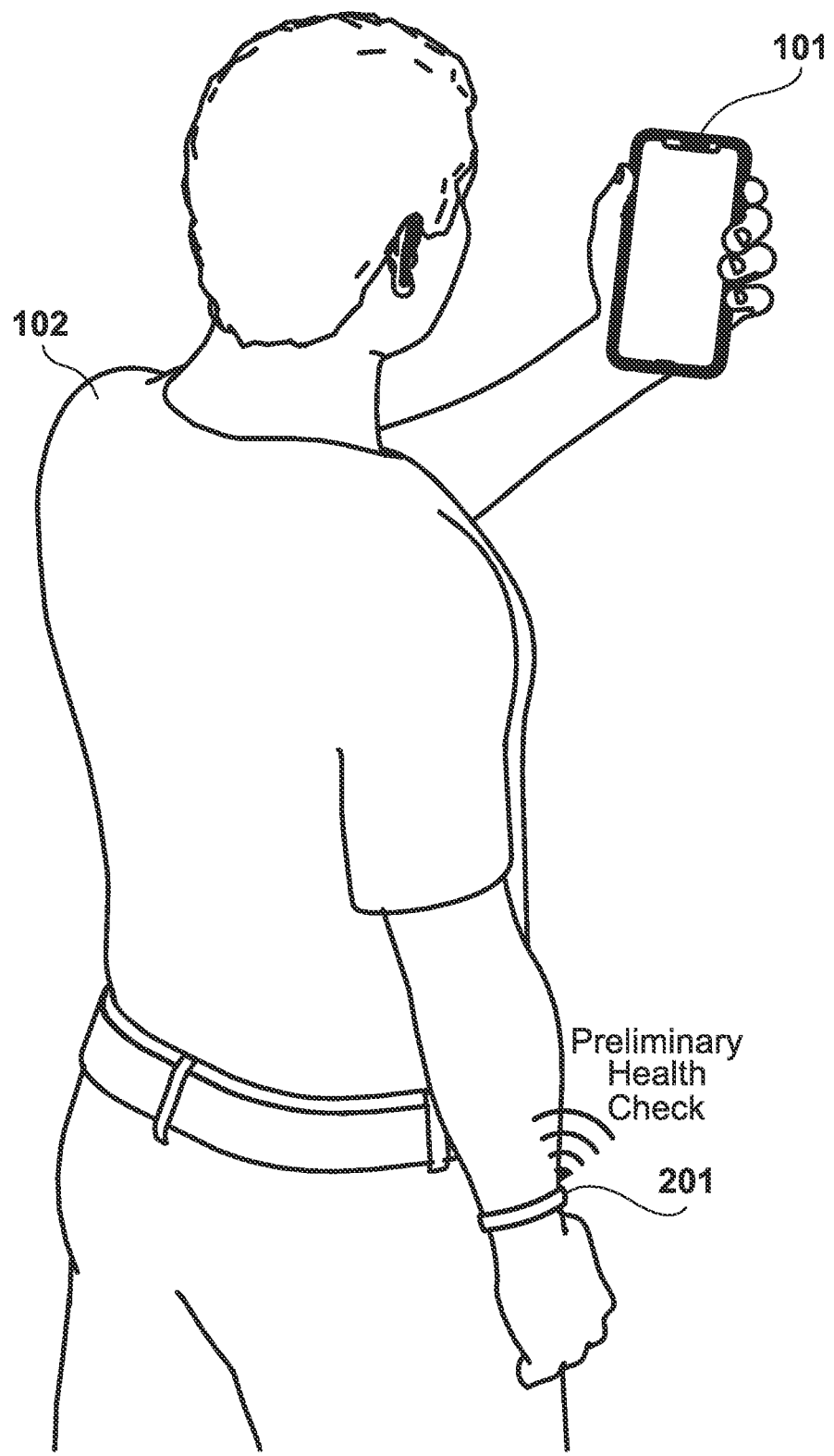
FIG. 2A illustrates an example of the user using the mobile computing device in conjunction with a smart bracelet.
Figure 2B:
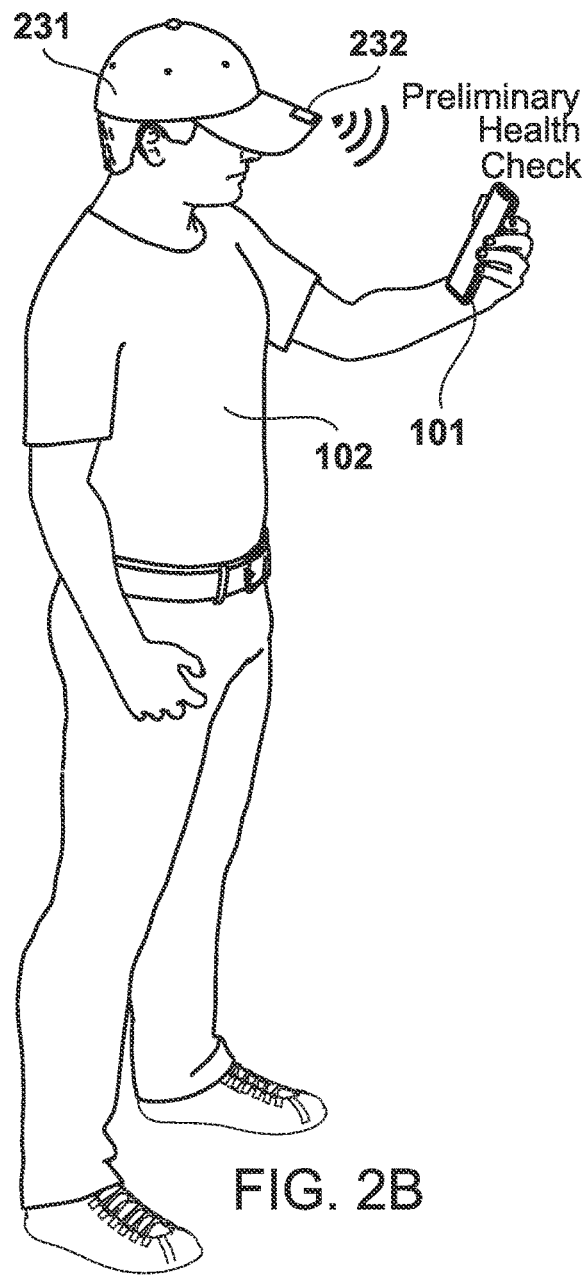
FIG. 2B illustrates a smart wearable device in the form of a smart hat that measures and emits the preliminary health check data.
Figure 2C:
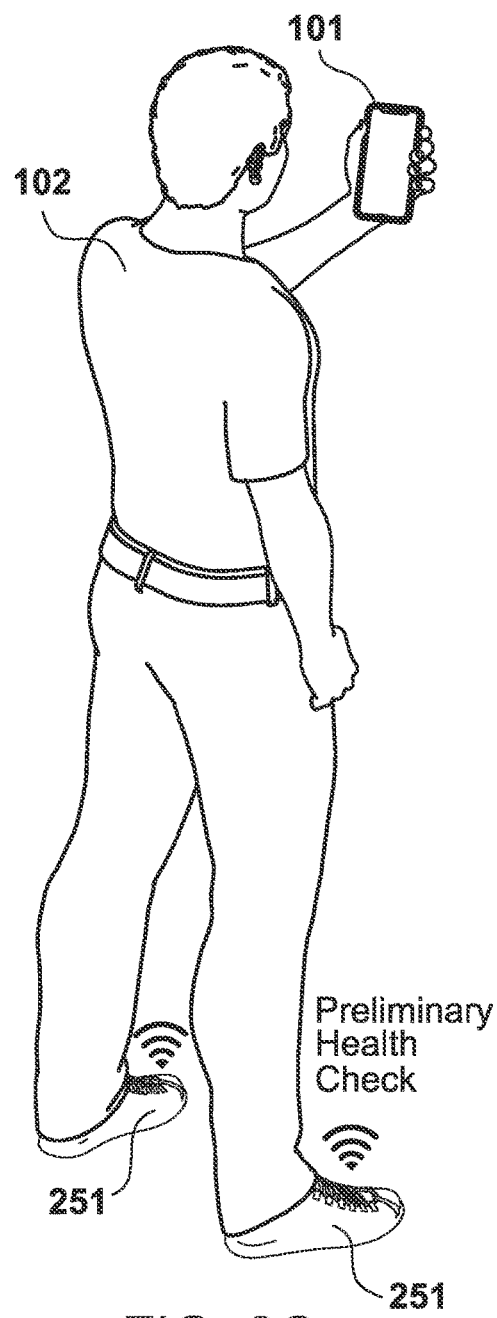
FIG. 2C illustrates a smart wearable device in the form of smart shoes, which may have a built-in thermometer that measures the foot temperature of the user.

By way of contrast, the mobile computing device 101 illustrated in FIGS. 2A-2C may wirelessly (e.g., via a BLUETOOTH link of biometric card interface stored within the mobile computing device 101) communicate with one or more accessory devices carried or worn by the user 102. In particular, FIG. 2A illustrates an example of the user 102 using the mobile computing device 101 in conjunction with a smart bracelet 201. In essence, the user 102 may provide the user identification data via one device (e.g., mobile computing device 101) and provide the preliminary health check data via another device (e.g., smart bracelet 201). Furthermore, the smart bracelet 201 may be configured to automatically emit the preliminary health check data to the product/service provider access device 114, illustrated in FIGS. 1A-1D, upon user validation via the biometric identification data received at the mobile computing device 101. Accordingly, the user 102 may not have to press any buttons on, or perform any other actions with respect to, the smart bracelet 201. In another embodiment, the smart bracelet 201 is configured to automatically emit the preliminary health check data based upon location data sensed by the smart bracelet 201 or the mobile computing device 101. For example, the smart bracelet 201 may be configured to emit a particular form of preliminary health check data (e.g., blood pressure) based upon detection, such as a via a global position system ("GPS") sensor, of the user 102 being geolocated at a pharmacy. (The GPS may be integrated in either, or both of, the smart bracelet 201 or the mobile computing device 101.)

The smart bracelet 201 is just an example of a smart wearable device that may be worn by the user 102 to determine the preliminary health check data. As another example, FIG. 2B illustrates a smart wearable device in the form of a smart hat 231 that measures and emits the preliminary health check data. For instance, the smart hat 231 may have a built-in thermometer that measures the forehead temperature of the user 102. A transmitter 232 situated on the brim of the cap, or integrated within the smart hat 231 in a manner that does not draw attention, may send the preliminary health check data to the mobile computing device 101. As yet another example, FIG. 2C illustrates a smart wearable device in the form of smart shoes 251, which may have a built-in thermometer that measures the foot temperature of the user 102.

Figure 3:
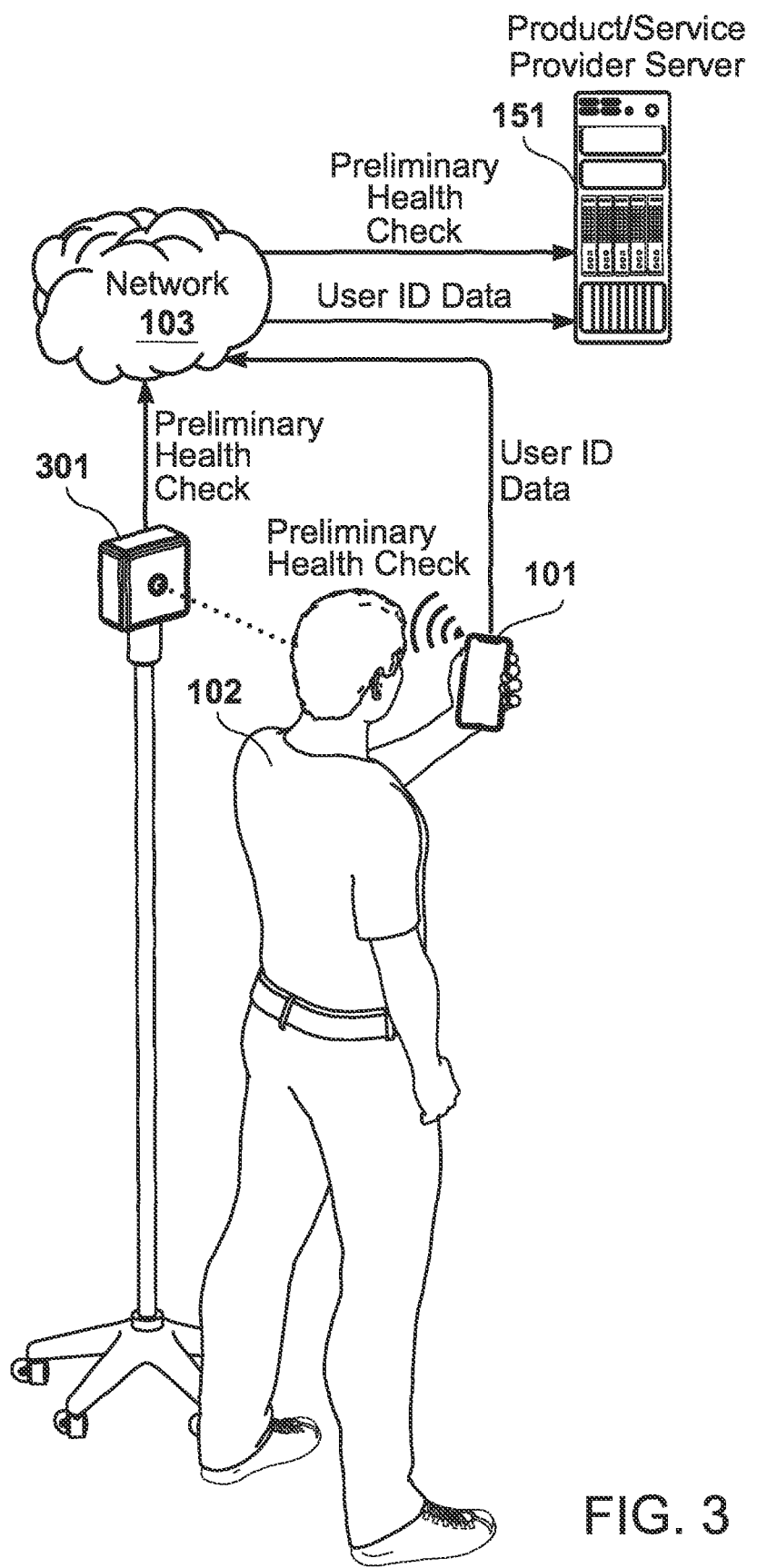
FIG. 3 illustrates a statically-positioned health measurement device that may measure the preliminary health check data of the user.

Furthermore, the preliminary health check data is not limited to being generated at the mobile computing device 101 or a smart wearable device worn by the user 102. For example, as illustrated in FIG. 3, a statically-positioned health measurement device 301 may be measure the preliminary health check data of the user 102. For instance, the statically-positioned health measurement device 301 may scan an eardrum or forehead of the user to determine if the user 102 has a fever. In one embodiment, the statically-positioned health measurement device 301 transmits the preliminary health check data, via the network 103, to the product/service provider server 151. Furthermore, the mobile computing device 101 may also transmit the user identification data, via the network 103, to the product/service provider server 151. In another embodiment, the statically-positioned health measurement device 301 may transmit the preliminary health check data to the mobile computing device 101, which may then send both, or either of, the biometric identification data and the biometric health check data to the product/service provider server 151. In yet another embodiment, the mobile computing device 101 may transmit the biometric identification data to the statically-positioned health measurement device 301, which may then send both, or either of, the biometric identification data and the biometric health check data to the product/service provider server 151.

The statically-positioned health measurement device 301 may be positioned unobtrusively so that it is not apparent to the user 102. For example, it may be integrated into a wall, turnstile, or other statically-positioned structure.

Figure 4:
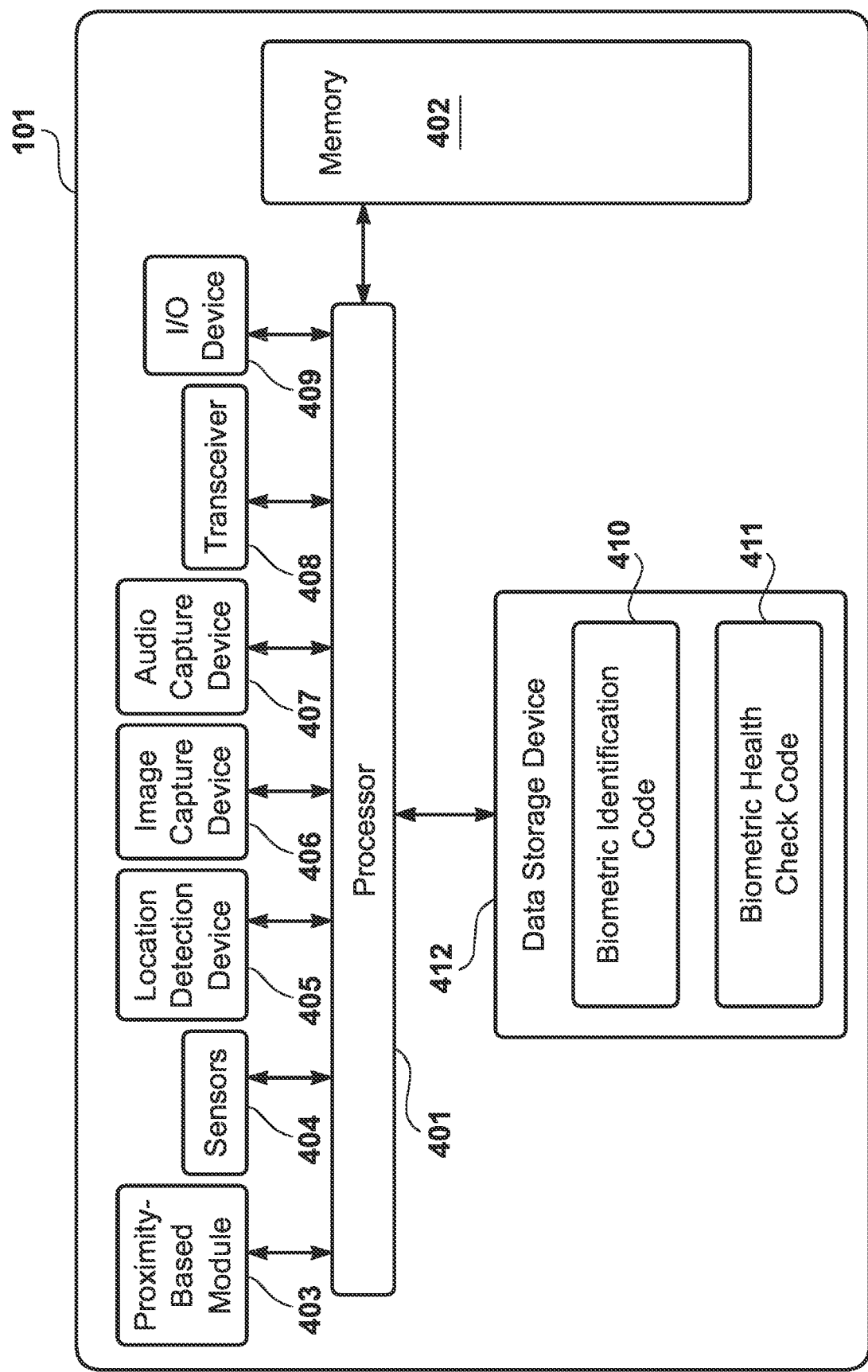
FIG. 4 illustrates a system configuration for the computing device, illustrated in FIGS. 1A-1D.

Moreover, FIG. 4 illustrates a system configuration for the mobile computing device 101, illustrated in FIGS. 1A-1D. A processor 401 may be specialized for biometric operations and GUI generation.

The system configuration may also include a memory device 402, which may temporarily store data structures used by the processor 401. As examples of such data structures, a data storage device 412 may store biometric identification code 410 and biometric health check code 411.

The processor 401 may execute the biometric identification code 410 and biometric health check code 411 to perform dual layers of biometric validation (i.e., identification and health check) to obtain access to a product or service for the user 102. Alternatively, one, or both, of the biometric identification code 410 and biometric health check code 411 may be executed by another device/system (e.g., server, wearable accessory device, etc.) in operable communication with the mobile computing device 101.

In one embodiment, the processor 401 is in operable communication with a proximity-based module 403, which is a physical circuit, such as an NFC physical circuit. Upon detecting the presence of an NFC-based reader within the product/service provider access device 114, the proximity-based module 403 awaits an indication of biometric validation from the processor 401, at which time the NFC-based circuit transitions from an open position to a closed position to transmit data (identification, health check, or both), via magnetic inductive communication, to the NFC-based reader within the product/service provider access device 114. In another embodiment, the proximity-based module 403 is a logical circuit that is implemented via software. Furthermore, the proximity-based module 403 may perform its functionality via two sub-modules, a proximity-based detection module and a proximity-based transmission module, or as one unified module. (The example of NFC is only one example, and is not intended to limit the applicability of the configurations provided for herein to the exclusion of other proximity-based technologies.)

Moreover, the mobile computing device 101 may have one or more sensors 404, image capture devices 406, and audio capture devices 407, specifically configured to sense health parameters pertaining to the user 102. For example, the sensors 404 may be IR sensors that sense body temperature. As another example, the image capture devices 406 may capture imagery of pupil dilation. As yet another example, the audio capture device 407 may capture audio of breathing patterns of the user 102. The processor 401 may then perform audio analysis to determine health symptoms, such as congestion, coughing, wheezing, etc.

Additionally, the mobile computing device 101 may have a location-based detection device 405, such as a GPS device. Based on the detection of various locations, the processor 401 may perform a lookup in a configuration table, stored in the memory 402, to determine an associated biometric identification modality (e.g., iris scan, fingerprint, thumb scan, palm scan, facial recognition, etc.) for that geographic location. For example, a pharmacy may necessitate biometric validation via an iris scan, whereas a firearm shop may necessitate biometric validation via a thumbprint. The configuration table may provide for an automatic determination by the processor 401 of the biometric modality that should correspond to the location detected by the location-based detection device 405.

Finally, the mobile computing device 101 may have one or more input/output ("I/O") devices 409, which may receive inputs and provide outputs, and a transceiver 408 to send and receive data. (Alternatively, a separate transmitter and receiver may be used instead.) Various devices (e.g., keyboard, microphone, mouse, pointing device, hand controller, joystick, etc.) may be used for the I/O devices 409.

Although the system configuration is described with respect to the mobile computing device 101, alternatively, it may be utilized in whole, or in part, by a server, such as the application server 104 or the product/service provider server 151 illustrated in FIGS. 1C and 1D, or a smart accessory to the mobile computing device 101, such as the smart bracelet 201, smart hat 231, or smart shoes 251 illustrated in FIGS. 2A-2C.

Figure 5A:
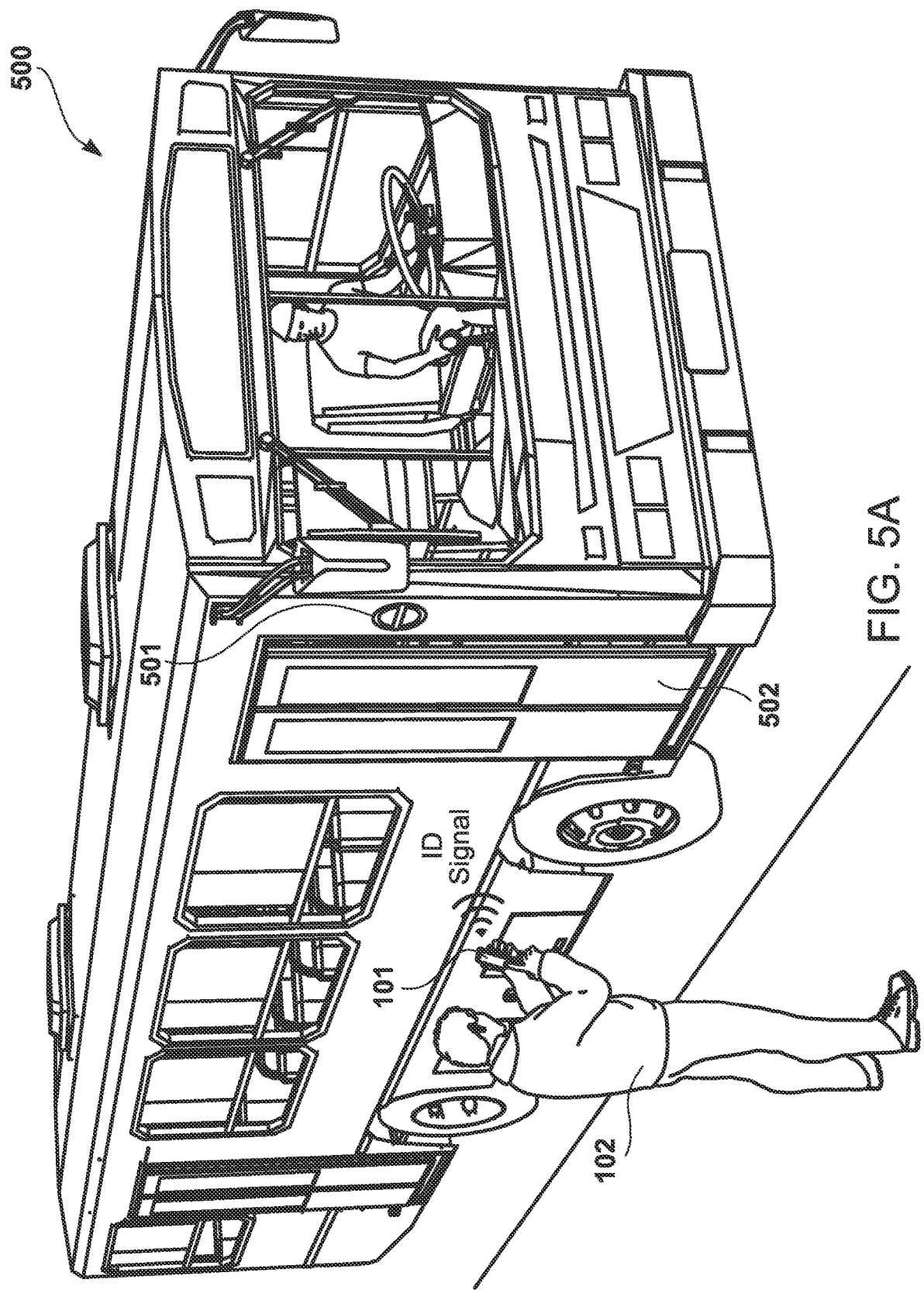
FIG. 5A illustrates a bus, which initially has restricted access, as indicated by an access indicium.
Figure 5B:
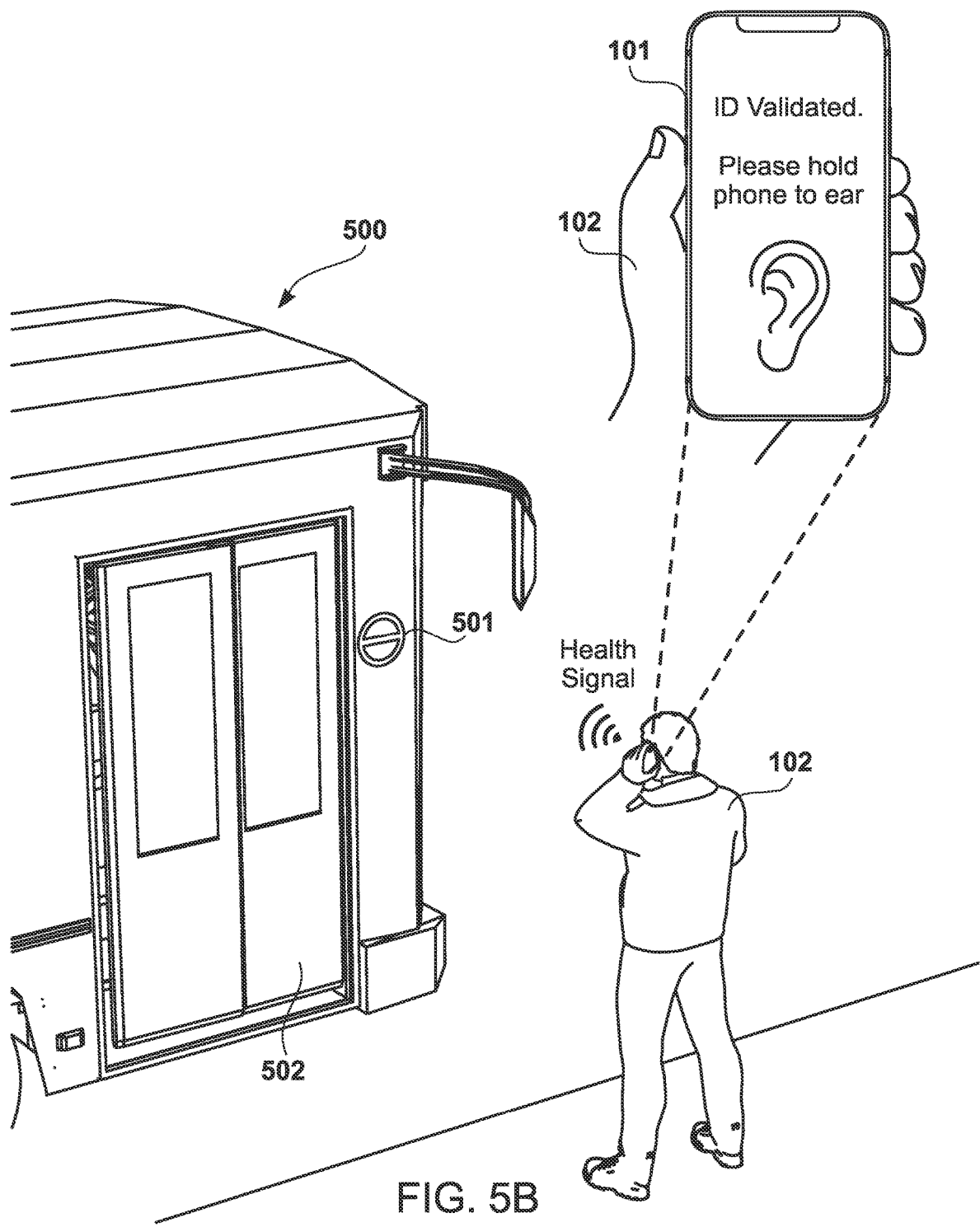
FIG. 5B illustrates the user holding the mobile computing device to his or her ear to perform a preliminary health check.
Figure 5C:
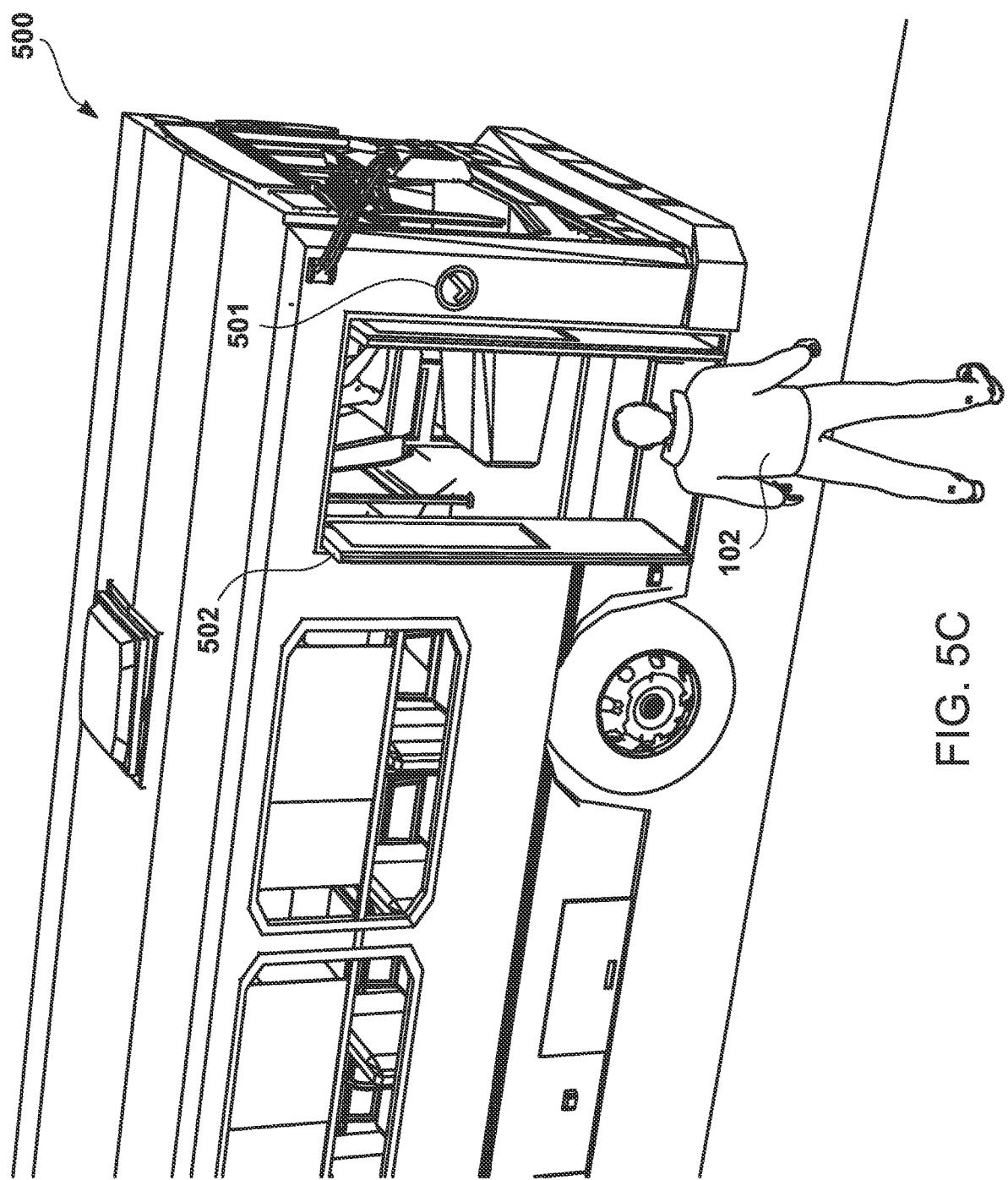
FIG. 5C illustrates the door of the bus automatically opening to grant access to the user upon compliance with the health criteria.

Irrespective of the particular dual-biometric configuration selected for implementation, a dual-biometric configuration is used to identify a user and determine health symptom compliance prior to granting access to the user 102 to products and/or services in a variety of contexts. FIGS. 5A-5C illustrate a particular example in the transportation context. In particular, FIG. 5A illustrates a bus 500, which initially has restricted access, as indicated by an access indicium 501 (e.g., image, sign, text, etc. indicative of access restriction). As the user 102 approaches the bus 500, the door 502 is closed, and remains closed until the user 102 provides dual biometric validation of his identity and health. Accordingly, as an example, the user 102 may provide his fingerprint on the mobile computing device 101. Upon validation, local or remote, of the identity of the user 102, the mobile computing device 101 may transmit the identity of the user 102 to a computing device positioned in the bus 500. Alternatively, the mobile computing device 101 performs the biometric validation without transmission of the identity of the user 102 to the computing device on the bus 500.

Furthermore, FIG. 5B illustrates the user holding the mobile computing device 101 to his ear to perform a preliminary health check. For example, the mobile computing device 101 may have an IR emitter, which emits IR light toward the eardrum of the user 102 while the user 102 is holding the phone close to his ear (similar to a hand position for speaking on the telephone). The mobile computing device 101 may also have an IR detector that detects, and measures the heat, of the IR light that reverberates from the eardrum of the user 102. Accordingly, the mobile computing device 101 is able to perform health measurements for a particular user prior to that user being granted access on the bus 500. Although the temperature of the user 102 is illustrated as being taken via an ear measurement, other forms of measurement (e.g., forehead) via other types of devices (e.g., smart accessory) may be performed instead.

In one embodiment, the particular types of health measurements performed by the mobile computing device 101 may be adjusted on-the-fly given a particular health occurrence within a given community. For example, within a given community at a particular time of year, health officials may declare an influenza pandemic. Accordingly, the application server 104, with which the mobile computing device 101 is in remote communication, or an access computing device, which may be positioned on the bus 500 for proximity-based wireless communication with the mobile computing device 101, may be configured to request specific health measurements, corresponding to symptoms for that particular strain of influenza, be performed by the mobile computing device 101. Yet, at another time of the year, the mobile computing device 101 may be configured to perform health measurements, via one or more sensors 404, commensurate with a less innocuous, but inconvenient, health concern such as the common cold. Therefore, the dual-biometric configuration of the mobile computing device 101 may perform dynamic adjustments to measure health symptoms, given a particular health concern.

Only upon compliance with the given health criteria at a given time does the door 502 of the bus 500 automatically open to grant access to the user 102, as illustrated in FIG. 5C. Furthermore, the access indicium 501 may change (e.g., imagery, color, text, etc.) to indicate that access onboard the bus 500 is permitted by the user 102. By measuring symptoms via the mobile computing device 101, communities may minimize the spread of viruses. For example, had the mobile computing device 101 measured a temperature for the user 102 indicative of a symptom of influenza, the user 102 would have been denied access to boarding the bus 500, thereby preventing the exponential spread of the influenza virus that could have easily occurred from just that one person boarding the bus 500.

With any of the dual-biometric configurations provided for herein, various orders of operations may or may not be applicable. In one embodiment, the dual-biometric configuration encompasses a biometric identity validation prior to performing a health check. In another embodiment, the health check may be performed prior to the biometric identity validation. In yet another embodiment, they may be performed simultaneously. In another embodiment, neither the biometric identification data nor the health check data is sent to the product/service provider access device 114, as illustrated in FIGS. 1A-1D, until both have been validated at the mobile computing device 101.

Figure 6A:
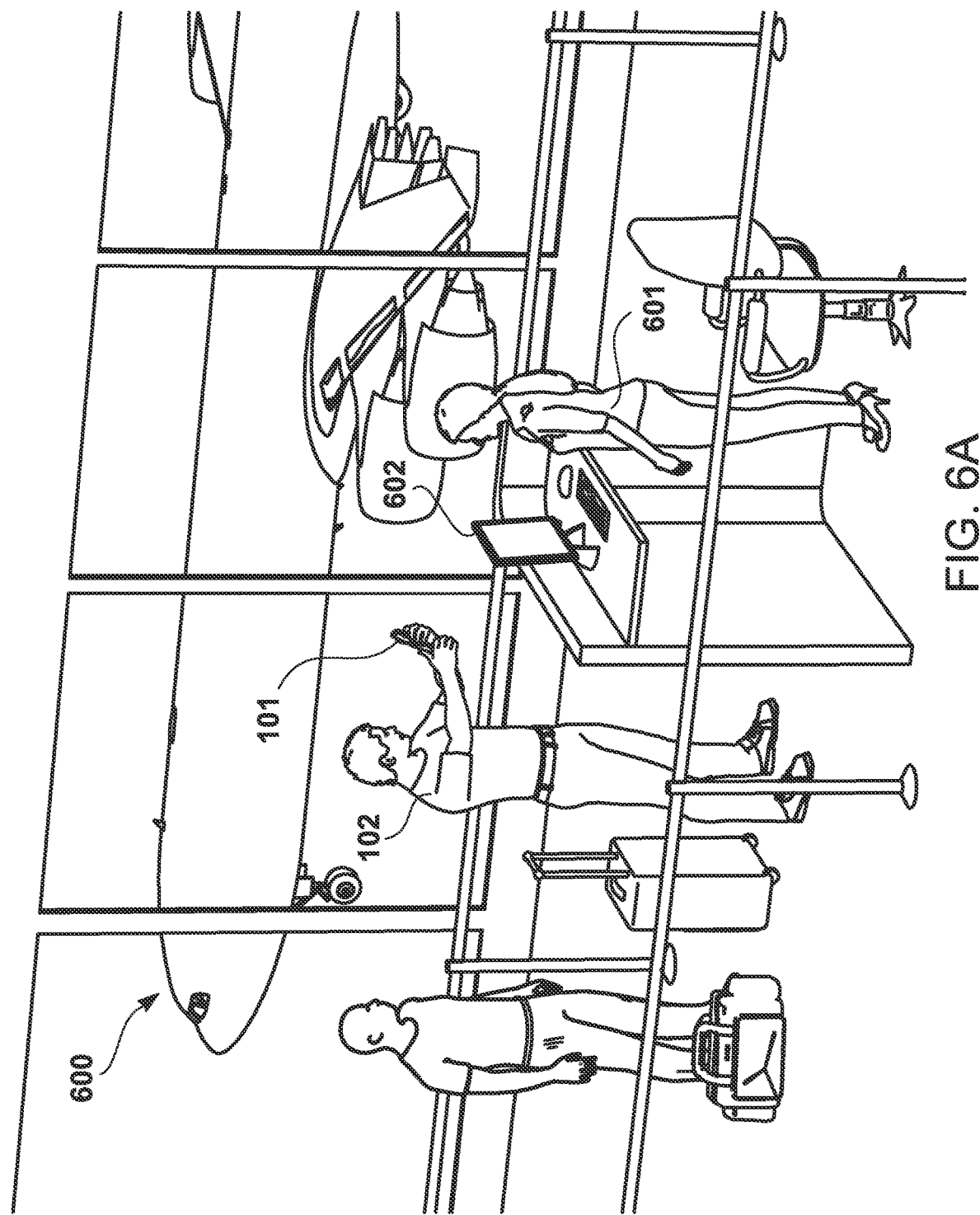
FIG. 6A illustrates an airline representative asking to view an e-ticket, as well as to perform biometric validation of the identity of the user.
Figure 6B:
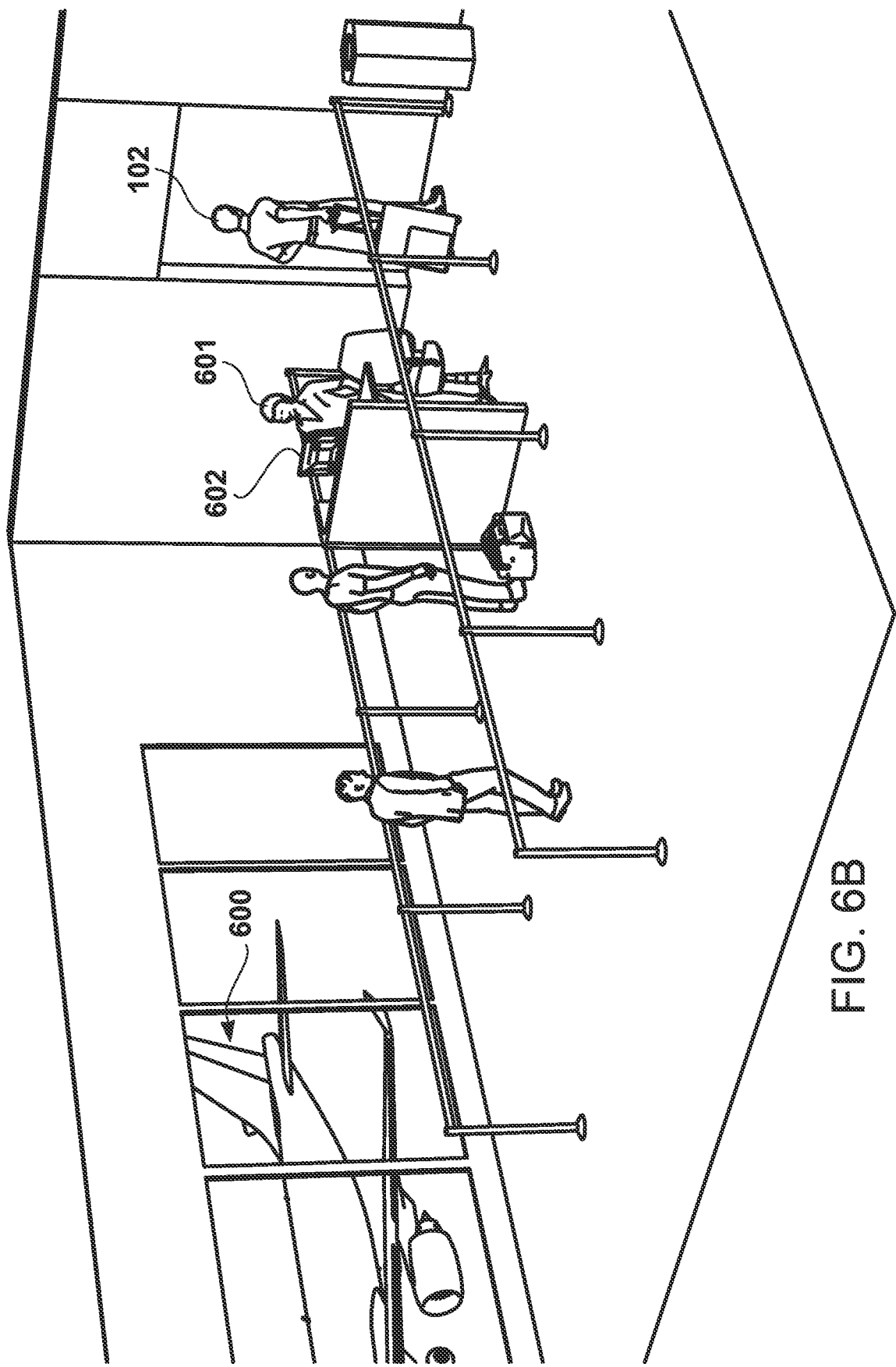
FIG. 6B illustrates the user 102 being cleared to board the airplane upon compliance with both the identification and health validation.

As another example of a dual-biometric configuration within the transportation context, the user 102 may utilize the mobile computing device 101 to board an airplane 600, as illustrated in FIGS. 6A and 6B. In particular, the user 102 may have an e-ticket stored on his mobile computing device 101. Prior to boarding the airplane 600, FIG. 6A illustrates the airline representative 601 asking to view the e-ticket, as well as to perform biometric validation of the identity of the user 102. In one embodiment, the computing device 602 of the airline representative 601 receives biometric identification data along with e-ticket information, allowing the airline representative 601 to automatically validate the identity of the user 102 upon the user providing a biometric input at the mobile computing device 101. Furthermore, the mobile computing device 101 of the user 102 may send health measurements to ensure compliance with health criteria, which may have been determined by the airline or a regulatory entity. Upon compliance with both the identification and health validation, the user 102 is cleared to board the airplane 600, as illustrated in FIG. 6B.

Figure 7A:
FIG. 7A illustrates the user validating his identity, via a biometric input at the mobile computing device.
Figure 7B:
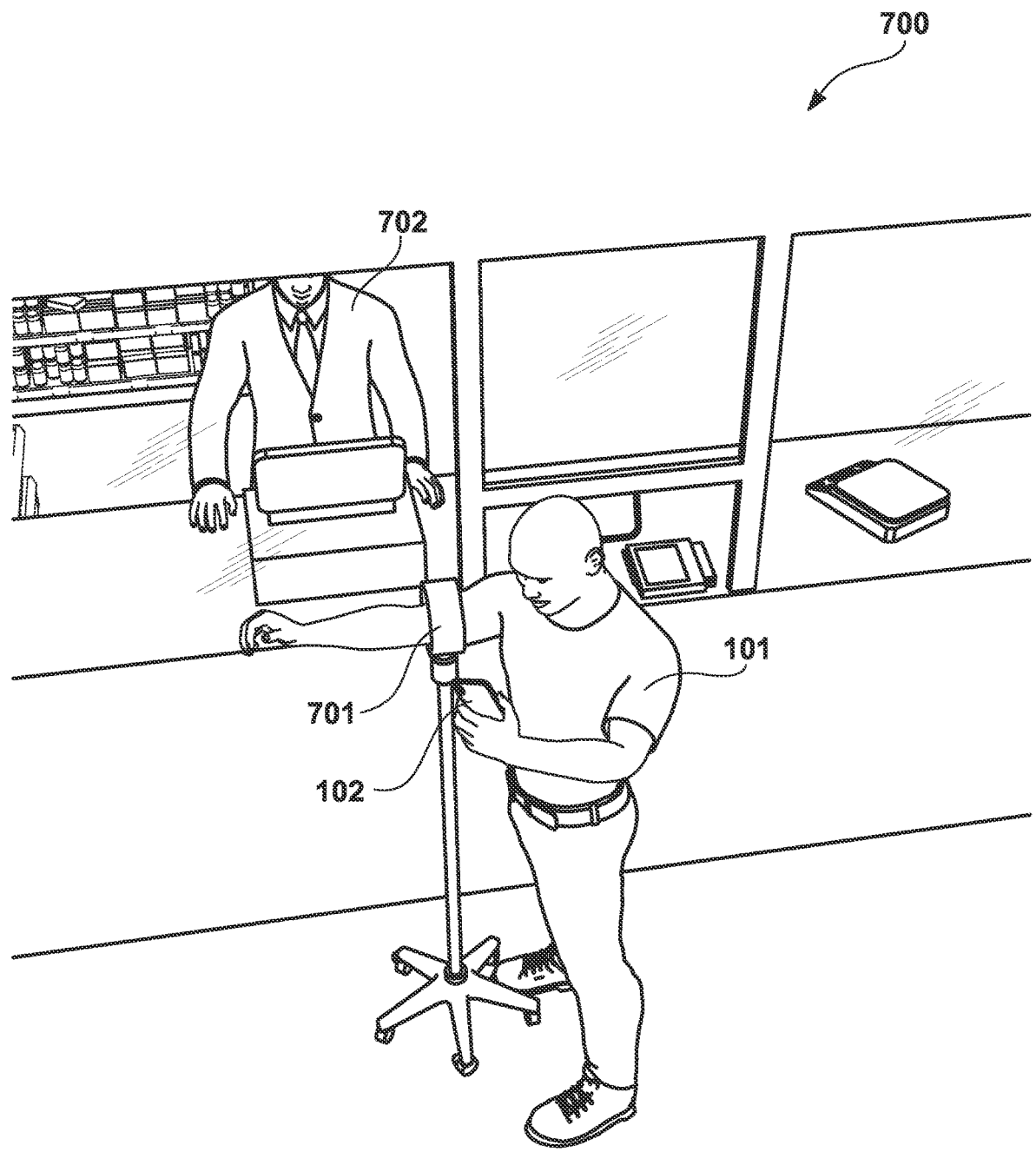
FIG. 7B illustrates the user using a statically-positioned blood pressure monitoring device to measure his blood pressure.
Figure 7C:
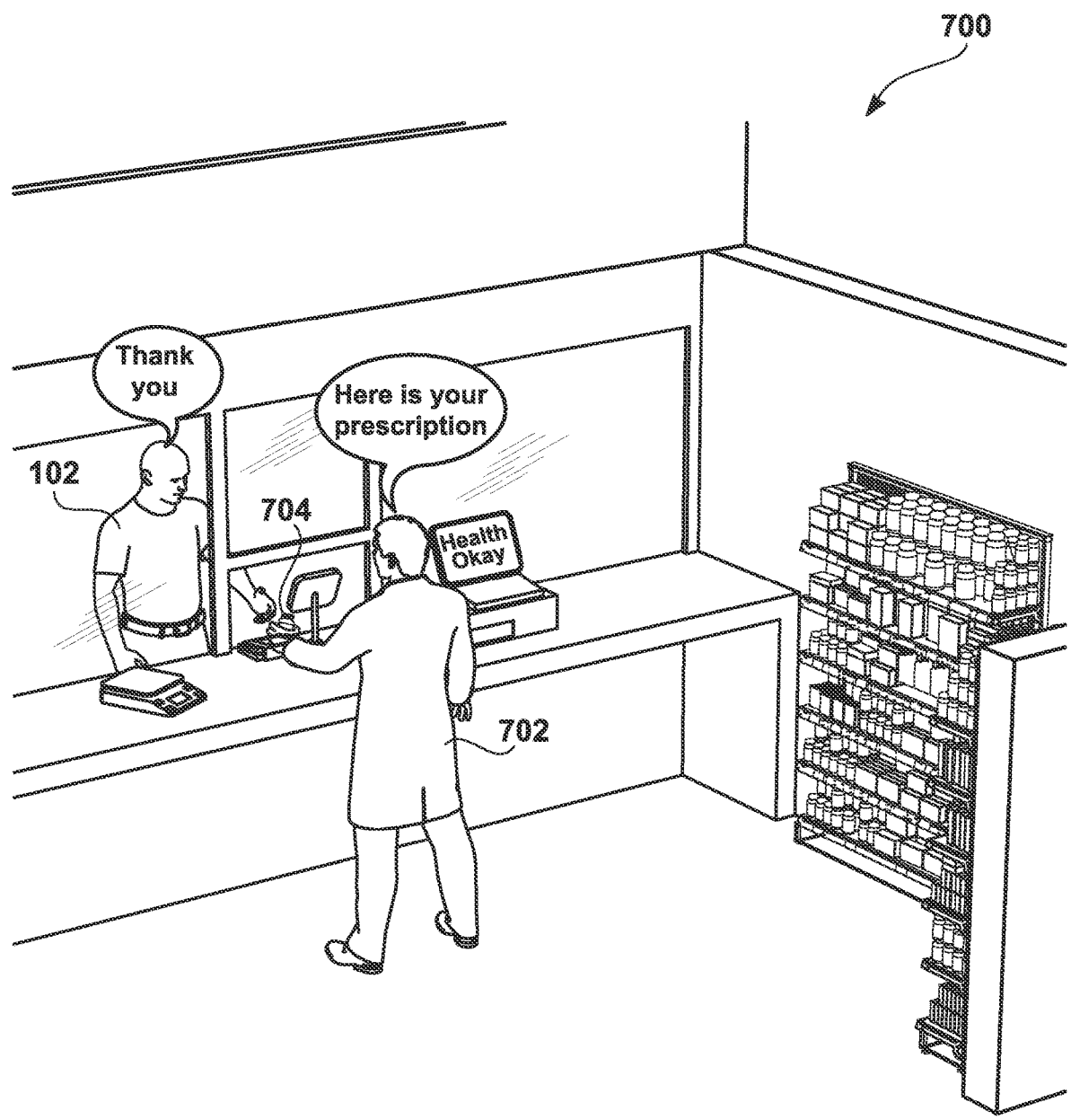
FIG. 7C illustrates a pharmacist providing the medication to the user upon the biometric validation criteria being met.

In addition to preventing the spread of viruses, the dual-biometric configurations provided for herein may be utilized to manage distribution of medications, especially those that are highly addictive. FIGS. 7A-7C illustrate a pharmacy 700 in which the user 102 requests pickup of his medication. In particular, FIG. 7A illustrates the user 102 validating his identity, via a biometric input (e.g., iris scan) at the mobile computing device 101. Furthermore, FIG. 7B illustrates the user 102 using a statically-positioned blood pressure monitoring device 701 to measure his blood pressure. (Other types of devices and measurements may be used instead.) Given that acceptable health measurements may be vary by an individual's particular biological traits (e.g., age, height, weight, etc.), the mobile computing device 101 may wirelessly receive the health measurement data to perform a comparison with the received data. For example, the mobile computing device 101 may store electronic medical records from the physician of the user 102. The electronic medical records may indicate acceptable ranges of health measurements for the user 102. Finally, as illustrated in FIG. 7C, the pharmacist 702 may provide the medication 704 to the user 102 upon the biometric validation criteria being met.

Figure 8A:
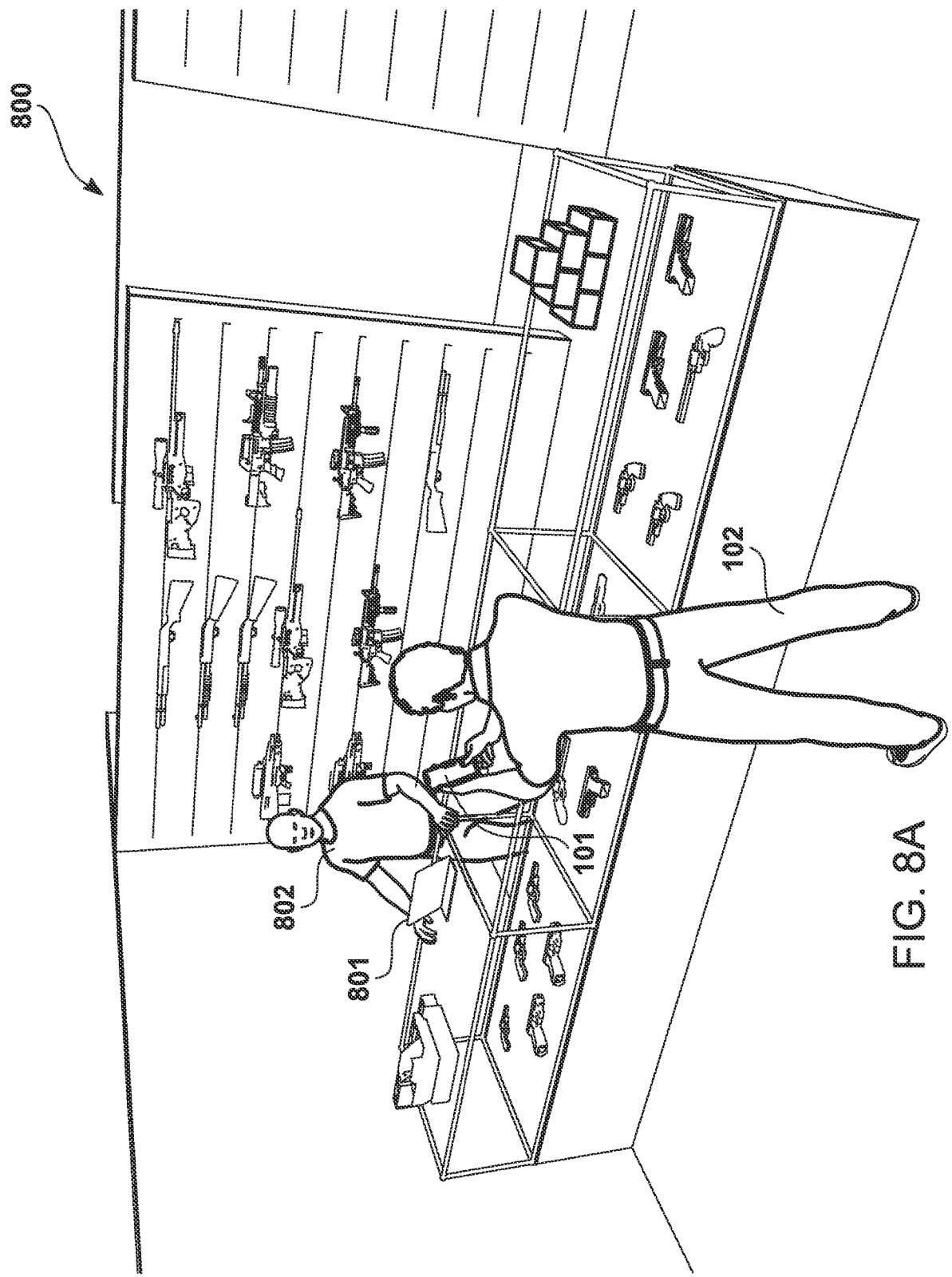
FIG. 8A illustrates the user entering the firearm distribution environment to purchase a firearm.

Moreover, the dual-biometric configurations provided for herein may be utilized in addition to background checks to manage the sale and distribution of controlled products, such as firearms. FIGS. 8A and 8B illustrate a firearm distribution environment 800 (e.g., gun shop, gun show, etc.) in which a firearm representative 802 may offer various firearms for sale. In particular, FIG. 8A illustrates the user 102 entering the firearm distribution environment 800 to purchase a firearm. Prior to purchasing the firearm, the user 102 may have to provide certain biometric identification information, such as a thumbprint. Accordingly, the user 102 may place his or her thumb on the touch screen of the mobile computing device 101 to provide a user input with the thumbprint of the user 102. The mobile computing device 101 may wirelessly communicate with a POS device 801 to provide the thumbprint of the user 102. As a result, the POS device 801 may perform a background check on the user 102. Furthermore, the mobile computing device 101 may send health biometric data as a result of that one thumb user input (e.g., pulse rate), and/or additional user inputs corresponding to other health biometric data, so that the POS device 801 may perform an additional assessment on the user 102. In other words, even if the user 102 successfully complies with the background check, the firearm distribution environment 800 may consider the health of the user 102 prior to completing the sale of the firearm to prevent potential firearm casualties. For instance, the physical symptoms of the user 102 may reflect the current mental state of the user 102, which may or may not be commensurate with a user that should be allowed to purchase a firearm. As illustrated in FIG. 8B, the POS device 801 may indicate that the identification and health validations were successful, thereby allowing the firearm representative 802 to proceed with the sale of the firearm to the user 102. In one embodiment, the firearm distribution environment 800 may have one or more electronic locks that prohibit access to the firearm, even by the firearm representative 802, until the biometric validations are successfully indicated by the POS device 801. Accordingly, the dual-biometric configurations provided for herein may be utilized for the process not only of selling a firearm, but also for showing a firearm to a customer that is potentially interested in a firearm purchase.

Figure 9A:
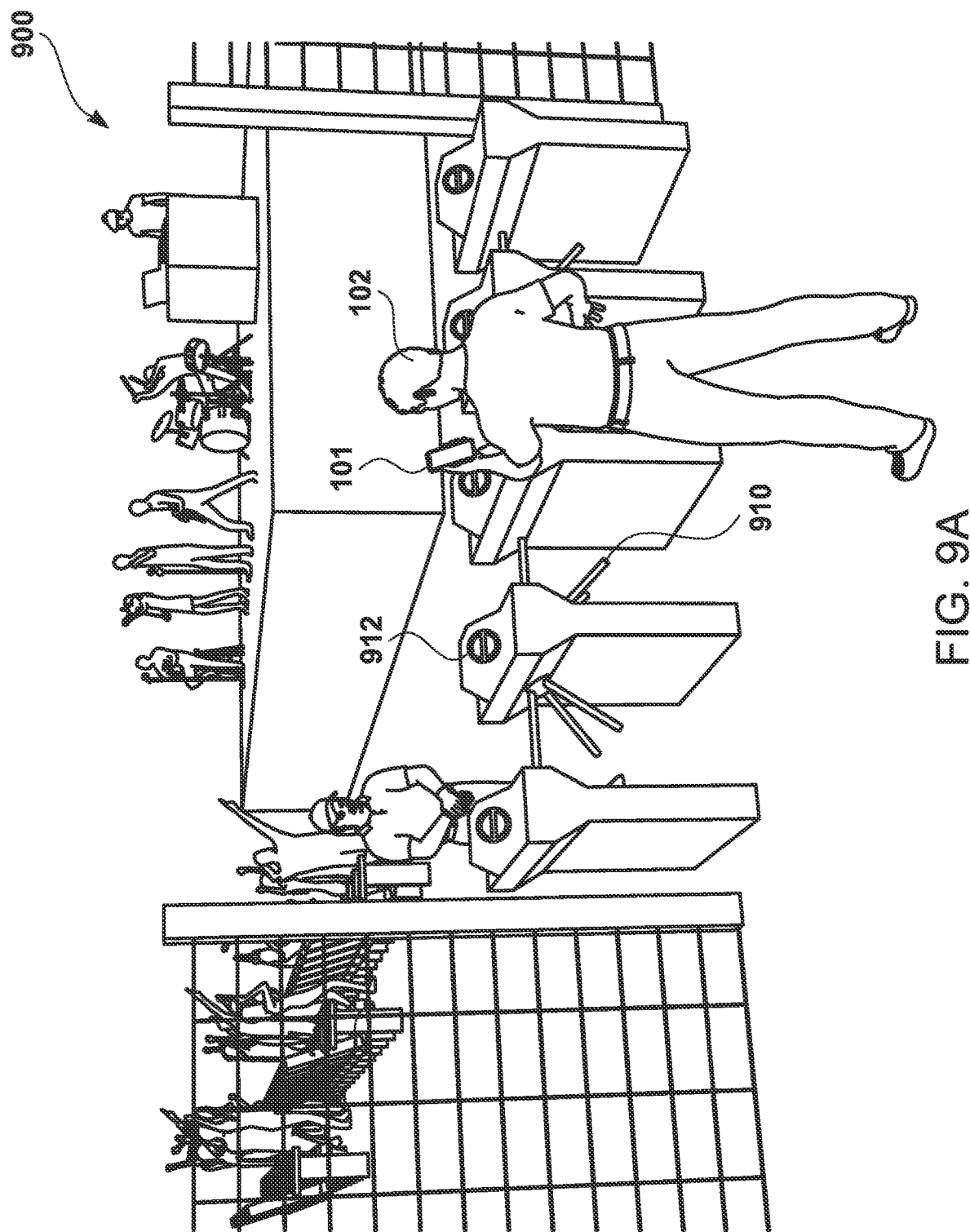
FIG. 9A illustrates the user approaching a turnstile to obtain access to a concert.
Figure 9B:
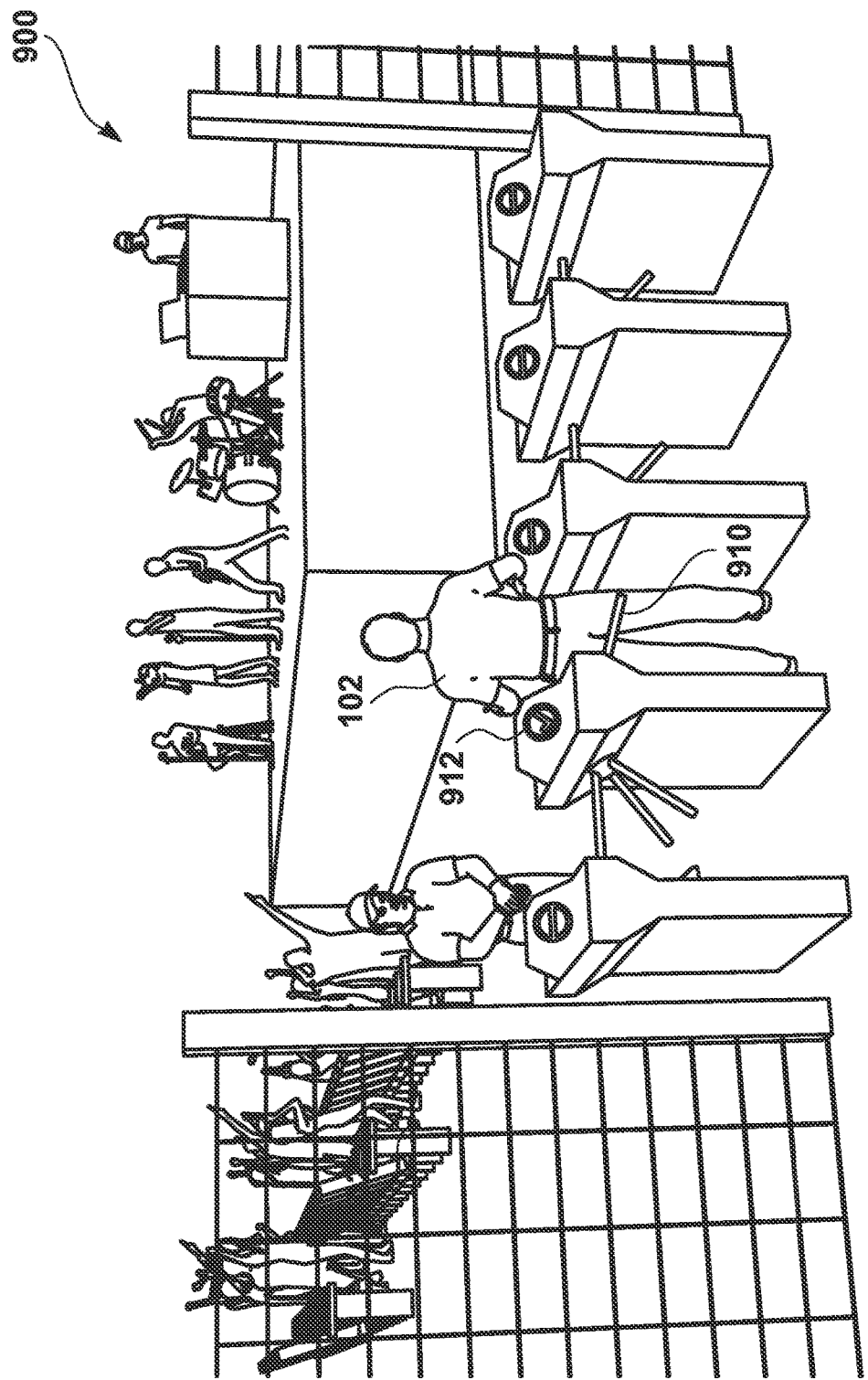
FIG. 9B illustrates the user successfully completing the biometric identification and biometric health check for automatic, permitted access through the turnstile.

The dual-biometric configurations are not limited to one-on-one interactions with other humans, but may also provide health risk minimization in crowded areas, such as the following: conventions, conferences, classrooms, concerts, sporting events, workplace meetings, hotels, rental properties, condominiums, etc. As an example, FIGS. 9A and 9B illustrate the dual-biometric configuration being implemented in a concert environment 900. In particular, FIG. 9A illustrates the user 102 approaching a turnstile to obtain access to a concert. In one embodiment, the user 102 may wirelessly provide identification information (e.g., e-ticket) to an access system built into the turnstile 910 (e.g., via NFC, barcode, QR code, etc.). Prior to providing such identification information, the user 102 may have to perform biometric validation (e.g., thumbprint, fingerprint, etc.). Furthermore, the user 102 may have to provide health data (via the user mobile computing device 101, an accessory device, or a stationary device positioned at the concert) to obtain access via the turnstile 910. In one embodiment, an access indicium (e.g., image, sign, etc.) is positioned on, or in proximity to, the turnstile 910 to indicate whether the user 102 is allowed access through the turnstile 910 to the concert. As illustrated in FIG. 9B, the user 102 has successfully completed the biometric identification and biometric health check, and, therefore, is automatically permitted access through the turnstile 910, as indicated by a change in the access indicium 912.

The automated restricted access system illustrated in FIGS. 9A and 9B not only minimizes the risk of viruses to other human beings in the concert, but also eliminates the possibility of staff potentially getting the virus. In other words, the automated restricted access system may be implemented without human beings monitoring tickets and health of individuals at the concert.

Figure 10A:
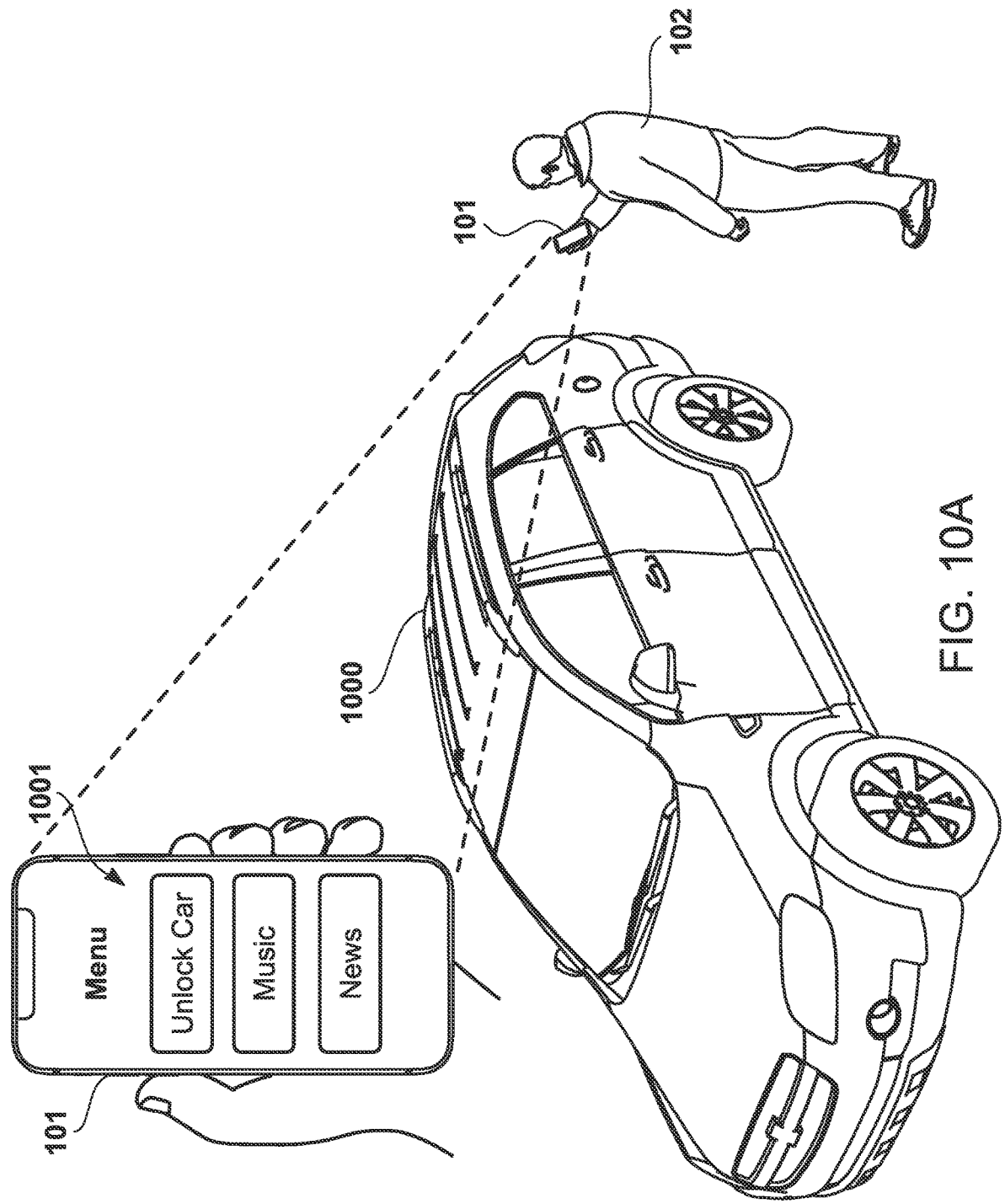
FIG. 10A illustrates the user utilizing a graphical user interface ("GUI") on the mobile computing device to access a menu to unlock the automobile.
Figure 10B:
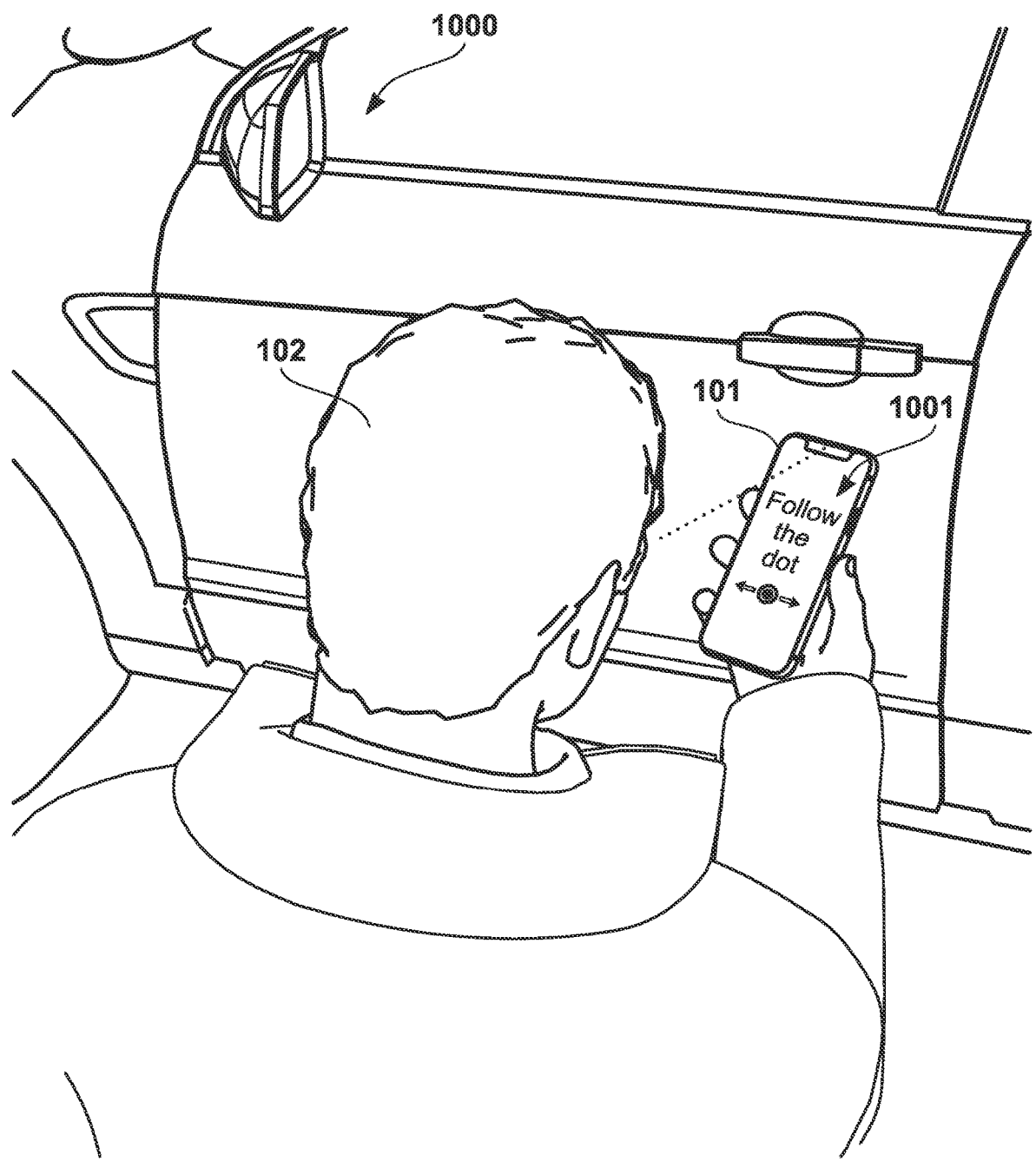
FIG. 10B illustrates the mobile computing device being configured to render a visual game, which tests the reflexes of the user, as a biometric health check.
Figure 10C:
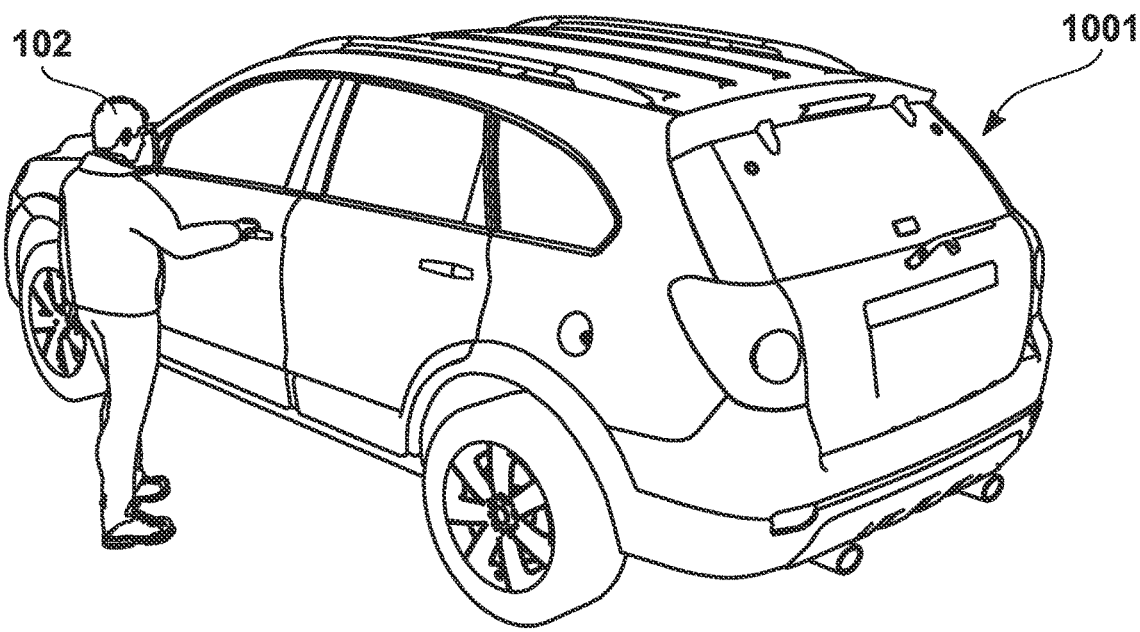
FIG. 10C illustrates the user attempting to open a door of the automobile, after successful biometric identification and health check validation.
Figure 10D:
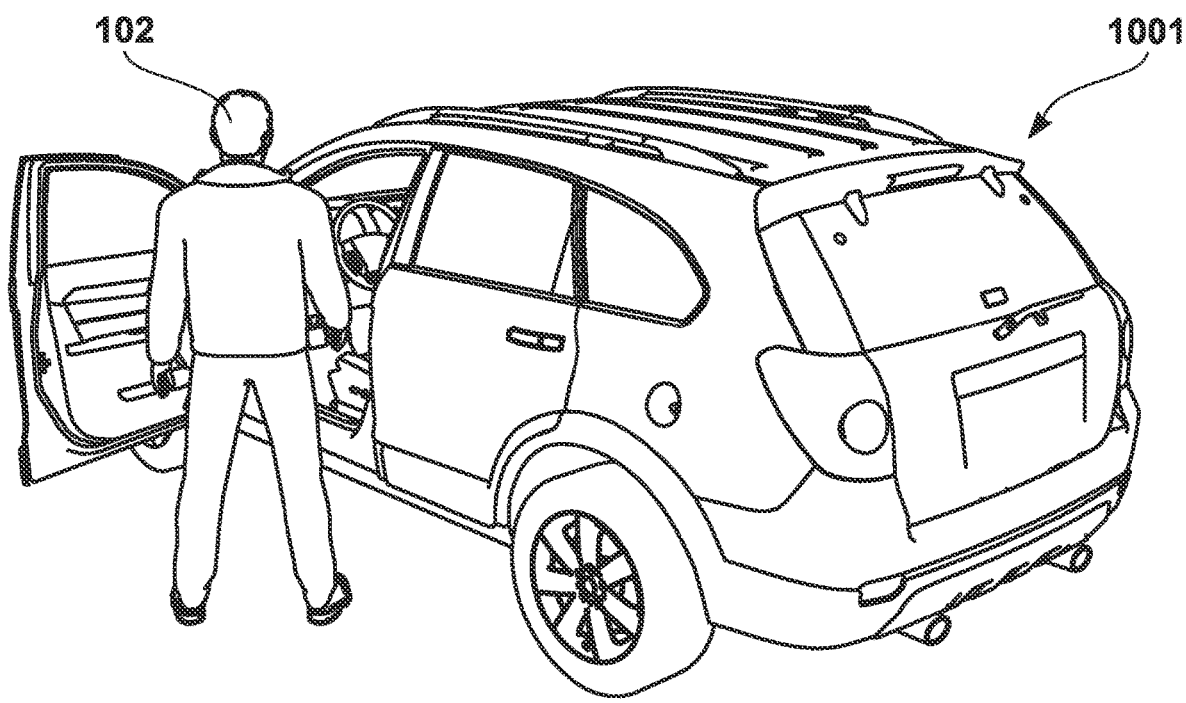
FIG. 10D illustrates the user successfully opening the door of the automobile.

Furthermore, the dual-biometric configurations provided for herein may be utilized to restrict access to an automobile 1000, as illustrated in FIGS. 10A-10C. Whether the automobile belongs to the user 102, or is temporarily leased to the user 102, the dual-biometric configuration prevents the user 102 from accessing the automobile 1000 unless he or she meets one or more health criteria. In particular, FIG. 10A illustrates the user 102 utilizing a GUI 1001 on the mobile computing device 101 to access a menu to unlock the automobile 1000. Initially, the user 102 may provide a biometric input that identifies the user 102 as the owner or lessee of the automobile 1000. In an alternative embodiment, the user 102 may have a key that allows the user 102 to access the automobile 1000 without a biometric identification, but the user 102 would still have to comply with a biometric health check. As an example of the biometric health check, as illustrated in FIG. 10B, the mobile computing device 101 may be configured to render a visual game, which tests the reflexes of the user 102. For example, the user 102 may have to move his or her eyes back and forth in various directions. An image capture device 406, illustrated in FIG. 4, of the mobile computing device 101 may then capture the eye movements of the user 102 to detect alertness of the user 102. By detecting such alertness, the mobile computing device 101 may prevent the user 102 from operating the automobile 1000 if the user 102 is intoxicated, sick, or not physically prepared in some other manner for operating the automobile 1000 at that given moment. FIG. 10C illustrates the user 102 attempting to open a door of the automobile 1000, after successful biometric identification and health check validation. Finally, FIG. 10D illustrates the user 102 successfully opening the door of the automobile 1000.

In another embodiment, the user 102 is permitted access to the automobile 1000 (e.g., to provide protection from inclement weather), but is not able to operate it (e.g., the ignition is prevented from being started) until successful biometric identification and health check compliance have been completed.

Figure 11A:
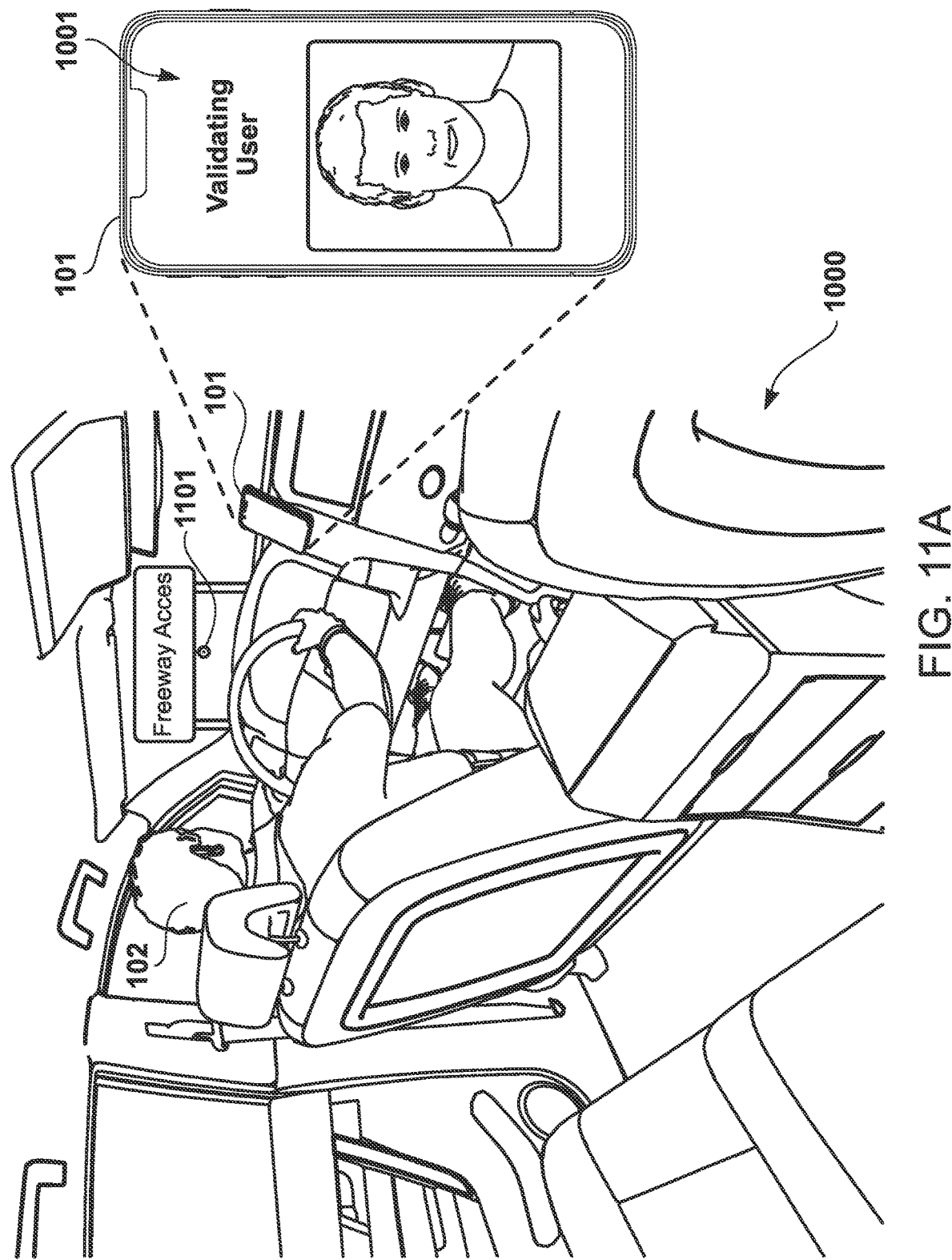
FIG. 11A illustrates the user in the automobile driving toward a freeway access point.
Figure 11B:
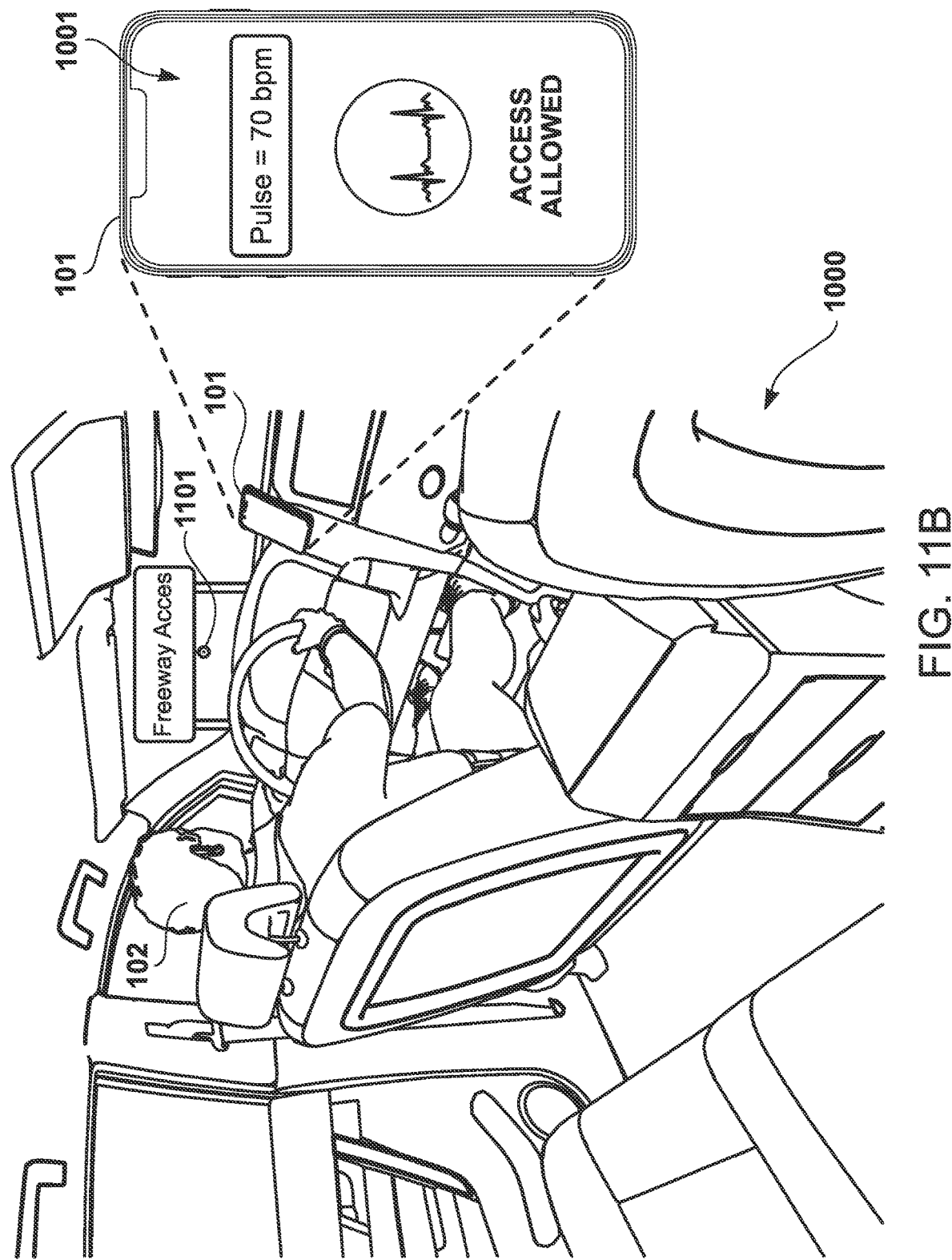
FIG. 11B illustrates a biometric health check of the user being performed to ensure that the user is in a condition to drive the automobile.

Furthermore, even after accessing an automobile, the user 102 may potentially develop symptoms that are not conducive to normal driving habits. Accordingly, as illustrated in FIGS. 11A and 11B, the dual-biometric configurations provided for herein may be utilized to restrict access by the user 102 to various transportation infrastructure, such as roads, bridges, bridges, and tunnels. For instance, FIG. 11A illustrates the user 102 in the automobile 1000 driving toward a freeway access point. Furthermore, the mobile computing device 101 may be configured (e.g., via a transponder) to communicate with an access point device 1101 via wireless transmission to indicate the identity of the user 102 and/or automobile 1000 for the purpose of obtaining freeway access. To ensure that the user 102 is actually the user 102, not a person that unscrupulously stole the mobile computing device 101, the mobile computing device 101 may perform a biometric identification validation of the user 102. For example, to avoid distracting the user 102 while driving, the mobile computing device 101 may be configured to automatically capture imagery of the user 102 to perform facial recognition without a manual input from the user 102, upon being within a predetermined proximity to the access point device 1101. For example, the access point device 1101 may send a signal to the mobile computing device 101 requesting the mobile computing device 101 perform the facial recognition of the user 102. Furthermore, as illustrated in FIG. 11B, a biometric health check of the user 102 may be performed to ensure that the user 102 is in a condition to drive the automobile 1000. For example, the user 102 may wear the smart bracelet 201, illustrated in FIG. 2A, to detect the health parameters (e.g., pulse rate) of the user 102. Again, the smart bracelet 201 may be automatically configured to detect such data without a manual input from the user 102 to avoid distracting the user 102 while driving the automobile 1000. Additionally, the smart bracelet 201 may wirelessly communicate with the mobile computing device 101, which may then transmit the health check data to the access point device 1101 to obtain access to the freeway for the user 102. Alternatively, the mobile computing device 101 may perform the health check (e.g., image capture of pupil dilation). As yet another alternative, the access point device may be in operable communication with a stationary health measurement device, positioned at an infrastructure checkpoint, that performs the health measurement of the user 102, and automatically communicates the health check data to the access point device.

Figure 12A:
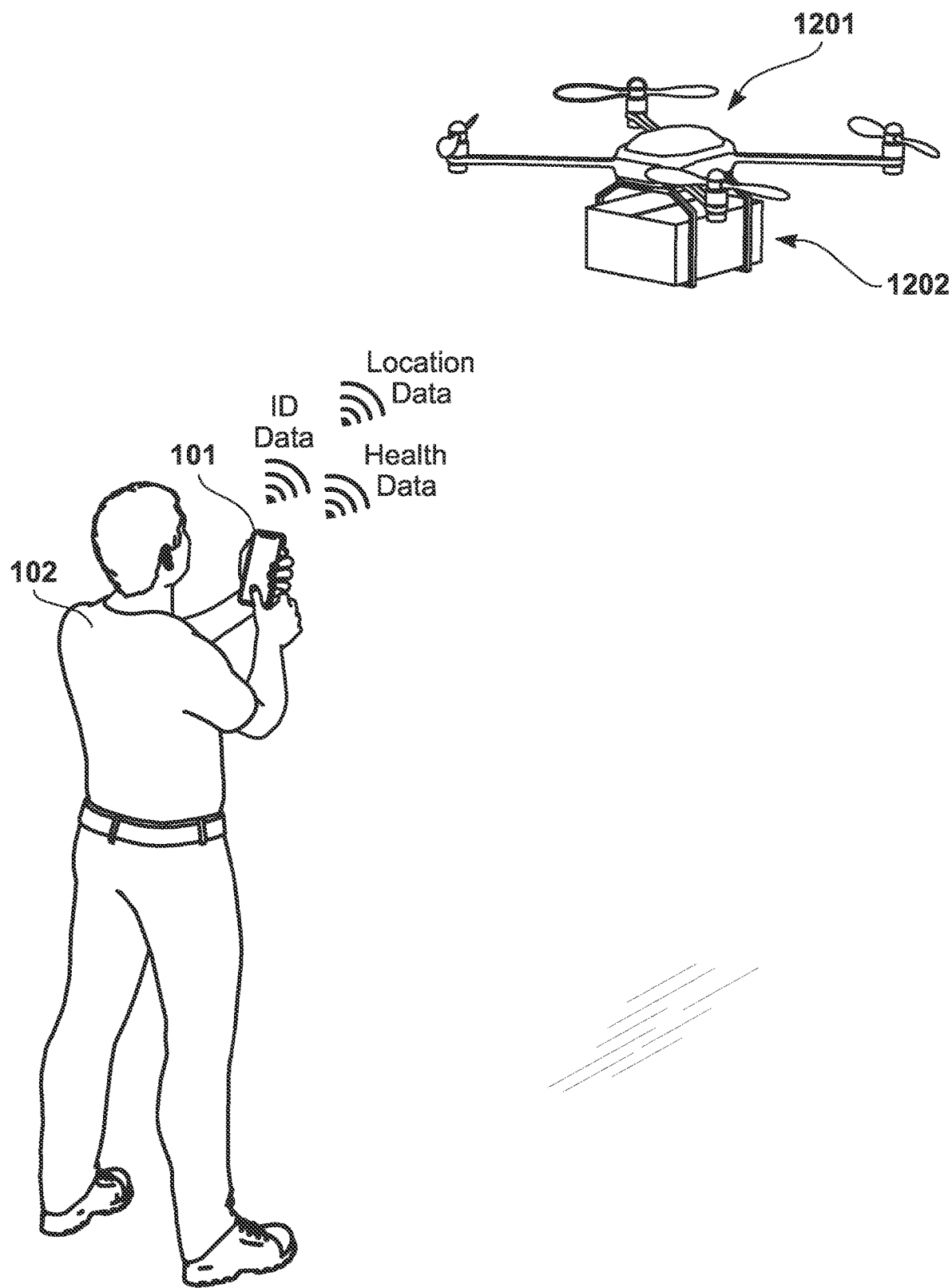
FIG. 12A illustrates the user utilizing the mobile computing device to emit location data, biometric identification data, and biometric health data to an unmanned aerial vehicle ("UAV").
Figure 12B:
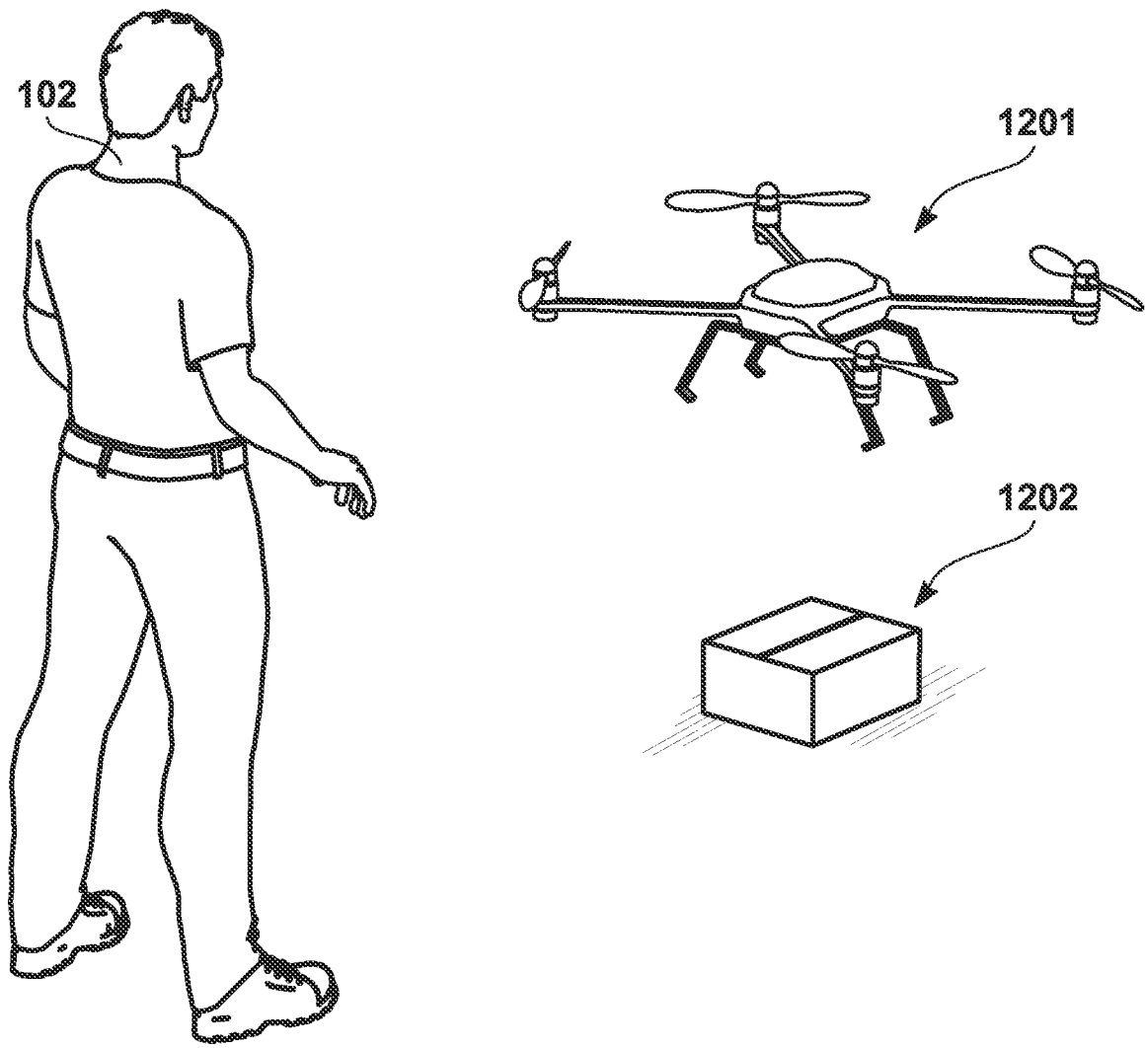
FIG. 12B illustrates the UAV delivering the package upon successful biometric identification and biometric health check validation.

To provide further convenience to the user 102, while minimizing human interaction, the dual-biometric configurations provided for herein may be utilized to interact with a UAV 1201 (e.g., drone) that delivers a package 1202 to a geographical location of the user 102, as illustrated in FIGS. 12A and 12B. In particular, FIG. 12A illustrates the user 102 utilizing the mobile computing device 101 to emit location data, biometric identification data, and biometric health data to the UAV 1201. Based on the location determined by an integrated location-based detection device 405, the mobile computing device 101 is able to provide the location to the UAV 1201 to which the UAV 1201 should bring the package 1202. Depending on the particular contents of the package 1202 (e.g., prescription medication), the UAV 1201 may necessitate biometric identification and a biometric health check of the user 102. In one embodiment, upon being within proximity to the mobile computing device 101, the UAV 1201 may transmit a message to the mobile computing device that prompts the mobile computing device 101 to request one or more biometric inputs from the user 102 via a software application. For example, the user 102 may provide a thumbprint that identifies the user 102 and performs a health check based on the pulse of the user 102. Upon successful biometric identification and biometric health check validation, the UAV 1201 may deliver the package 1202 to the user 102, as illustrated in FIG. 12B.

Figure 13A:
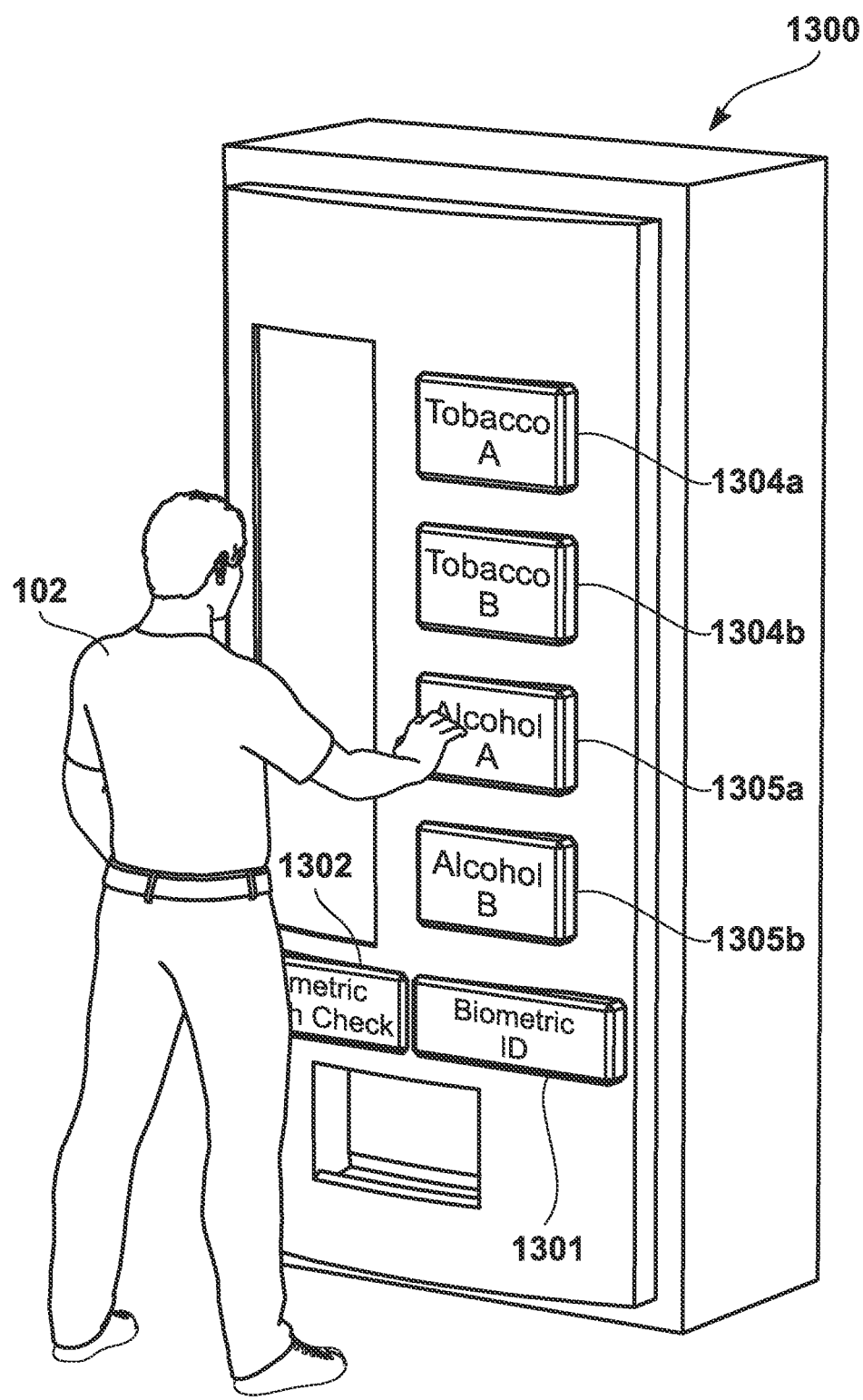
FIG. 13A illustrates the user approaching a vending machine to provide biometric identification.
Figure 13B:
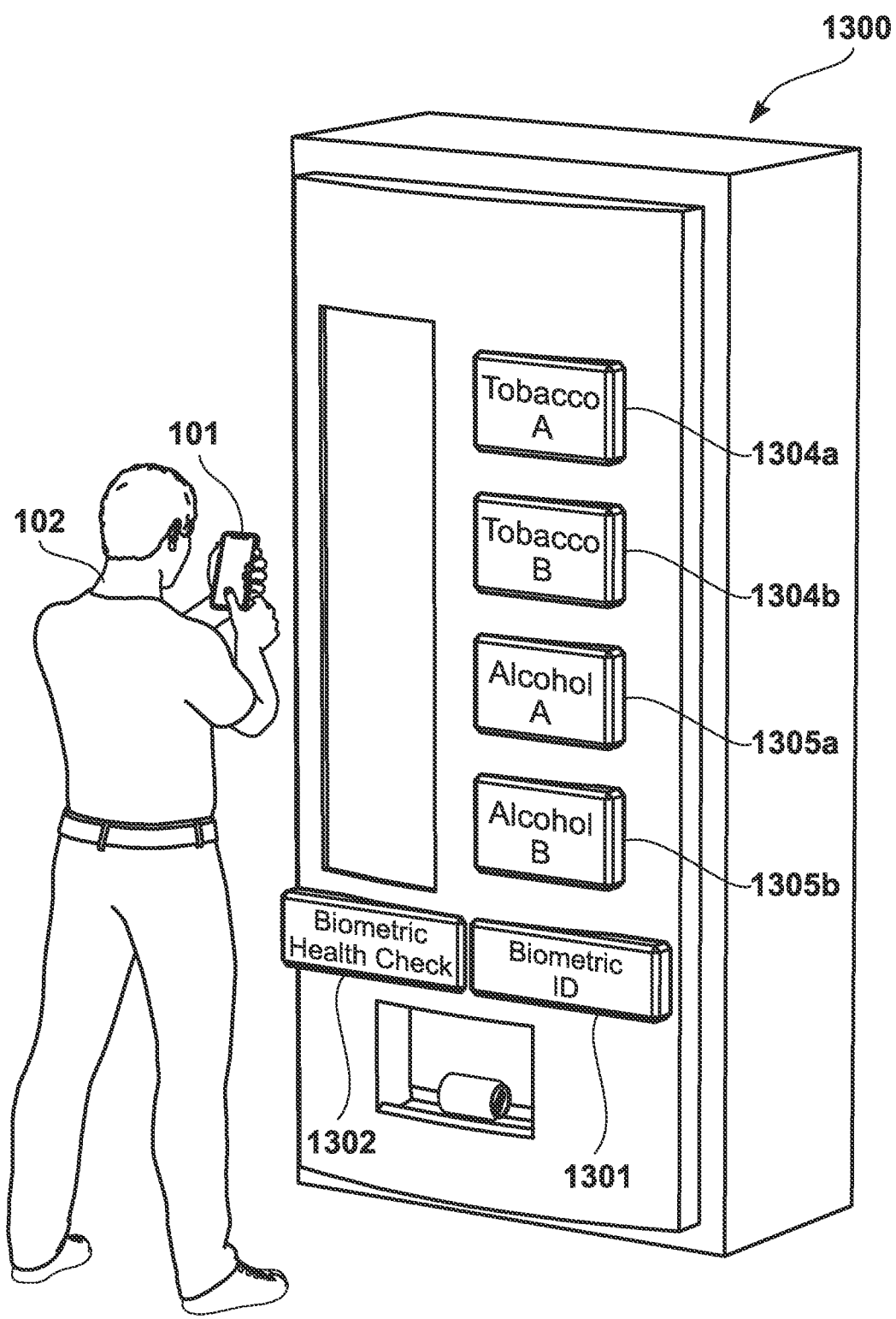
FIG. 13B illustrates the user obtaining his or her product from the vending machine upon compliance with the one or more health criteria.

As another example, FIGS. 13A and 13B illustrate a vending machine 1300 that may be utilized to automatically dispense items, such as controlled items, based upon biometric identification and biometric health check validation. For example, FIG. 13A illustrates the user 102 approaching the vending machine 1300 to provide biometric identification. The user 102 may select a controlled product (e.g., a tobacco product 1304a or 1304b, an alcohol product 1305a or 1305b, etc.), and then may press a biometric identification indicium 1301 (e.g., button) to initiate biometric identification. For example, the user 102 may have to meet a particular age requirement, which may be confirmed via a biometric input, such as a thumbprint, being compared by the vending machine 1300 with a biometric input database that is correlated to age. Alternatively, the user 102 may provide the biometric input to allow the mobile computing device 101 to provide an image of a valid form of identification (e.g., driver's license) to the vending machine 1300. Upon successful biometric identification, the user 102 may select a biometric health check indicium (e.g., button) 1302 on the vending machine 1300. Accordingly, the user 102 may then utilize the mobile computing device to determine one or more health parameters. Alternatively, the vending machine 1300 may have one or more health measurement devices that the user 102 may use to perform the biometric health check. Upon compliance with the one or more health criteria, the user 102 may obtain his or her product from the vending machine 1300, as illustrated in FIG. 13B.

Figure 14:
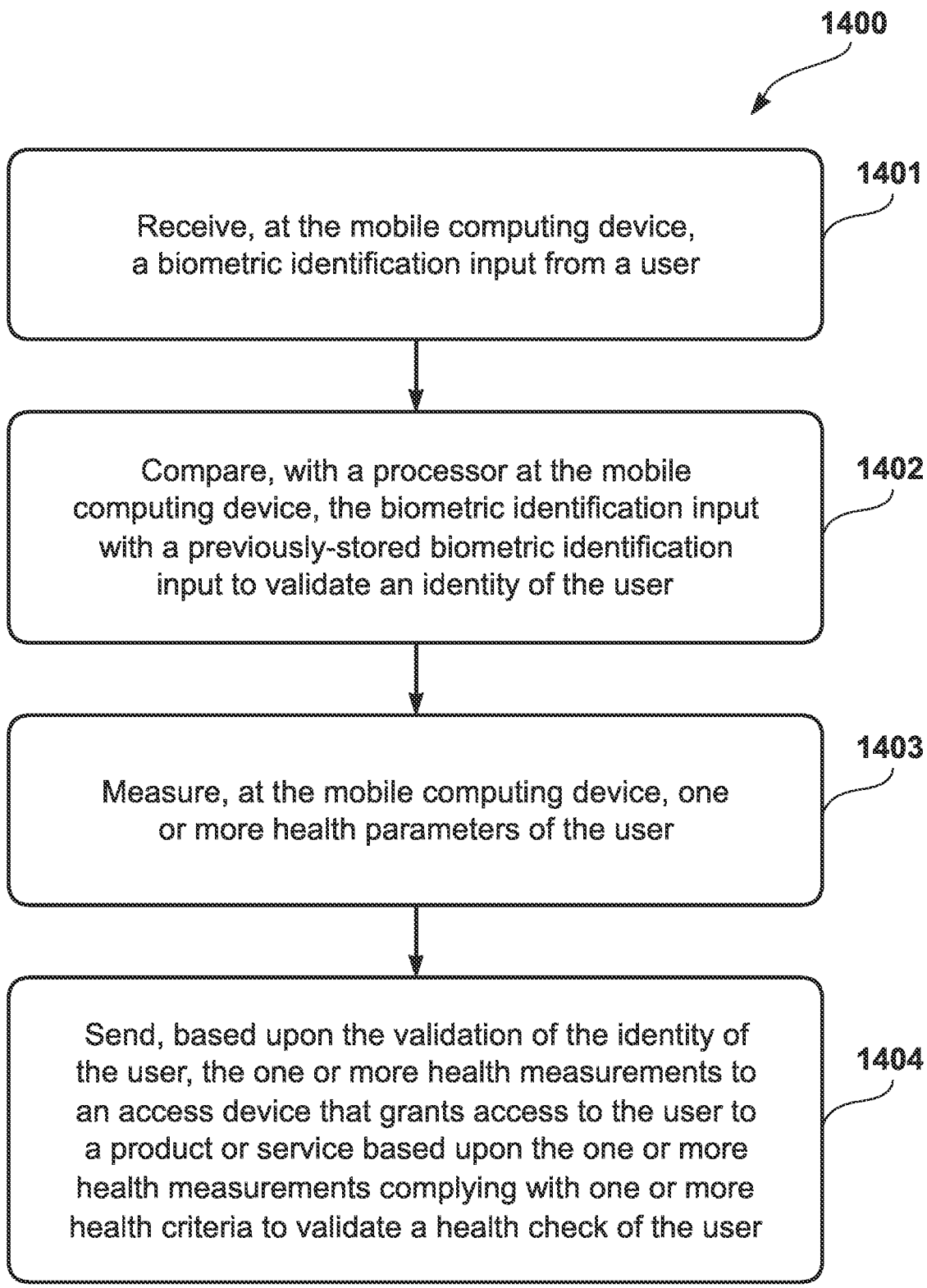
FIG. 14 illustrates a process that may be utilized to implement a dual-biometric configuration.

FIG. 14 illustrates a process 1400 that may be utilized to perform a dual-biometric configuration. At a process block 1401, the process 1400 receives, at the mobile computing device 101, a biometric identification input from a user 102. Furthermore, at a process block 1402, the process 1400 compares, with a processor 401 at the mobile computing device 101, the biometric identification input with a previously-stored biometric identification input to validate an identity of the user 102. Additionally, at a process block 1403, the process 1400 measures, at the mobile computing device 101, one or more health parameters of the user. Finally, at a process block 1404, the process 1400 sends, based upon the validation of the identity of the user 102, the one or more health measurements to an access device that grants access to the user 102 to a product or service based upon the one or more health measurements complying with one or more health criteria to validate a health check of the user 102.

In another embodiment, the process 1400 may be implemented to send the biometric identification input to a server, rather than perform the biometric validation via the mobile computing device.

In yet another embodiment, the process 1400 may be implemented such that the health measurements are provided to an entity without biometric identification data. Accordingly, the mobile computing device 101 may perform the biometric identification of the user 102, but the health measurements may be analyzed by a server independently of having biometric identification information of the user 102, thereby protecting the privacy of the user 102.

Furthermore, the dual-biometric configurations provided for herein are not limited to obtaining access to a product or service. Upon performing biometric identification and health check validation, the mobile computing device 101 of the user 102 may provide health check updates to one or more remotely situated devices, associated with person to whom such information is of interest (e.g., family member, friend, physician, work colleague, team member, etc.).

Figure 15:
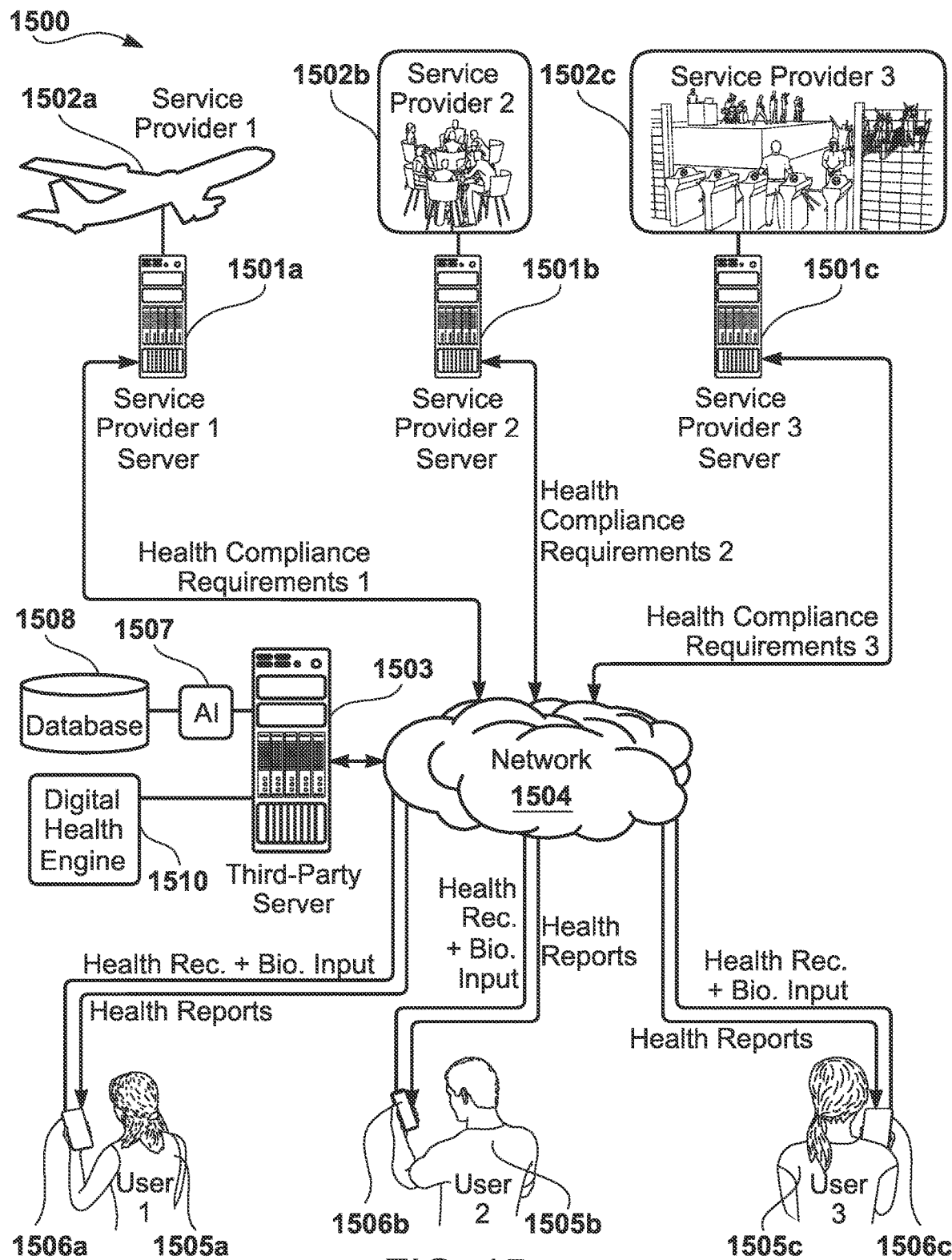
FIG. 15 illustrates a cloud-based digital health wallet platform that may be utilized as a third-party platform that is trusted both by users and service providers.

FIG. 15 illustrates a cloud-based digital health wallet platform 1500 (also referred to herein as a cloud-based third-party platform 1500) that may be utilized as a third-party platform that is trusted both by users 1505 and service providers 1502 to ingest (i) user health and identification data; and (ii) service provider healthcare requirements for access to a given service. In particular, third-party server computing device 1503 (also referred to herein as a third-party server or server computing device 1503) (multiple service computing devices may be utilized as opposed to a single server computing device) may communicate, via a computerized network 1504 (e.g., Internet, local area network ("LAN"), wide area network ("WAN"), peer-to-peer network, decentralized network, and/or the like), with various service provider computing devices 1501a-c (e.g., server computer, desktop computer, laptop computer, tablet device, smartphone, etc.) and various user computing devices 1506a-c (e.g., desktop computer, laptop computer, tablet device, smartphone, etc.) (also referred to herein as user mobile computing devices 1506). (Particular examples of a reference numeral are appended with an alphabetic character, such as "a-c"; such examples are not intended to limit the quantity of that which is being pointed to.) The service provider computing devices 1501a-c may provide data such as health and/or identification requirements for one of the users 1505a-c to access a particular service. As an example, a service provider 1502a may be an airline, which requires a valid boarding pass, a current driver's license, an up-to-date vaccine record for COVID-19, an up-to-date COVID-19 test, proof of health insurance encompassing COVID-19 benefits, and a current temperature reading of ninety-eight and sixth tenths degrees Fahrenheit, within a predetermined temperature threshold within two hours (other time periods may be utilized) prior to a departing flight. (An airline is just one example of a service provider 1502; other examples include restaurants 1502b, concert halls 1502c, and the like.) The foregoing health compliance requirements are sent by the service provider computing devices 1501a-c via the computerized network 1504 to the third-party server 1503, which may store this data in a database 1508 (acting as a health requirements database) for subsequent retrieval and/or machine learning. (The database 1508 may include a plurality of dedicated databases providing for different functions, or may be one single database providing for those functions.) Furthermore, the user computing devices 1506a-c may obtain user health and identification ("id") data (e.g., from a software app implemented thereon) from the user 1505, and transmit that data to the third-party server 1503 for storage in the database 1508 (acting as a user health and id database). Other data, such as geolocation data of the service providers 1502a-c and/or the geolocation data of the users 1505a-c also, or alternatively, may be sent from each corresponding computing device (service provider computing device 1501 or user computing device 1506) to the third-party server 1503 for automatic determination, without user input, of service provider health requirements and user compliance. To that end, one or more additional databases (e.g., a geolocation database) may be used to store such data for subsequent retrieval and/or machine learning.

Upon ingestion of various user and/or service provider data, the third-party server 1503 may utilize a digital health wallet engine 1510, which may be implemented and operated by the processor 401 illustrated in FIG. 4, to automatically generate a digital health wallet unique to a given user 1505, and that is directly accessible via a user computing device 1506. From that digital health wallet, the third-party server 1503 automatically may compose a customized digital health report that is customized to a particular service provider 1502. For instance, one airline may require four of the ten documents stored in the digital health wallet for compliance with its particular health requirements, whereas another airline may require those four in addition to one more document from the digital health wallet. Without the user 1505 having to figure out which document is necessary for which airline, the third-party server 1503 automatically extracts the required documents form the user's digital health wallet, and composes the required digital health report for the user 1505, in real-time (measured as an imperceptible human delay from the time user health data is requested by a service provider 1502) or substantially real-time (measured as a slight perceptible human delay (e.g., less than five seconds)). In one embodiment, the user 1505 may provide a user input, indicative of the requested service, via a graphical user interface ("GUI"), and that input may be transmitted to the trusted third-party server 1503 to determine the health requirements of the given service provider 1502 (i.e., by cross-referencing the health requirements via the database 1508 (acting as a user health and id database)). (The user input may be via a touch-based or voice-based input from the user, an image capture of an identifier located at the service provider location (e.g., a service provider QR code), or the like.) In another embodiment, the third-party server 1503 may automatically determine the particular service provider, without receipt of a user input from the user 1505, such as via geolocation data received from the user computing device 1506 of the user 1505 that is correlated with a known geolocation of the service provider via the database 1508 (acting as a geolocation database).

The third-party server 1503 allows for single user health and id data ingestion that may then be used for universal access. In one embodiment, the GUI may provide one or more visual indicia, as will be discussed, that directs the user 1505 which documents to upload to the cloud-based third-party platform 1500. The documents may be obtained by the user computing device 1506 via image capture, previous document storage, or the like. In another embodiment, the third-party server 1503 may provide prompts (e.g., visual, audio, etc.) to the user 1505 to guide the user 1505 on which documents need to be provided to be uploaded to the cloud-based third-party platform 1500.

The health and id data that are uploaded to the third-party server 1503 are not limited to static documents (e.g., driver's license, passport, vaccine record, etc.) that persist for an extended period of time; rather such data may also include dynamic data (e.g., body temperature) that may regularly change in short periods of time. This dynamic data is indicative of current symptoms of a user, thereby allowing a service provider 1502 to ensure not only health and id document compliance, but also current symptom compliance. For example, a user 1505 may have been vaccinated but still has a chance of catching COVID-19; in such instances, current symptom detection provides an extra layer of protection for the service provider 1502. And the user computing device 1506 (particularly a mobile computing device such as a smartphone) may provide on-the-spot symptom detection at the location of the service provider 1502. In one embodiment, the third-party server 1503 may combine the static documents with the dynamically detected symptoms into a single real-time, or substantially real-time, customized health report that may be presented, via the user computing device 1506, to the service provider 1502 for the user 1505 to obtain access to a given service. In one embodiment, the symptom results are stored in the digital health wallet along with the static documents; whereas, in another embodiment, the digital health wallet is reserved for static documents that may be extracted by the third-party server 1503 and/or the user computing device 1506 for generation of the user's digital health report.

In addition to determining, via the user's digital health report, whether the user 1505 complies with the health requirements of a given service provider 1502, the third-party server 1503 may validate the identity of the user 1505. This minimizes fraudulent use of other people's health data, the contravention of which could lead to pandemic/virus exposure at a given service provider location. For example, biometric data may be obtained upon registration of each, or at least one or more, user health and id document via the trusted cloud-based third-party platform 1500, upon symptom detection, and upon a request for access to a given service provider 1502. The use of the same biometric data to register, monitor, and validate the identity of the user through multiple points in time reduces the possibility of fraudulent use of such data. For security purposes, tokens, or equivalents thereof, may be utilized in place of sending the actual biometric data from the user computing device 1506 to the third-party server 1503. Alternatively, the actual biometric data may be directly sent to the third-party server 1503. Further, the third-party server 1503 may monitor data records from different users to determine potential fraudulent use of user health and id documents. As an example, if the same driver's license number is being utilized by two different users, the third-party server 1503 may prompt both users to perform an image capture via the user computing device 1506. The third-party server 1503 may then perform an image analysis on the captured imagery, in comparison with the image of the particular driver's license, to determine which of the two users, if either, is the actual user 1505. And even in instances where potential fraudulent use is not detected, the third-party server 1503 may request such an image capture for image analysis prior to registration of a given user 1505.

In one embodiment, the AI system 1507 may be utilized by the third-party server 1503 to interact with the user 1505 via the user computing device 1506. For example, a virtual assistant or chat bot may be rendered (visually, in an auditory manner, or both) to interact with the user 1505 to compose the digital health wallet, generate customized health reports for various service providers 1502, detect symptoms of the user 1505, and present the customized health report to the service provider. As an example, the AI system 1507 may monitor the expiration dates of documents (e.g., driver's license, passport, vaccine records, etc.) and may provide automated alerts to the user 1505 to alert the user 1505 to the need for renewal of the soon-to-be expired documents. The AI system 1507 may also present different ways to renew such documents (e.g., the closest geolocation (potentially displayed via a map) and operating times for a vaccine injection). As yet another example, the AI system 1507 may alert the user 1505 to the need for symptom monitoring (i.e., a visual, audio, or haptic alert may let the user 1505 know that he or she should position his or her user computing device 1506 within proximity (e.g., near the forehead) for symptom detection.) Also, the AI system 1507 may provide guidance for movement of the user computing device 1506 to a position that is close enough to, and/or far enough away from, the user 1505 to perform an accurate symptom measurement.

Furthermore, the AI system 1507 may manage item retention for items stored in the digital health wallet. For example, the AI system 1507 may determine whether certain items (e.g., boarding pass, expired driver's license, etc.) are no longer of use to the user 1505, and delete those items. To determine such usage, the AI system 1507 may monitor use history by the user 1505. For instance, some users 1505 may have a need to access old boarding passes to account for travel expenses, whereas other users 1505 may not have such a need. Accordingly, on a per-user basis, the AI system 1507 may use predictive analytics, based on machine learning from previous user habits and frequented geolocations, to manage digital wallet item retention, select venues for health and/or id item procurement or renewal, and interact with the user 1505.

The operation of the cloud-based digital health wallet platform 1500 is directed to specific asserted improvements in computing capabilities, namely user id validation for health-related data. The mobile device biometric technology implemented in communication with the cloud-based digital health wallet platform 1500 allows for local and/or cloud-based validation of a user's digital health wallet to obtain a service. Furthermore, the use of one or more sensors within the mobile computing device allow for symptom detection to be used with, or integrated within, the health digital wallet. The AI system 1507 may be used to monitor and guide interactions with such sensors. Moreover, the cloud-based digital health wallet platform 1500 minimizes data redundancy by providing for a universal GUI that allows for a single health-related data repository, rather than a user having to provide health-related documents to different webportals of different service provider webportals. For example, the computer hardware needed at a service provider location to review health-related data of a user may be minimized, or possibly avoided, because the functionality is built into the cloud-based digital health wallet platform 1500. Therefore, the computer hardware independence realized from use of the cloud-based digital health wallet platform 1500 allows service providers 1502 to provide services in compliance with their health protocols in a computationally efficient manner that reduces network transmissions, redundancies, and bandwidth. These improvements in computer technology go beyond well-understood, conventional activities.

The devices and users illustrated in FIG. 15 are provided only for exemplary purposes. Different and various quantities of users and devices may be used instead.

The phrase "health-related" is used herein to connote documents and/or items associated with obtaining a service based upon a review of those documents, part of which are health-specific. For example, a driver's license is considered a health-related document because it is used in conjunction with a vaccine record to obtain access to a service.

Figure 16:
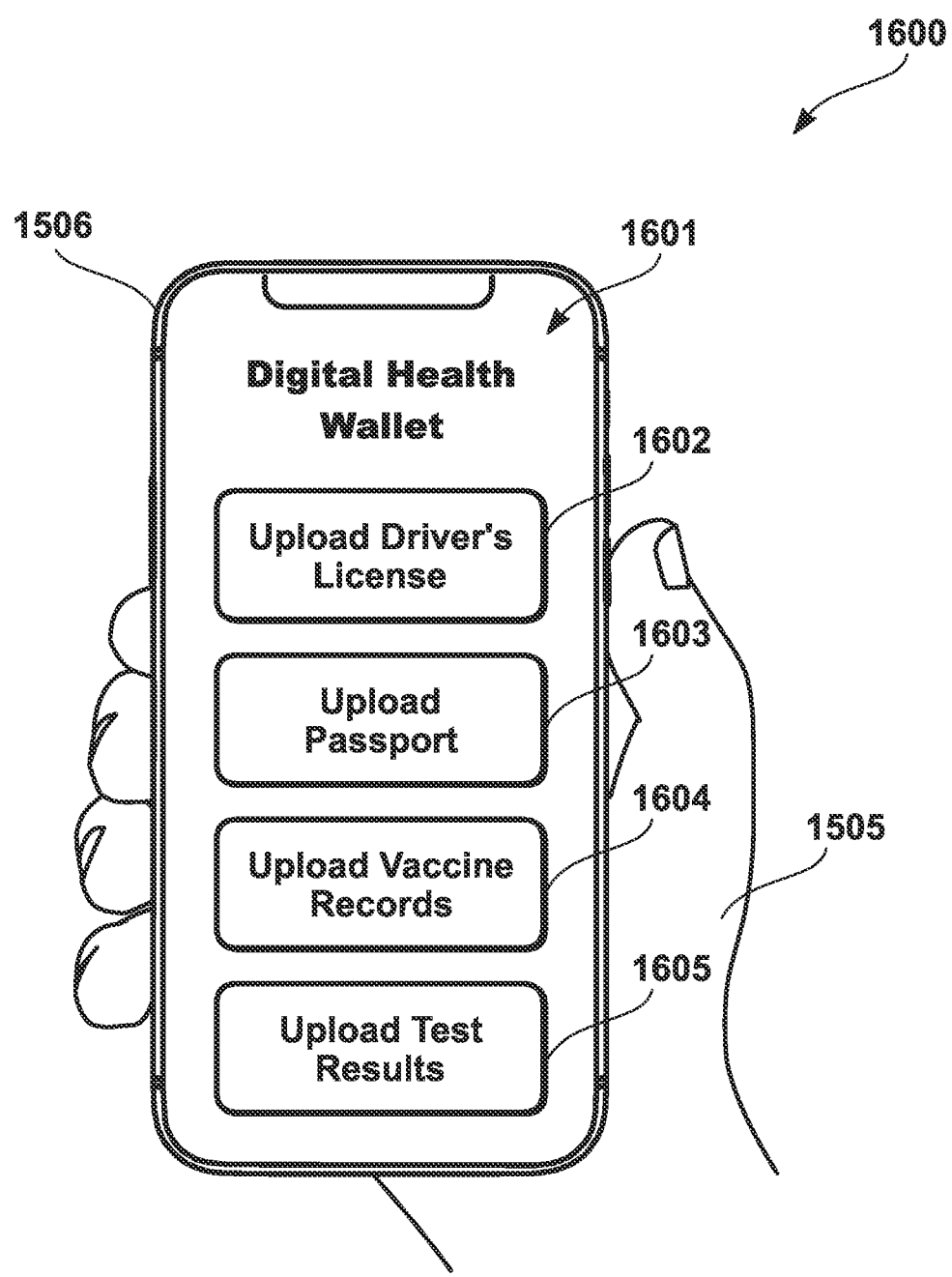
FIG. 16 illustrates an example of a digital wallet GUI that may be rendered by the user computing device illustrated in FIG. 15.

FIG. 16 illustrates an example 1600 of a digital wallet GUI 1601 that may be rendered by the user computing device 1506 illustrated in FIG. 15. In particular, the digital wallet GUI 1601 allows the user 1505 to provide user inputs of various data via various GUI indicia (e.g., buttons), such as driver's license id button 1602, passport indicium 1603, vaccine record indicium 1604, and test results indicium 1605. (Other health-related indicia than those illustrated may be utilized. For example, a boarding pass may be uploaded.)

In one embodiment, the user 1505 may perform image capture via an image capture device (e.g., camera) integrated within the user computing device 1506. Alternatively, these health-related items may be electronically transferred via another means.

Figure 17A:
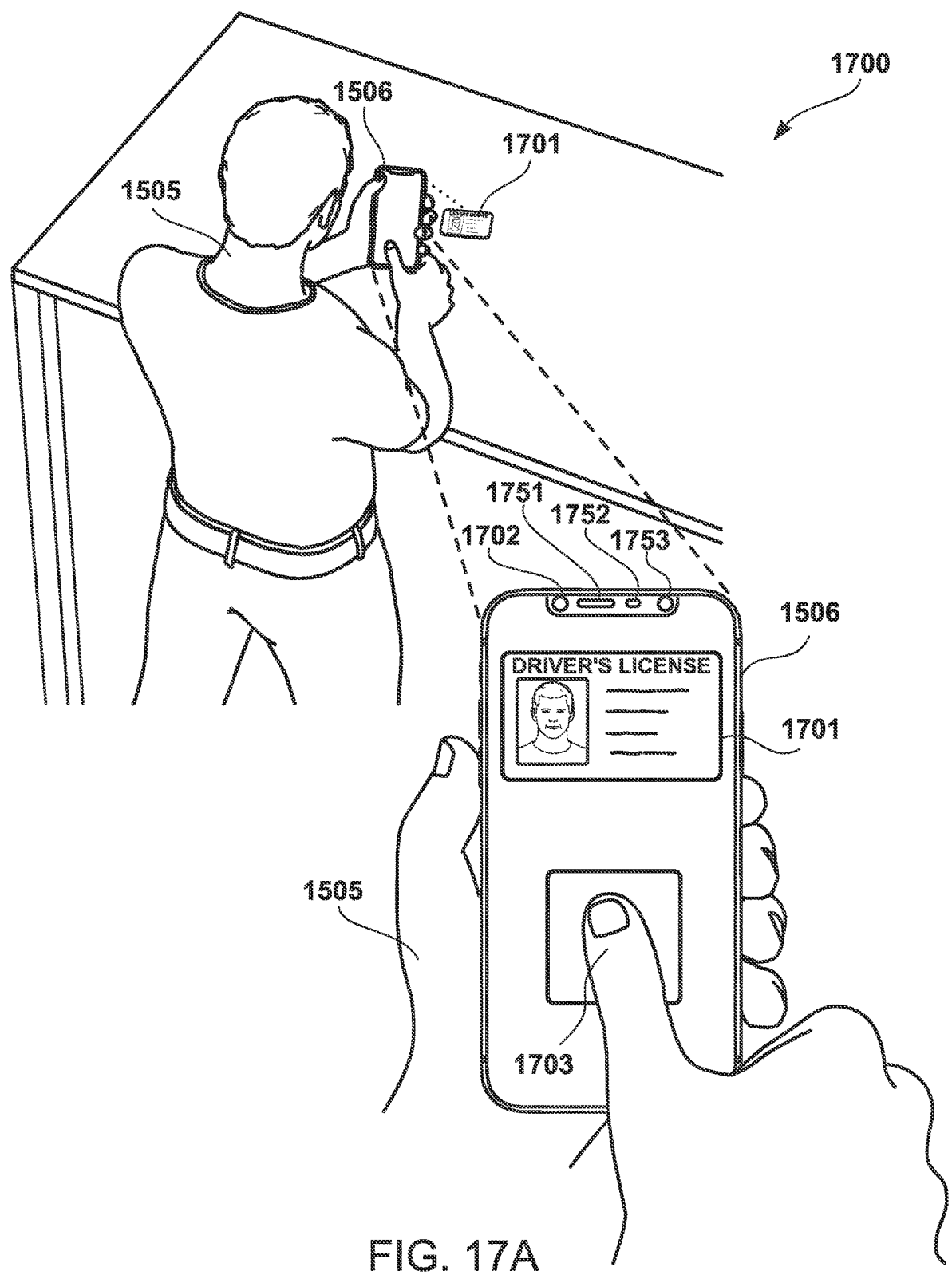
FIG. 17A illustrates the user performing an image capture of a driver's license.
Figure 17B:
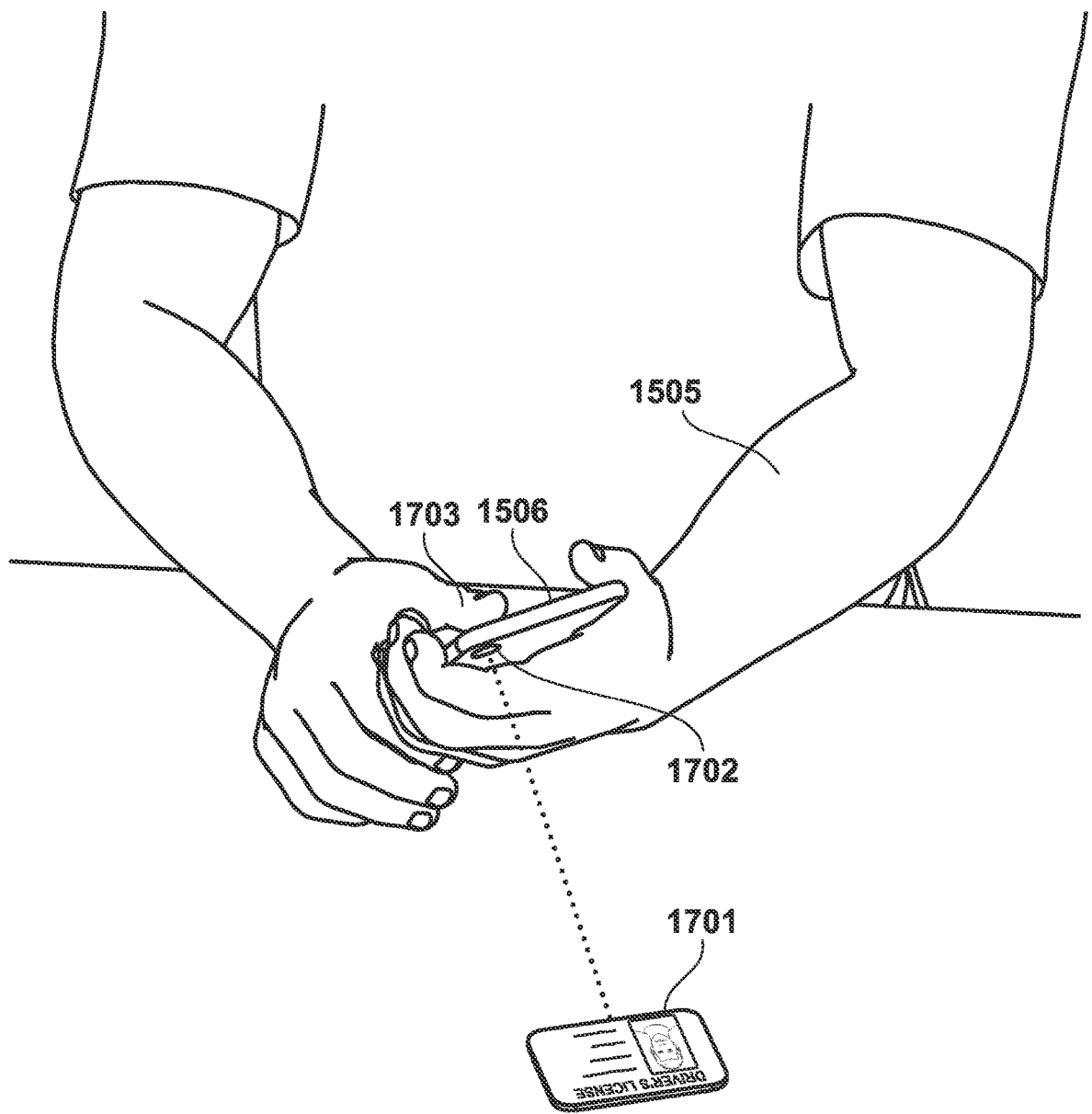
FIG. 17B illustrates a rear view of the camera illustrated in FIG. 17A.
Figure 17C:
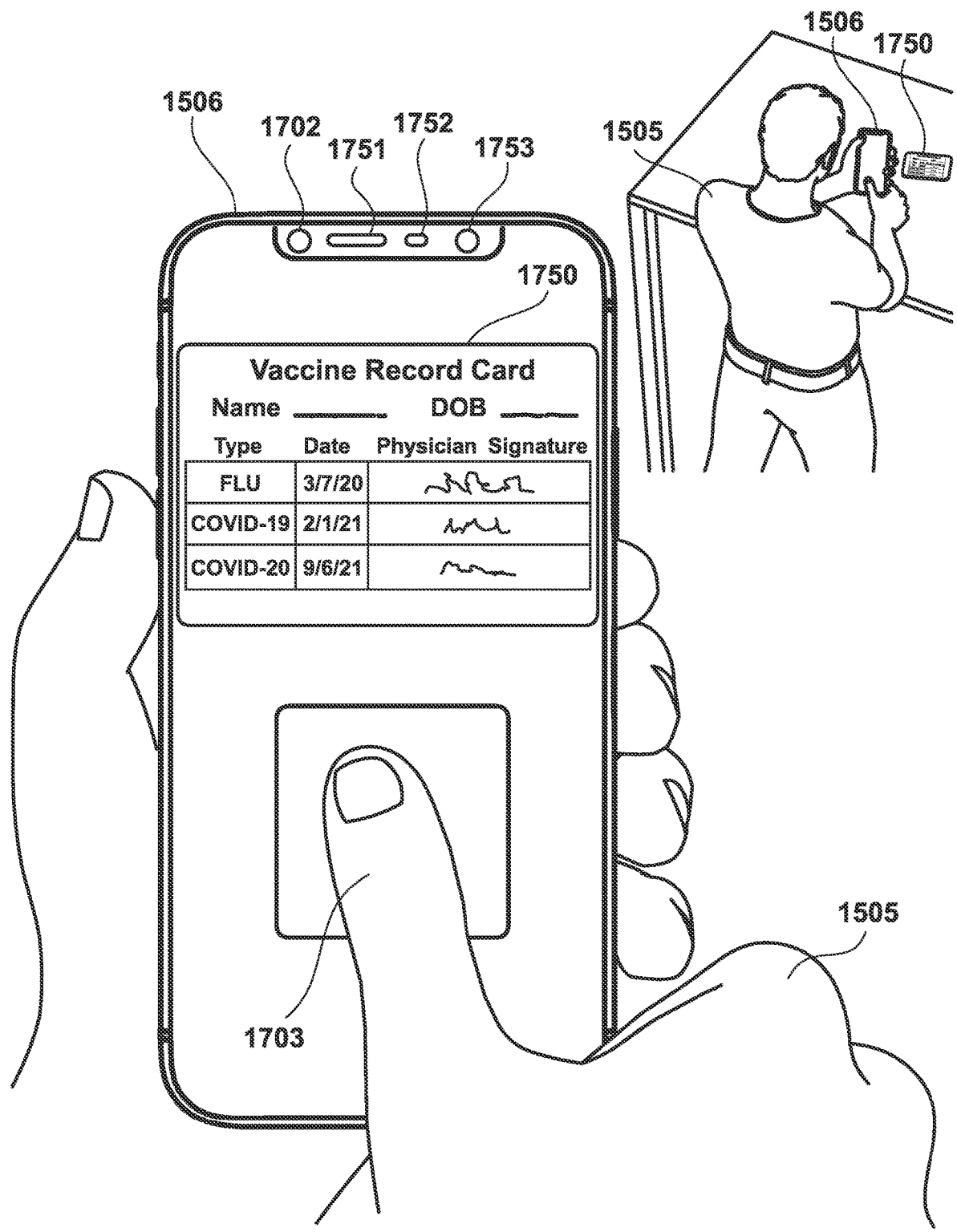
FIG. 17C illustrates the user performing an image capture of a COVID-19 vaccine record.

In essence, the user 1505 registers the health-related items via a registration process. To help ensure that each health-related item is that of the user 1505, the cloud-based digital health wallet platform 1500 may necessitate a per-item biometric registration for subsequent validation. FIGS. 17A-17C illustrate an example 1700 in which the user 1505 utilizes the user mobile computing device 1506, such as a smartphone, to register health-related items with into the digital wallet GUI 1601 illustrated in FIG. 16. For instance, FIG. 17A illustrates the user 1505 performing an image capture of a driver's license 1701. The user 1505 holds the user computing device 1506 in proximity to the driver's license 1701, and utilizes an image capture device 1702 integrated into the user computing device 1506 to perform the image capture. Furthermore, prior to, concurrently with, or subsequent to performing the image capture, the user 1505 may register a biometric that is tied to the registration of the driver's license. For example, the user 1505 may place his or her thumb 1703 on the user computing device 1506 to register his or her thumbprint with the driver's license 1701. (Other forms of biometrics, such as fingerprint scans, palm scans, iris scans, facial recognition scans, etc. may be used instead of a thumbprint.) In one embodiment, the actual biometric is locally stored with the document in the digital health wallet within a local storage device of the user computing device 1506. A coded version of the biometric along with an un-coded version of the thumbprint may be transmitted to the third-party server 1503 for registration of the driver's license with a validation token on the cloud-based platform. (Alternatively, the driver's license 1701 may also be coded in a similar or different manner to that of the biometric.) Accordingly, in this embodiment, the biometric features of the user 1505 are not transmitted anywhere outside of the user computing device 1506 for enhanced security. In another embodiment, the biometric feature may be sent directly to the third-party server 1503 in an un-coded format. (The term "coding" is intended herein to refer to the process of changing the format of a digital feature of item so that it is not reconstructed by the third-party server 1503. Accordingly, standard encryption technologies that allow for decryption by the third-party server 1503 may be performed herein without being characterized as "coded" herein.)

The user computing device may also have an integrated infrared ("IR") camera, which may be utilized to measure symptoms (e.g., a thermometer check, one or more speakers 1752 to emit audio, and a microphone 1753 to capture audio.

FIG. 17B illustrates a rear view of the camera 1702 illustrated in FIG. 17A. Alternatively, different image capture devices may be utilized for frontal and rear image capture.

As another example, FIG. 17C illustrates the user 1505 performing an image capture of a COVID-19 vaccine record 1750. Similar biometric feature registration may be performed for the vaccine record 1750 as the driver's license 1701 illustrated in FIG. 17A. (The examples of a driver's license and a vaccine record are provided for exemplary purposes only, and are intended to be non-limiting.) In one embodiment, the particular biometric feature that is used for a given document may be determined as per a health requirement from a service provider compliance requirement that is received by the third-party server 1503 from the service providers 1502. For example, an iris scan may be necessitated for a driver's license, whereas a thumbprint may be necessitated for a vaccine record. The third-party server 1503 may manage the different biometric requirements, if any (some documents may not require a biometric feature), for the user 1505 to access a service of a particular service provider 1502.

Figure 18A:
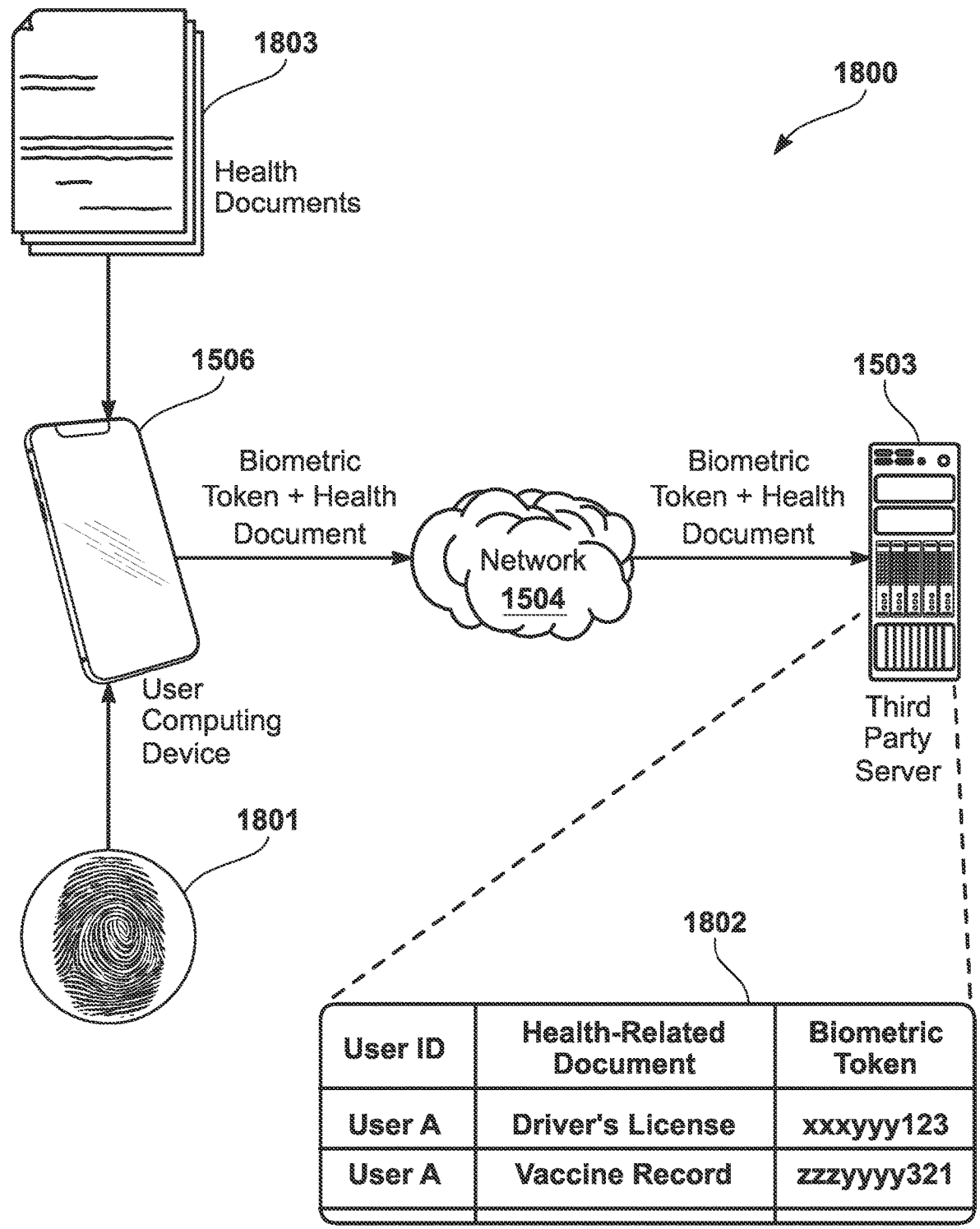
FIG. 18A illustrates a system configuration for transmission of health-related documents and biometric tokens.
Figure 18B:
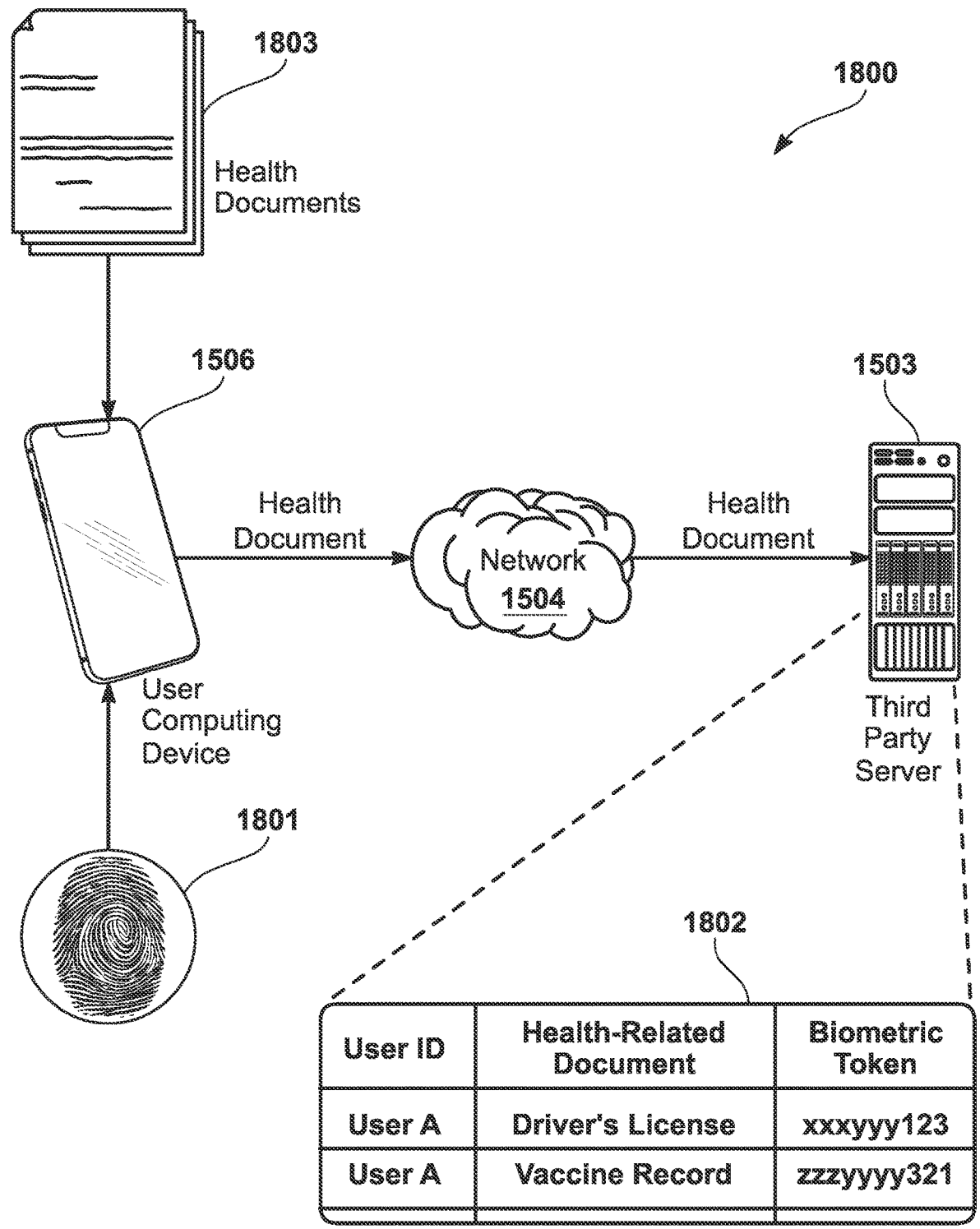
FIG. 18B illustrates a system configuration for local biometric registration.

FIGS. 18A and 18B illustrate various system configurations for biometric token configuration. FIG. 18A illustrates a system configuration 1800 for transmission of health-related documents 1803 and biometric tokens. From the user computing device 1506, a biometric token is transmitted along with a health-related document 1803 via the network 1504 to the third-party server 1503. To protect the privacy of the user's biometric features, the biometric token is sent with the health-related document 1803. As an example, a hash function that is known to the user computing device 1506 may be utilized to generate the biometric token. (Various one-way, two-way, and other coding functions may be utilized to generate the biometric token.) The third-party server 1503 may store a biometric validation table 1802 (also referred to herein as a biometric table 1802) that may be used to store the biometric tokens for each health-related document 1803 in the digital health wallet, or potentially a biometric token for the entire digital health wallet. This biometric validation table 1802 is used by the third-party server 1503 not only to store the biometric tokens for registration, but also for validation of a particular health-related document 1803 or digital health wallet upon a request for access to a service of a service provider 1502. In other words, the biometric token is a coded version of the biometric feature that allows for subsequent confirmation that use of a digital wallet to obtain a service is actually for the person that first registered the health-related documents 1803. As an example, if a first user registered his or her health-related documents 1803 via the digital health wallet using his or her thumbprint 1801, and then had his or her smartphone stolen, a second unscrupulous user that stole the smartphone would not be able to use the digital health wallet of the first user because the biometrics provided by the second user, at the time of a service request, would not correlate with the biometrics in the biometric table 1802 stored for the first user (e.g., corresponding to a user id for the first user). Accordingly, the system configuration 1800 is a technological fraud prevention solution that restricts usage of another's health records for purposes of obtaining access to a service from a service provider 1502.

By way of contrast, FIG. 18B illustrates a system configuration 1850 for local biometric registration. While the health-related documents 1803 are still sent to the third-party server 1503 for cloud-based storage, just as in the system configuration 1800 illustrated in FIG. 18A, the biometric tokens that are generated by the user computing device 1506 are also stored locally on the user computing device 1506, without being transmitted to the third-party server 1503. In this instance, even an un-coded version of the biometric features of the user 1505 is not stored on the user computing device 1506; rather the biometric table 1802 is stored locally on the user computing device 1506 of the user 1505. Subsequent validation of the biometric feature of the user, at the time of a request of a service from the service provider 1502, would then be performed by the user computing device 1506.

The biometric validation table 1802 may be a data structure (e.g., two-dimensional array, one-dimensional array, double linked-list, single linked-list, tree, blockchain, etc.) that is optimized for real-time, or substantially real-time, biometric validation. In other words, the user 1505 should be able to have his or her digital health-related documents 1803 in his or her digital health wallet validated with a humanly imperceptible, or slightly perceptible, delay. To effectuate such computing efficiency, the biometric validation table 1802 each digital health wallet may have specific fields corresponding to biometric feature labels (e.g., iris scan, thumbprint, palm scan, etc.) for the user 1505. In a corresponding field, the coded biometric input for that biometric feature specific to the user 1505 is stored for subsequent validation. In one embodiment, a packet header, of a validation packet, contains a digital flag, or equivalent thereto, corresponding to the type of biometric feature captured for validation. For example, the software app on the user computing device 1506 may generate a digital representation corresponding to an iris scan, potentially as determined by a protocol of the cloud-based digital health wallet platform 1500. A corresponding digital flag (i.e., short-form code) may identify the digital representation as an iris scan prior to being transmitted from the user mobile computing device 1506 to the cloud-based digital health wallet platform 1500. With that digital flag, the cloud-based digital health wallet platform 1500 may then perform a search of a user-specific biometric validation table 1802 to determine the corresponding coded biometric input and whether it matches the subsequently inputted biometric input for biometric validation. As a result, the cloud-based digital health wallet platform 1500 improves the security of digital health documents, while improving the computational efficiency of searching and analyzing a potential biometric match. Furthermore, network bandwidth is reduced since the digital representation (i.e., the iris scan) itself does not have to be transmitted; only the coded biometric feature, which may be of a significantly smaller size than the digital representation. For example, in contrast with transmission of imagery corresponding to an iris scan, which be a file of significant size, the coded iris scan may be a numeric representation (e.g., a hash from a hash function). Alternatively, the digital flag may be stored in the body of the packet.

Although use of biometric tokens may provide an enhanced level of security for the cloud-based digital health wallet platform 1500, registration of health-related documents may be performed without such biometric tokens, or any biometric feature for that matter.

Figure 19:
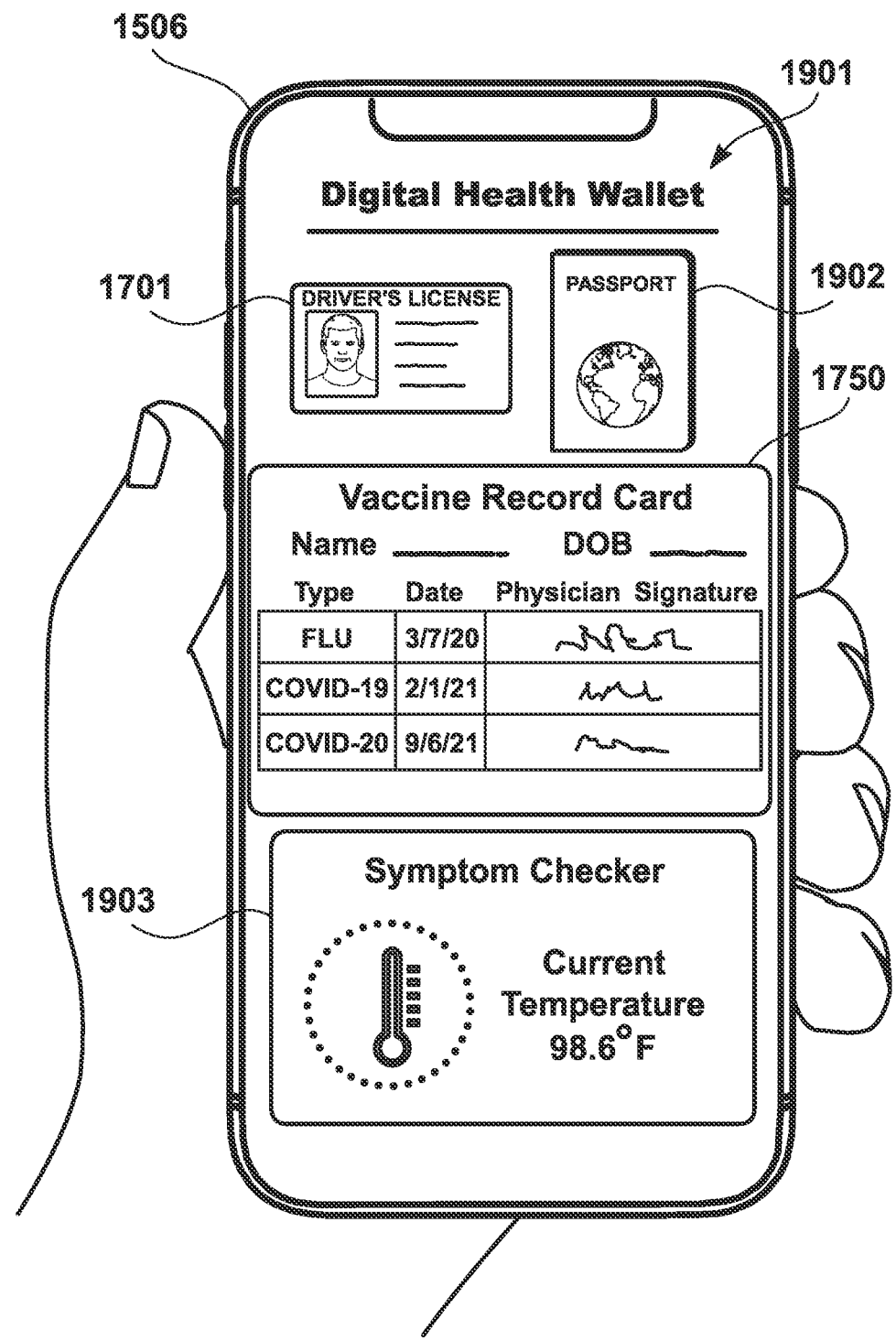
FIG. 19 illustrates an example of a digital health wallet GUI that may be rendered on the user computing device.

Subsequent to registration of the various documents, a digital health wallet is generated. FIG. 19 illustrates an example of a digital health wallet GUI 1901 that may be rendered on the user computing device 1506. As an example, the digital health wallet GUI 1901 may have various visual indicia (e.g., icons) or images (e.g., miniaturized photographs) corresponding to the various documents. For example, an image corresponding the driver's license 1701, a passport 1902, and the vaccine record 1750 may be rendered. (The foregoing are just examples; other documents and items may be in the digital wallet.) Furthermore, the digital health wallet GUI 1901 may include various visual and/or audio indicia corresponding to the measured health symptoms (e.g., temperature reading performed via one or more sensors in the user computing device 1506) of the user 1505. For example, a digital symptom checker 1903 may be rendered within the digital health wallet GUI 1901 to display the current (e.g., measured within a predetermined time period) temperature of the user by the IR camera 1751, illustrated in FIG. 17A.

Figure 20A:
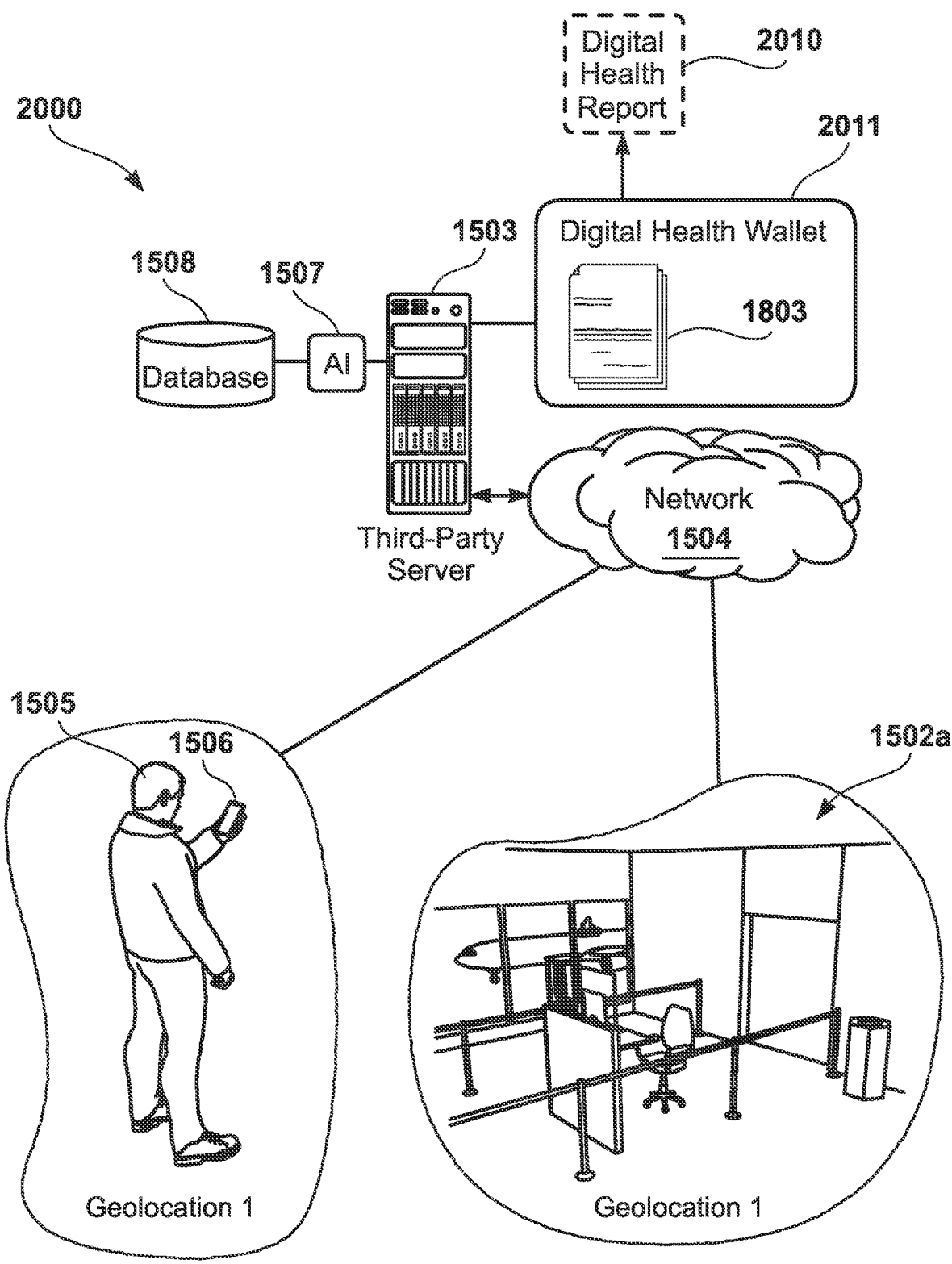
FIG. 20A illustrates a geolocation-based configuration for automatic extraction of relevant health-related documents based on the geolocation of the user in relation to the geolocation of a service provider.
Figure 20B:
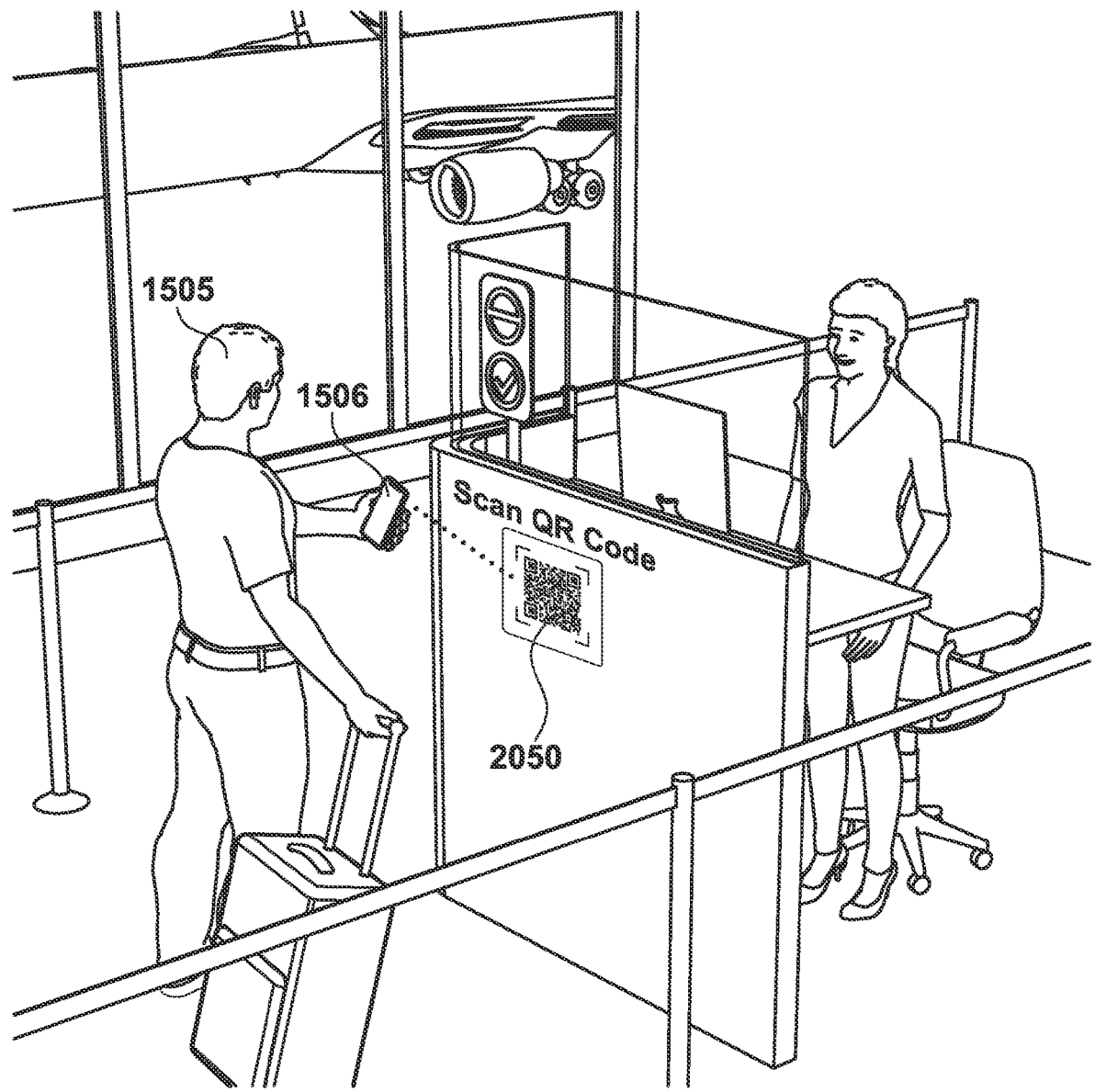
FIG. 20B illustrates the geolocation being determined via a user input that is effectuated via the user computing device by the user scanning a coded representation.

Although the digital health wallet may include an assortment of various documents, the cloud-based digital health wallet platform 1500 obviates the need for a user to search through the digital health wallet for relevant health-related documents. For instance, FIG. 20A illustrates a geolocation-based configuration 2000 for automatic extraction of relevant health-related documents based on the geolocation of the user 1505 in relation to the geolocation of a service provider 1502. Upon a determination that the user 1505 is at the same geolocation as a particular service provider 1502, the third-party server 1503 may determine the health compliance requirements of the service provider 1502, validate (e.g., via receipt of the same biometric token for each health-related document or for the digital health wallet as a whole) that the user 1505 is the same user that registered health-related documents in the digital health wallet, and extract the relevant health-related documents that are most pertinent to compliance with those health requirements. The third-party server 1503 may then generate a digital health report 2010 that may be used for the user 1505 to obtain access to the service provided by the service provider 1502. In one embodiment, the geolocation is automatically determined via mobile GPS coordinates obtained from the user computing device 1506, which may be correlated with static GPS coordinates of the service provider 1502; the correlation may be evaluated based upon a predetermined correlation matching threshold (e.g., within a tolerance of five to ten percent; although other percentages may be utilized instead). In another embodiment, as illustrated in FIG. 20B, the geolocation is determined via a user input that is effectuated via the user computing device by the user 1505 scanning a coded representation 2050, such as a QR code, corresponding to the service provider at the location of the service provider. In yet another embodiment, the user input is effectuated by the user providing an input (e.g., text, audio, etc.) that specifically names the service provider and/or service provider location.

A digital health report 2010 may be generated as a subset of a digital health wallet 2011. For example, the digital health wallet 2011 may have a plurality of health-related documents 1803, from which a subset is extracted to compose the digital health report based on the specific health compliance requirements of a given service provider 1502. The subset may be less than all of the health-related documents, or potentially all of them, depending on the specific health compliance requirements of the given service provider 1502.

Figure 21A:
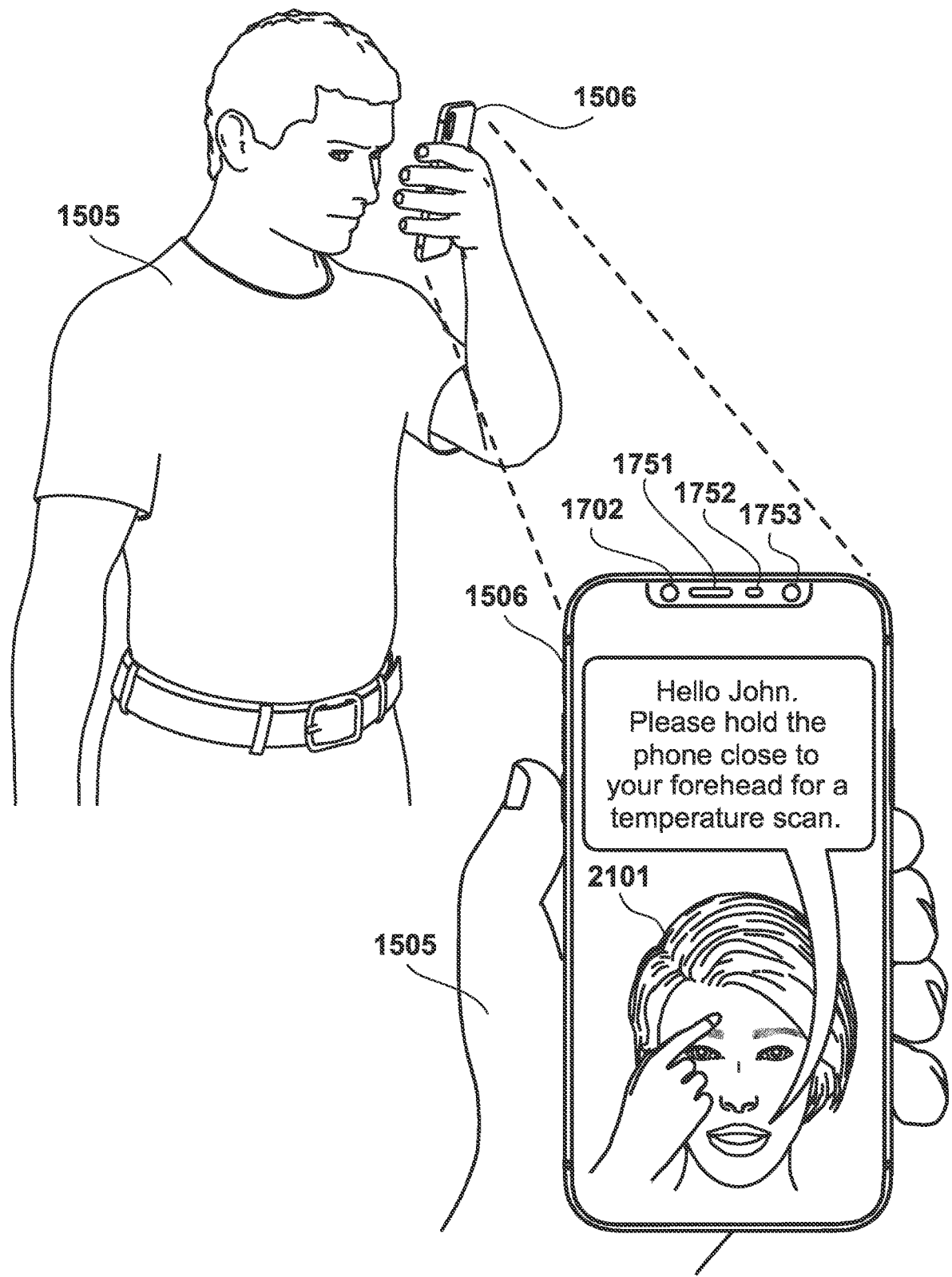
FIG. 21A illustrates a virtual avatar prompting the user to move the user computing device closer to his or her forehead to take a temperature read via the IR camera.
Figure 21B:
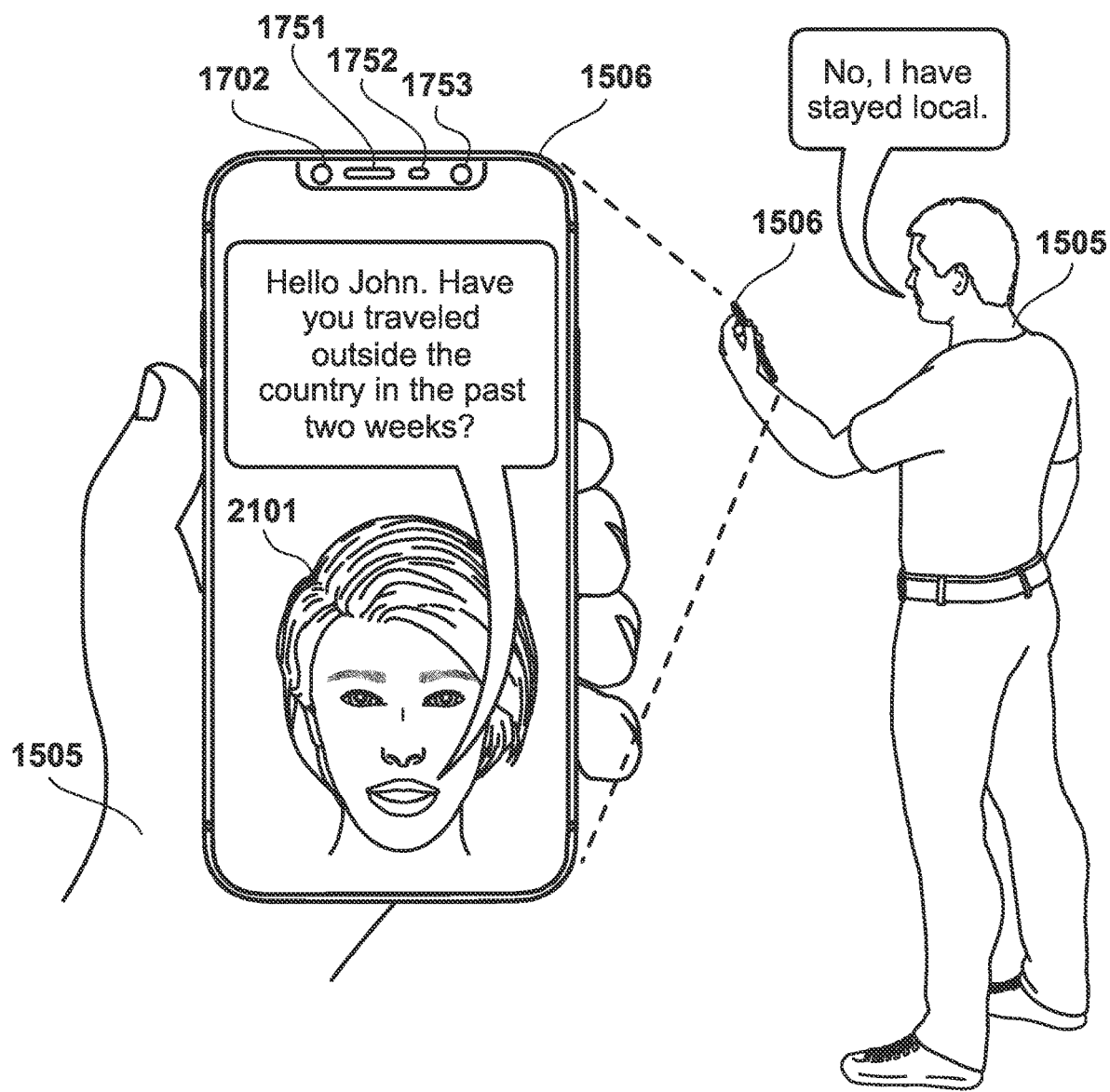
FIG. 21B illustrates the virtual avatar asking the user various questions required by the service provider.

As part of the generation of the digital health report 2010, the third-party server 1503 may utilize the AI system 1507 to interact with the user 1505 to provide additional data not present within the health-related documents. Examples of such interactions are illustrated in FIGS. 21A and 21B via a virtual avatar 2101. For instance, FIG. 21A illustrates the virtual avatar 2101 prompting the user 1505 to move the user computing device 1506 closer to his or her forehead to take a temperature read via the IR camera 1751. As another example, as illustrated in FIG. 21B, the virtual avatar 2101 may ask the user 1505 (via audio, text, and/or visual prompts) various questions required by the service provider 1502, such as whether the user 1505 recently traveled outside of the country. The audio from the virtual avatar is emitted from the speaker 1752, and the audio emitted from the user 1505 is captured via the microphone 1753. Although these interactions may occur upon a match of the geolocation of the user 1505 and the service provider 1502, they potentially may occur prior to such a geolocation match. For example, the AI system 1507 may analyze other data in the digital health wallet, such as a boarding pass, to determine an upcoming travel itinerary for the user 1505. For instance, the AI system 1507 may send an alert to the user computing device 1506 three hours prior to a departure time indicated on a boarding pass. As another example, the AI system 1507 may determine various travel patterns of the user 1505 (e.g., at particular times of the day, week, or month) to determine potential travel of the user 1505. Accordingly, the AI system 1507 may send an alert (e.g., popup message, audio alert, etc.) to the user 1505 to perform symptom checks and answer various questions corresponding to the predicted service provider 1502 prior to the user 1505 travelling to the location of that service provider 1502; the result being convenience to the user 1505 and unnecessary virus/pandemic exposure to the service provider 1502. Travel patterns are just one example of user habit patterns that may be analyzed by the AI system 1507. A probabilistic analysis may be performed by the AI system 1507 on a variety of different user habit patterns to determine the likelihood of the user 1505 performing that habit in a given instance. For instance, a determination may be made by the AI system 1507 as to whether the likelihood of the user 1505 performing a particular habit exceeds a given probabilistic threshold.

Figure 22A:
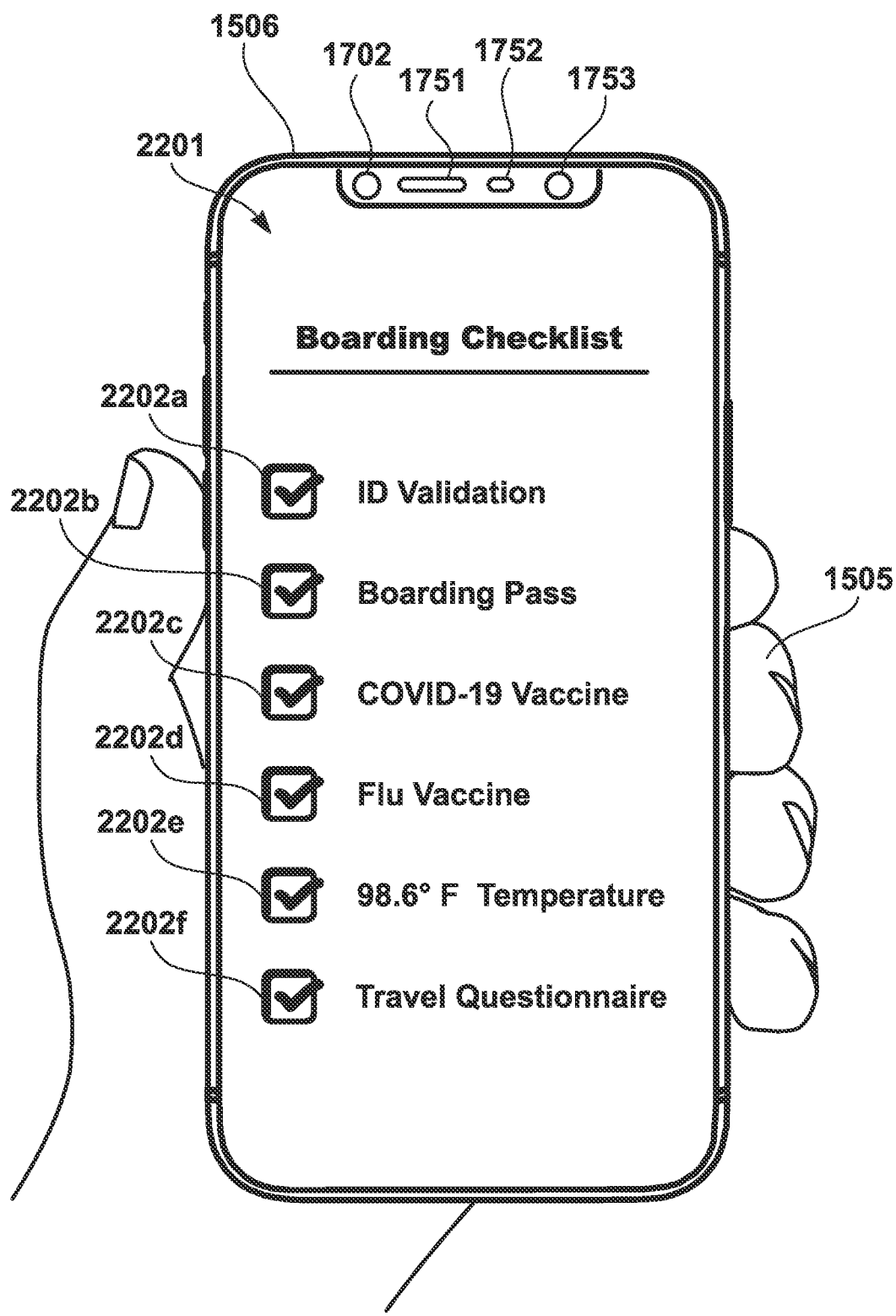
FIG. 22A illustrates an example of a generated health report.

An example of the generated digital health report is illustrated in FIG. 22A. In one embodiment, the digital health report 2010, illustrated in FIG. 20, is rendered on the display screen of the user computing device 1506 at the location of the service provider 1502 at the time of a request for, or access to, a service. Furthermore, the digital health report 2010 may rendered via a compliance GUI 2201, potentially with various compliance indicia 2202 (e.g., checkmarks) for convenient review by service provider personnel. For instance, an airline representative 2203 may visually scan an id compliance indicium 2202a, a boarding pass compliance indicium 2202b, a COVID-19 vaccine compliance indicium 2202c, a flu vaccine 2202d, temperature reading compliance 2202e (e.g., within a certain tolerance threshold), and travel questionnaire 2202f. (The foregoing indicia are provided only as examples; other or different indicia may be utilized instead.)

Figure 22B:
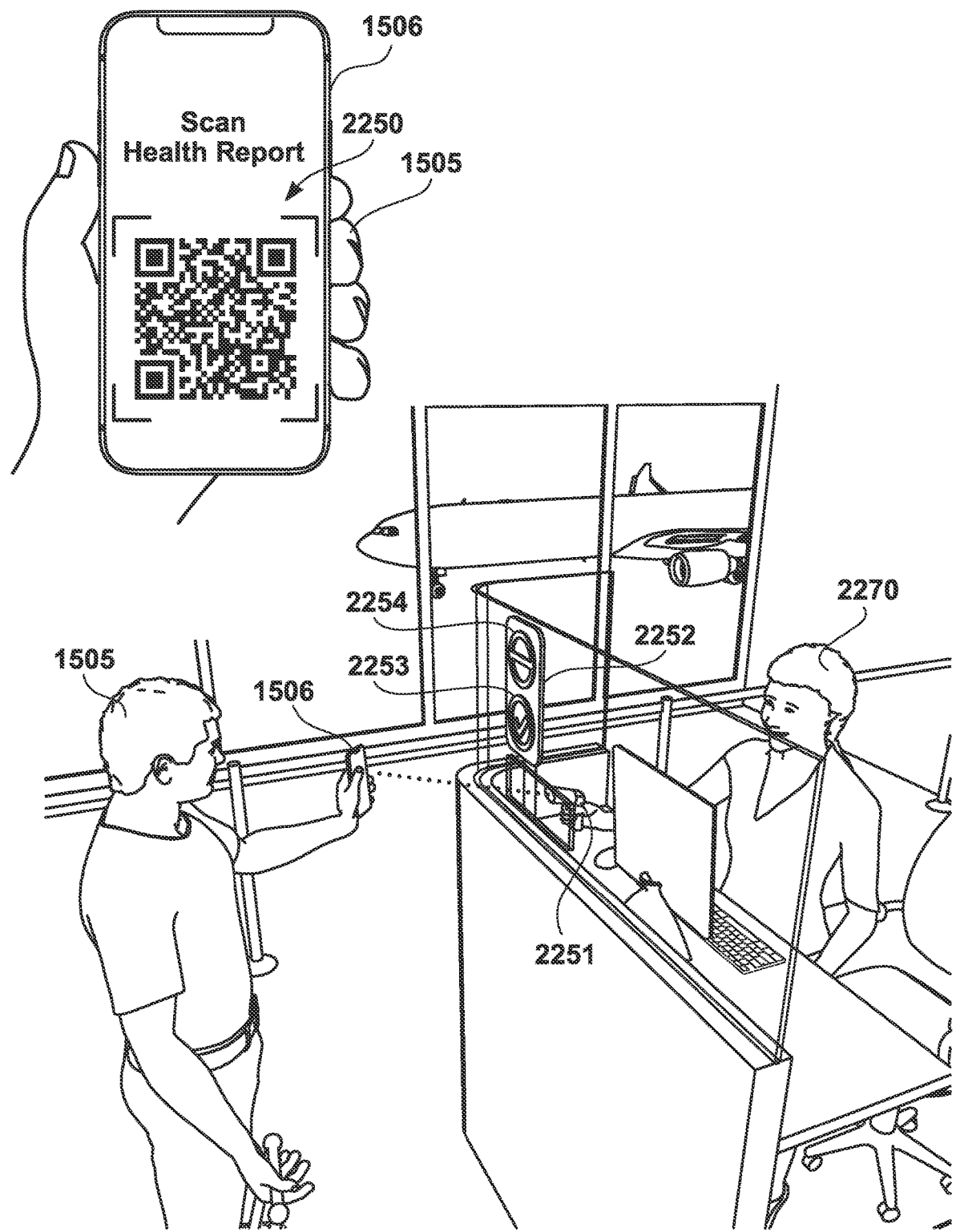
FIG. 22B illustrates a coded representation of the health report of the cloud-based digital health wallet platform.

Alternatively, as illustrated in FIG. 22B, the cloud-based digital health wallet platform 1500 may generate a coded representation (e.g., QR code 2250) of the digital health report. (The phrase "coded representation" may be deconstructed to allow for return of the health report to its original form by the service provider 1502, thereby having a different meaning than "coding" with respect to biometric features provided for herein.) A coded representation scanner 2251 (e.g., QR code scanner) may scan the coded representation of the digital health report to automatically decode the health report and determine compliance with the health requirements of the service provider 1502. (The coded representation scanner 2251 may be in operable communication with the third-party server 1503 or a service provider server, which may determine health requirement compliance; alternatively, the coded representation scanner 2251 may have a processor that is pre-programmed with the service provider healthcare requirements, and performs the health compliance assessment locally) the coded representation scanner 2251 may be operated by a service provider representative 2270, or may be positioned at the service provider location for automatic scanning without operation by the service provider representative 2270.

Furthermore, in one embodiment, an access device 2252, which may be in operable communication with the coded representation scanner to determine compliance based on the digital health report or may receive a user input from the service provider representative 2270, may have an access granted indicium 2253, which indicates access based on a compliant digital health report, and an access denied indicium 2254, which indicates accessed denied based on a non-compliant digital health poet.

Figure 23:
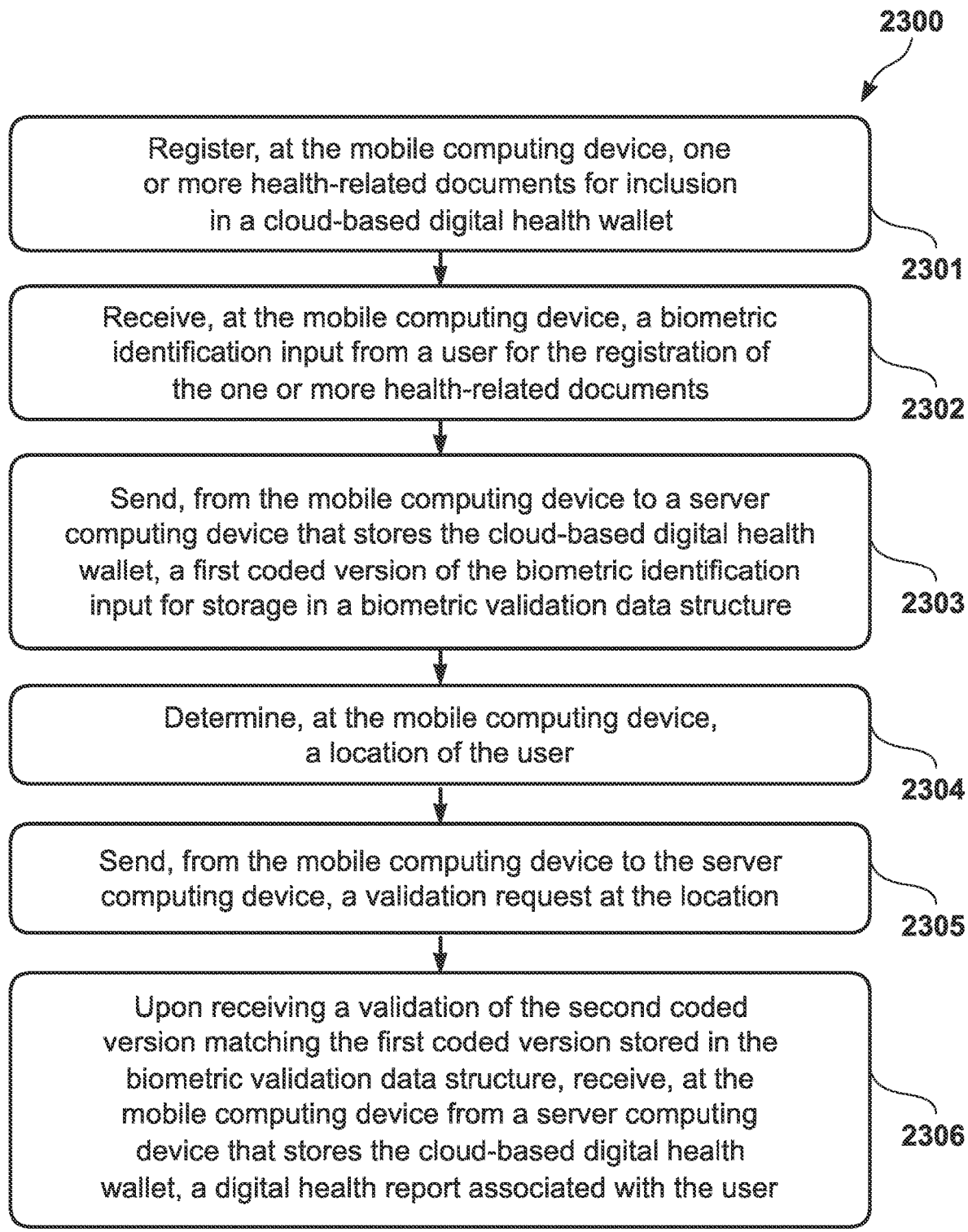
FIG. 23 illustrates a process that may be utilized by the user mobile computing device in conjunction with the cloud-based digital health wallet platform.

FIG. 23 illustrates a process 2300 that may be utilized by the user mobile computing device 1506 in conjunction with the cloud-based digital health wallet platform 1500. At a process block 2301, the process 2300 registers, at the user mobile computing device 1506, one or more health-related documents for inclusion in the cloud-based digital health wallet. Furthermore, at a process block 2302, the process 2300 receives, at the user mobile computing device 1506, a biometric identification input from the user 1505 for the registration of the one or more health-related documents. At a process block 2303, the process 2300 sends, from the user mobile computing device 1506 to a server computing device 1503 that stores the cloud-based digital health wallet, a first coded version of the biometric identification input for storage in a biometric validation data structure. Additionally, at a process block 2304, the process 2300 determines, at the user mobile computing device 1506, a location of the user 1505. Moreover, at a process block 2305, the process 2300 sends, from the user mobile computing device 1506 to the server computing device 1503, a validation request at the location. The validation request includes a second coded version of a subsequently inputted biometric input from the user at the location. Upon receiving a validation of the second coded version matching the first coded version stored in the biometric validation data structure, the process 2306 receives, at the user mobile computing device 1506 from the server computing device 1503 that stores the cloud-based digital health wallet, a digital health report associated with the user 1505. The digital health report includes data based on a subset of the one or more health-related documents selected according to one or more health compliance requirements of a service provider at the location. (The term "subset" is intended to mean less than the entirety, or potentially the entirety, of the health-related documents stored in the digital health wallet.)

The term "location" may encompass a geographic location, such as geolocation coordinates. Alternatively, a location may denote a service provider without specific geolocation coordinates. For example, the location may indicate just the name of a store, a restaurant, etc., whereby, the particular geolocation coordinates are not pertinent to the health requirements. For example, a restaurant chain may have the same heath compliance requirements in different states; therefore, the denotation of the restaurant chain, rather than the specific geographical coordinates, may suffice for identification of health compliance requirements.

Figure 24:
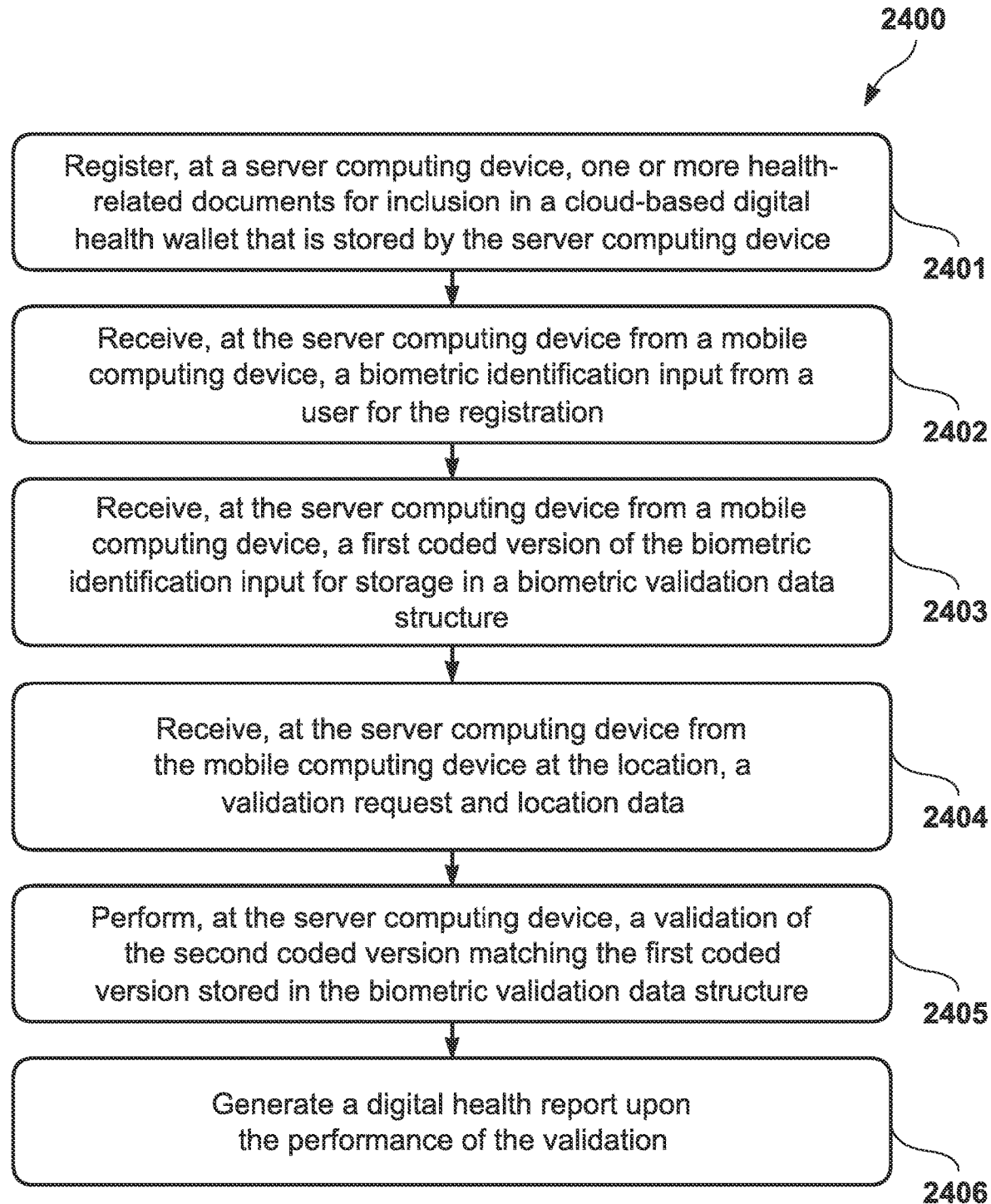
FIG. 24 illustrates a process that may be utilized by the third-party server in conjunction with the cloud-based digital health wallet platform.

Furthermore, FIG. 24 illustrates a process 2400 that may be utilized by the third-party server 1503 in conjunction with the cloud-based digital health wallet platform 1500. At a process block 2401, the process 2400 registers, at a server computing device 1503, one or more health-related documents for inclusion in a cloud-based digital health wallet that is stored by the server computing device 1503. Furthermore, at a process block 2402, the process 2400 receives, at the server computing device 1503 from the user mobile computing device 1506, a biometric identification input from a user 1505 for the registration. At a process block 2403, the process 2400 receives, at the server computing device 1503 from the mobile computing device, a first coded version of the biometric identification input for storage in a biometric validation data structure. Additionally, at a process block 2404, the process 2400 receives, at the server computing device 1503 from the user mobile computing device 1506 at the location, a validation request and location data. The validation request includes a second coded version of a subsequently inputted biometric input from the user. The subsequently inputted biometric input is at the location; whereas the first inputted biometric input may have been at a different location (i.e., during registration of a document that did not have to be at the location of the service provider 1502). The location data corresponds to the location. Also, at a process block 2405, the process 2400 performs, at the server computing device 1503, a validation of the second coded version matching the first coded version stored in the biometric validation data structure. Finally, at a process block 2406, the process 2400 generates a digital health report upon the performance of the validation. The digital health report includes data based on a subset of the one or more health-related documents selected according to one or more health compliance requirements of a service provider at the location.

It is understood that the processes, systems, apparatuses, and computer program products described herein may also be applied in other types of processes, systems, apparatuses, and computer program products. Those skilled in the art will appreciate that the various adaptations and modifications of the embodiments of the processes, systems, apparatuses, and computer program products described herein may be configured without departing from the scope and spirit of the present processes and systems. Therefore, it is to be understood that, within the scope of the appended claims, the present processes, systems, apparatuses, and computer program products may be practiced other than as specifically described herein.

We claim:

1. A computer program product comprising a non-transitory computer useable storage device having a computer readable program, wherein the computer readable program when executed on a mobile computing device causes the mobile computing device to:

register, at the mobile computing device, one or more health-related documents for inclusion in a cloud-based digital health wallet;

receive, at the mobile computing device, a biometric identification input from a user for the registration of the one or more health-related documents;

send, from the mobile computing device to a server computing device that stores the cloud-based digital health wallet, a first coded version of the biometric identification input for storage in a biometric validation data structure;

determine, at the mobile computing device, a location of the user;

send, from the mobile computing device at the location to the server computing device, a validation request and location data, the validation request including a second coded version of a subsequently inputted biometric input from the user at the location, the location data corresponding to the location; and upon receiving a validation of the second coded version matching the first coded version stored in the biometric validation data structure, receive, at the mobile computing device from the server computing device that stores the cloud-based digital health wallet, a digital health report associated with the user, the digital health report including data based on a subset of the one or more health-related documents selected according to one or more health compliance requirements of a service provider at the location.

2. The computer program product of claim 1, wherein the mobile computing device is further caused to receive instructions from an artificial intelligence system in operable communication with the server computing device based on a probabilistic analysis of user habit patterns.

3. The computer program product of claim 2, wherein the instructions direct the mobile computing device to render one or more interactive prompts to the user to perform a symptom check via one or more sensors integrated within the mobile computing device, the instructions further directing the mobile computing device to include symptom check results of the symptom check in the digital health report.

4. The computer program product of claim 2, wherein the instructions direct the mobile computing device to render one or more interactive prompts to the user to answer a questionnaire, the instructions further directing the mobile computing device to include one or more answers to the questionnaire in the digital health report.

5. The computer program product of claim 1, wherein the mobile computing device is further caused to render the digital health report on a graphical user interface for the service provider determination of access to a service at the location.

6. The computer program product of claim 1, wherein the mobile computing device is further caused to render the digital health report as a QR code on a graphical user interface at the location.

7. The computer program product of claim 1, wherein the mobile computing device is further caused to determine the location of the user via geolocation coordinates determined via a Global Positioning System.

8. The computer program product of claim 1, wherein the mobile computing device is further caused to determine the location of the user by scanning a QR code positioned at the location.

9. The computer program product of claim 1, wherein the mobile computing device is further caused to receive instructions from an artificial intelligence system in operable communication with the server computing device, the instructions directing the mobile computing device to render one or more interactive prompts to the user to update the one or more health-related documents.

10. The computer program product of claim 1, wherein the one or more health-related documents comprise one or more identification documents, the one or more identification documents selected from the group consisting of: a driver's license, a passport, a birth certificate, and a boarding pass.

11. The computer program product of claim 1, wherein the one or more health-related documents comprise one or more health records, the one or more health records elected from the group consisting of: a vaccine record, a virus test record, a health insurance card, and a physician's note.

12. A computer program product comprising a non-transitory computer useable storage device having a computer readable program, wherein the computer readable program when executed on a server computing device causes the server computing device to:
register, at the server computing device, one or more health-related documents for inclusion in a cloud-based digital health wallet that is stored by the server computing device;
receive, at the server computing device from a mobile computing device, a biometric identification input from a user for the registration;
receive, at the server computing device from the mobile computing device, a first coded version of the biometric identification input for storage in a biometric validation data structure;
receive, at the server computing device from the mobile computing device at a location, a validation request and location data, the validation request including a second coded version of a subsequently inputted biometric input from the user, the subsequently inputted biometric input being at the location, the location data corresponding to the location;
perform, at the server computing device, a validation of the second coded version matching the first coded version stored in the biometric validation data structure; and
generate a digital health report upon the performance of the validation, the digital health report including data based on a subset of the one or more health-related documents selected according to one or more health compliance requirements of a service provider at the location.

13. The computer program product of claim 12, wherein the server computing device is further caused to generate the digital health report configured to display parameters of a graphical user interface of the user mobile computing device.

14. The computer program product of claim 13, wherein the mobile computing device is further caused to generate, with an artificial intelligence system, one or more instructions based on a probabilistic analysis of user habit patterns and to send the one or more instructions to the user mobile computing device.

15. The computer program product of claim 14, wherein the instructions direct the mobile computing device to render one or more interactive prompts to the user to perform a symptom check via one or more sensors integrated within the mobile computing device, the instructions further directing the mobile computing device to include symptom check results of the symptom check in the digital health report.

16. The computer program product of claim 14, wherein the instructions direct the mobile computing device to render one or more interactive prompts to the user to answer a questionnaire, the instructions further directing the mobile computing device to include one or more answers to the questionnaire in the digital health report.

17. The computer program product of claim 13, wherein the server computing device is further caused to generate the digital health report as a QR code configured to the display parameters of a graphical user interface of the user mobile computing device.

18. The computer program product of claim 13, wherein the server computing device is further caused to receive, from the user mobile computing device, the location of the user as geolocation coordinates.

19. The computer program product of claim 13, wherein the server computing device is further caused to receive, from the user mobile computing device, the location of the user being coded as a QR code.

20. The computer program product of claim 13, wherein the server computing device is further caused to generate, with an artificial intelligence system, one or more instructions for interactive prompts to the user to update the one or more health-related documents and to send the one or more instructions to the user mobile computing device.

* * * * *